(12) United States Patent
Harada et al.

(10) Patent No.: US 11,327,060 B2
(45) Date of Patent: May 10, 2022

(54) METHOD FOR ANALYZING ENANTIOMER

(71) Applicant: Ajinomoto Co., Inc., Tokyo (JP)

(72) Inventors: Masashi Harada, Kawasaki (JP); Sachise Karakawa, Kawasaki (JP); Kazutaka Shimbo, Kawasaki (JP); Naoyuki Yamada, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 662 days.

(21) Appl. No.: 15/938,450

(22) Filed: Mar. 28, 2018

(65) Prior Publication Data
US 2018/0217113 A1 Aug. 2, 2018

Related U.S. Application Data

(63) Continuation of application No. PCT/JP2016/078576, filed on Sep. 28, 2016.

(30) Foreign Application Priority Data

Oct. 2, 2015 (JP) .............................. JP2015-197070

(51) Int. Cl.
| | | |
|---|---|---|
| *G01N 30/00* | (2006.01) | |
| *G01N 30/88* | (2006.01) | |
| *C07C 271/58* | (2006.01) | |
| *C07D 401/12* | (2006.01) | |
| *C07D 207/46* | (2006.01) | |
| *C07D 213/40* | (2006.01) | |
| *G01N 30/06* | (2006.01) | |
| *G01N 27/62* | (2021.01) | |
| *B01D 15/38* | (2006.01) | |
| *C07C 233/62* | (2006.01) | |
| *C07B 57/00* | (2006.01) | |
| *B01D 15/32* | (2006.01) | |
| *C07C 51/353* | (2006.01) | |
| *C07C 51/47* | (2006.01) | |
| *C07C 53/18* | (2006.01) | |
| *C07C 269/06* | (2006.01) | |
| *C07C 269/08* | (2006.01) | |
| *G01N 1/40* | (2006.01) | |
| *G01N 30/72* | (2006.01) | |

(52) U.S. Cl.
CPC ........... *G01N 30/88* (2013.01); *B01D 15/327* (2013.01); *B01D 15/38* (2013.01); *C07B 57/00* (2013.01); *C07C 51/353* (2013.01); *C07C 51/47* (2013.01); *C07C 53/18* (2013.01); *C07C 233/62* (2013.01); *C07C 269/06* (2013.01); *C07C 269/08* (2013.01); *C07C 271/58* (2013.01); *C07D 207/46* (2013.01); *C07D 213/40* (2013.01); *C07D 401/12* (2013.01); *G01N 1/405* (2013.01); *G01N 27/62* (2013.01); *G01N 30/06* (2013.01); *G01N 30/7233* (2013.01); *C07B 2200/07* (2013.01)

(58) Field of Classification Search
CPC ....................................................... G01N 30/88
USPC ............................................................. 436/96
See application file for complete search history.

(56) References Cited

U.S. PATENT DOCUMENTS

2012/0016157 A1  1/2012  Kim et al.

FOREIGN PATENT DOCUMENTS

| JP | 7-128319 A | 5/1995 |
|---|---|---|
| JP | 2012-521415 | 9/2012 |
| JP | 2014-034573 A | 2/2014 |

OTHER PUBLICATIONS

Kawakami et al. "An Asymmetric Synthesis of 2,4-Dimethylvalerolactone and Mevalonolactone using Chiral Binaphthyldiamine Derivatives" J. Chem. Soc., Chem. Commun., 1984; p. 779-781 (Year: 1984).*
Extended European Search Report dated Apr. 5, 2019 in corresponding European Patent Application No. 16851604.5, 6 pages.
Database CA [Online] Chemical Abstracts Service, Columbus, Ohio, US; XP002790068, 1987, retrieved from STN Database accession No. 109:145169, 3 pages.
International Search Report in Application No. PCT/JP2016/078576 dated Dec. 27, 2016.
Written Opinion in Application No. PCT/JP2016/078576 dated Dec. 27, 2016.
Junichi otoO, et al., "New Type of Derivatization Reagents for Liquid Chromatographic Resolution of Enantiomeric Hydroxyl Compounds", Chemical and Pharmaceutical Bulletin, vol. 30, No. 12, p. 4597-4599 (1982).

(Continued)

*Primary Examiner* — Christine T Mui
*Assistant Examiner* — Emily R. Berkeley
(74) *Attorney, Agent, or Firm* — Oblon, McClelland, Maier & Neustadt, L.L.P.

(57) ABSTRACT

Enantiomers may be analyzed by:

(1) reacting a mixture of a first compound and a second compound that are a pair of enantiomers with an axially chiral compound that is one of a pair of axially chiral isomers, to generate a derivative mixture containing a first derivative obtained by a reaction of the first compound with the axially chiral compound and a second derivative obtained by a reaction of the second compound with the axially chiral compound;

(2) separating the first derivative and the second derivative in the derivative mixture; and (3) detecting the separated first derivative and second derivative by mass spectrometry.

17 Claims, No Drawings

(56) References Cited

OTHER PUBLICATIONS

Sotaro Miyano, et al., "Optical Resolution of 2'-Methoxy-1,1'-binaphthyl-2-carboxylic Acid, and Application to Chiral Derivatizing Agent for HPLC Separation of Enantiomeric Alcohols and Amines", Bulletin of the Chemical Society of Japan, vol. 62, No. 5, p. 1528-1533 (1989).

Tetsutaro Hattori, et al., "Application of Acially Dissymmetric Binaphthyl Derivatives to Chiral Derivatizing Agents", Journal of Synthetic Organic Chemistry, Japan, vol. 50, No. 11, p. 986-996 (1992) with English Translation.

* cited by examiner

METHOD FOR ANALYZING ENANTIOMER

CROSS REFERENCES TO RELATED APPLICATIONS

This application is a continuation of International Patent Application No. PCT/JP2016/078576, filed on Sep. 28, 2016, and claims priority to Japanese Patent Application No. 2015-197070, filed on Oct. 2, 2015, both of which are incorporated herein by reference in their entireties.

BACKGROUND OF THE INVENTION

Field of the Invention

The present invention relates to methods for analyzing an enantiomer, and the like.

Discussion of the Background

As a method for analyzing a chiral compound, a method in which a chiral alcohol or a chiral amine is reacted with a binaphthyl compound having axial chirality to obtain a derivative and the derivative is separated by high performance liquid chromatography (HPLC) has been conventionally known.

For example, Chemical and Pharmaceutical Bulletin, 1982, Vol. 30, No. 12, pp. 4597 to 4599, which is incorporated herein by reference in its entirety, discloses a technique in which a chiral alcohol such as methyl 3-hydroxyoctanoate is reacted with methyl-1,1'-binaphthalene-2'-carbonyl nitrile to obtain a derivative and the derivative is separated by HPLC.

Bulletin of the Chemical Society of Japan, 1989, Vol. 62, No. 5, pp. 1528 to 1533 and Journal of Synthetic Organic Chemistry, Japan, 1992, Vol. 50, No. 11, pp. 986 to 996, both of which are incorporated herein by reference in their entireties, disclose a technique in which a chiral alcohol such as 1-phenyl-ethanol or a chiral amine such as 1-phenyl-ethylamine is reacted with 2'-methoxy-1,1'-binaphthyl-2-carboxylic acid chloride to obtain a derivative and the derivative is separated by HPLC.

In general analysis of a chiral compound, there is a need for separation and detection of a chiral compound having the same chemical properties and physical properties as those of the chiral compound except for optical rotation. In the conventional techniques using normal phase column chromatography described in Chemical and Pharmaceutical Bulletin, 1982, Vol. 30, No. 12, pp. 4597 to 4599; Bulletin of the Chemical Society of Japan, 1989, Vol. 62, No. 5, pp. 1528 to 1533; and Journal of Synthetic Organic Chemistry, Japan, 1992, Vol. 50, No. 11, pp. 986 to 996, the number of theoretical plates that is an index of separation is generally small. A compound having a hydrophilic group such as carboxylic acid and a primary amine, is strongly retained to a column. Therefore, separation is extremely difficult. When a group that can be detected by fluorescence or UV is used in measurement of a biological sample or a sample obtained in an environment, selective detection of only a target compound is extremely difficult due to too many impurities. For a sample from an environment and a trace amount of sample, measurement by the techniques of Chemical and Pharmaceutical Bulletin, 1982, Vol. 30, No. 12, pp. 4597 to 4599; Bulletin of the Chemical Society of Japan, 1989, Vol. 62, No. 5, pp. 1528 to 1533; and Journal of Synthetic Organic Chemistry, Japan, 1992, Vol. 50, No. 11, pp. 986 to 996 is not sufficiently made. In the living body, there are various amino acids such as acidic, basic, hydrophobic, hydrophilic, and cyclic amino acids. When enantiomers of the various amino acids are mixed, it is extremely difficult to find a condition of simultaneously separating stereoisomers of all amino acids to be measured.

Thus, there remains a need for improved methods of methods for analyzing enantiomers.

SUMMARY OF THE INVENTION

Accordingly, it is one object of the present invention to provide novel methods of methods for analyzing enantiomers.

These and other objects, which will become apparent during the following detailed description, have been achieved by the inventors' discovery that when an enantiomer is reacted with an axially chiral compound to obtain a derivative, and the derivative is separated, and then detected by mass spectrometry, the enantiomer can be analyzed at high sensitivity with high resolution.

That is, the present invention provides the following:

(1) A method for analyzing an enantiomer, comprising (1) to (3) below:

(1) reacting a mixture of a first compound and a second compound that are a pair of enantiomers with an axially chiral compound that is one of a pair of axially chiral isomers, to generate a derivative mixture containing a first derivative obtained by a reaction of the first compound with the axially chiral compound and a second derivative obtained by a reaction of the second compound with the axially chiral compound;

(2) separating the first derivative and the second derivative in the derivative mixture; and (3) detecting the separated first derivative and second derivative by mass spectrometry.

(2) The method according to (1), wherein the axially chiral isomer is represented by the general formula (I) below:

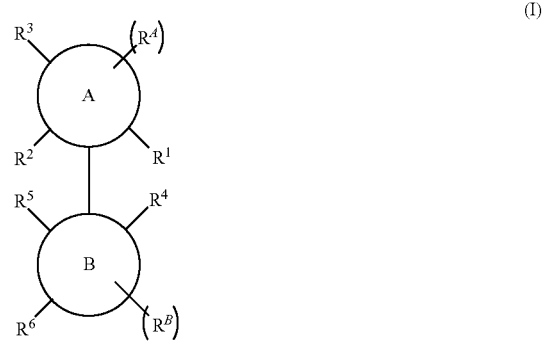

wherein
ring A and ring B each independently represent a benzene ring or a heteroaromatic ring,
a bond between the ring A and the ring B represents an axis of chirality,
$R^1$ represents a group bonded to one ring-constituting atom adjacent to a ring A-constituting atom bonded to the ring B,
$R^2$ represents a group bonded to the other ring-constituting atom adjacent to the ring A-constituting atom bonded to the ring B, $R^3$ represents a hydrogen atom or a group, or $R^2$ and $R^3$ may form a ring together, $R^4$ represents a group bonded to one ring-constituting atom adjacent to a ring B-constituting atom bonded to the ring A, $R^5$ represents a group bonded to the other ring-constituting atom adjacent to the ring B-constituting atom bonded to the ring A, $R^6$ represents a hydrogen atom or a group, or $R^5$ and $R^6$ may form a ring together, the ring A and the ring B may further have one or two $R^A$s and one or two $R^B$s that are bonded to an atom constituting each ring (wherein the one or two $R^A$s and the one or two $R^B$s each represent a group), the groups are (a) a reactive group or (b) a substituent, and the reactive group exists only in any one of $R^1$ to $R^6$, $R^A$, and $R^B$.

(3) The method according to (1), wherein the axially chiral isomer is represented by the general formula (I′) below:

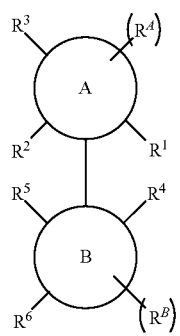

wherein ring A and ring B each independently represent a benzene ring or a heteroaromatic ring, a bond between the ring A and the ring B represents an axis of chirality, $R^1$ represents a group bonded to one ring-constituting atom adjacent to a ring A-constituting atom bonded to the ring B, $R^2$ represents a group bonded to the other ring-constituting atom adjacent to the ring A-constituting atom bonded to the ring B, $R^3$ represents a hydrogen atom or a group, or $R^2$ and $R^3$ may form a ring together, $R^4$ represents a group bonded to one ring-constituting atom adjacent to a ring B-constituting atom bonded to the ring A, $R^5$ represents a group bonded to the other ring-constituting atom adjacent to the ring B-constituting atom bonded to the ring A, $R^6$ represents a hydrogen atom or a group, or $R^5$ and $R^6$ may form a ring together, the ring A and the ring B may further have one or two $R^A$s and one or two $R^B$s that are bonded to an atom constituting each ring (wherein the one or two $R^A$s and the one or two $R^B$s each represent a group), the groups are (a) a reactive group, (b) a group having a charged atom or a chargeable atom, or (c) a substituent, the reactive group exists only in any one of $R^1$ to $R^6$, $R^A$, and $R^B$, and when the group having a charged atom or a chargeable atom does not exist in any of $R^1$ to $R^6$, $R^A$, and $R^B$, at least one of the ring A and the ring B represents a heteroaromatic ring having a charged atom or a chargeable atom, or at least one of the ring formed by $R^2$ and $R^3$ together and the ring formed by $R^5$ and $R^6$ together exists and represents a ring having a charged atom or a chargeable atom.

(4) The method according to (2) or (3), wherein the reactive group is a nucleophilic group, an electrophilic group, or a group containing at least one of a nucleophilic group and an electrophilic group.

(5) The method according to (4), wherein the reactive group is a group selected from the group consisting of:

(1) a carbonyl group having a leaving group (wherein the leaving group is selected from the group consisting of $C_1$ to $C_6$ alkyloxy, $C_1$ to $C_6$ alkylcarbonyloxy, a halogen atom, succinimidooxy, phenyloxy having an electron-withdrawing group, imidazolyl, and triazolyl);

(2) a nucleophilic group selected from the group consisting of an amino group, a hydrazino group, a hydroxy group, and a sulfanyl group;

(3) an electrophilic group selected from the group consisting of a maleimide group, an acryloylamino group, a methacryloylamino group, and a formyl group; and (4) a group containing any of the groups (1) to (3).

(6) The method according to any one of (2) to (5), wherein the reactive group is a group selected from the group consisting of:

(a1) a group represented by the general formula (i) below:

wherein $R^7$ represents a leaving group (wherein the leaving group is the same as those defined in (5)), n represents 0 or 1, $R^8$ does not exist when n is 0, and $R^8$ represents a hydrogen atom or a $C_1$ to $C_6$ alkyl group when n is 1;

(a2) a group represented by the general formula (ii) below:

wherein $R^9$ and $R^{10}$ each independently represent a hydrogen atom or a $C_1$ to $C_6$ alkyl group; and (a3) a group containing the group represented by the aforementioned general formula (i) or (ii).

(7) The method according to any one of (3) to (6), wherein the group having a charged atom or a chargeable atom is a group selected from the group consisting of:

(1) an optionally substituted amino group;

(2) an optionally substituted ammonio group;

(3) an optionally substituted guanidino group;

(4) an optionally substituted guanidinium group;

(5) an optionally substituted imino group;
(6) an optionally substituted iminium group;
(7) an optionally substituted nitrogen-containing cyclic group;
(8) an optionally substituted phosphino group;
(9) an optionally substituted phosphonio group;
(10) an optionally substituted oxy group;
(11) an optionally substituted thio group;
(12) a boron atom-containing group; and
(13) a group containing any of the groups (1) to (12).

(8) The method according to any one of (2) and (4) to (6), wherein the axially chiral isomer is represented by the general formula (II) below:

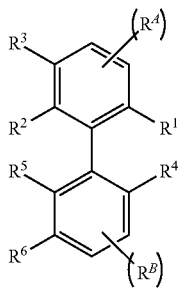

(II)

wherein
a bond between benzene rings represents an axis of chirality,
$R^1$ and $R^4$ each represents a group,
$R^2$ represents a group,
$R^3$ represents a hydrogen atom or a group,
or $R^2$ and $R^3$ may form a ring together,
$R^5$ represents a group,
$R^6$ represents a hydrogen atom or a group,
or $R^5$ and $R^6$ may form a ring together,
the two benzene rings may further have one or two $R^A$s and one or two $R^B$s that are bonded to an atom constituting each ring (wherein the one or two $R^A$s and the one or two $R^B$s each represent a group),
the groups are (a) a reactive group or (b) a substituent, and the reactive group exists only in any one of $R^1$ to $R^6$, $R^A$, and $R^B$.

(9) The method according to any one of (3) to (7), wherein the axially chiral isomer is represented by the general formula (II') below:

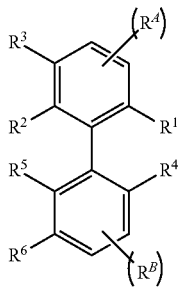

(II')

wherein
a bond between benzene rings represents an axis of chirality,
$R^1$ and $R^4$ each represent a group,
$R^2$ represents a group,
$R^3$ represents a hydrogen atom or a group,
or $R^2$ and $R^3$ may form a ring together,
$R^5$ represents a group,
$R^6$ represents a hydrogen atom or a group,
or $R^5$ and $R^6$ may form a ring together,
the two benzene rings may further have one or two $R^A$s and one or two $R^B$s that are bonded to an atom constituting each ring (wherein the one or two $R^A$s and the one or two $R^B$s each represent a group),
the groups are (a) a reactive group, (b) a group having a charged atom or a chargeable atom, or (c) a substituent,
the reactive group exists only in any one of $R^1$ to $R^6$, $R^A$, and $R^B$, and
when the group having a charged atom or a chargeable atom does not exist in any of $R^1$ to $R^6$, $R^A$, and $R^B$, at least one of the ring formed by $R^2$ and $R^3$ together and the ring formed by $R^5$ and $R^6$ together exists and represents a ring having a charged atom or a chargeable atom.

(10) The method according to any one of (3) to (7), wherein the axially chiral isomer is
a compound represented by the general formula (II-1) below:

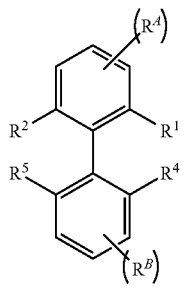

(II-1)

wherein
a bond between two benzene rings represents an axis of chirality,
$R^1$ represents a reactive group,
$R^4$ represents a group having a charged atom or a chargeable atom,
$R^2$ and $R^5$ each represent a substituent, and
the two benzene rings may further have one or two $R^A$s and one or two $R^B$s that are bonded to an atom constituting each ring (wherein the one or two $R^A$s and the one or two $R^B$s each represent a substituent); or
a compound represented by the general formula (II-2) below:

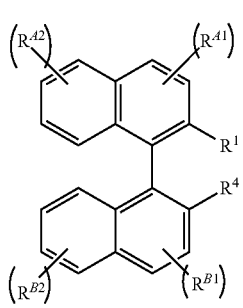

(II-2)

wherein
a bond between two naphthalene rings represents an axis of chirality,
$R^1$ represents a reactive group,
$R^4$ represents a group having a charged atom or a chargeable atom, and
the two naphthalene rings may further have one or two $R^{A1}$s and one to four $R^{A2}$s and one or two $R^{B1}$s and one to four $R^{B2}$s that are bonded to an atom constituting each ring (wherein the one or two $R^{A1}$s and the one to four $R^{A2}$s and the one or two $R^{B1}$s and the one to four $R^{B2}$s each represent a substituent).

(11) The method according to any one of (1) to (10), wherein the axially chiral compound is an R form.

(12) The method according to any one of (1) to (11), wherein the separation is performed by chromatography, electrophoresis, or ion mobility spectrometry.

(13) The method according to any one of (1) to (12), wherein the separation is performed by liquid chromatography using a hydrophobic column.

(14) The method according to any one of (1) to (13), wherein in separation, retention times of the first derivative and the second derivative are within 120 minutes.

(15) The method according to any one of (1) to (14), wherein the first compound and the second compound are a pair of enantiomers of a chiral compound selected from the group consisting of a chiral amino acid, a chiral amine, a chiral alcohol, a chiral carboxylic acid, and a chiral thiol.

(16) The method according to (15), wherein the chiral amino acid is one or more amino acids selected from the group consisting of alanine, valine, leucine, isoleucine, serine, threonine, cysteine, lysine, arginine, aspartic acid, glutamic acid, asparagine, glutamine, methionine, phenylalanine, tyrosine, tryptophan, histidine, and proline.

(17) The method according to (16), wherein the separation is performed so that resolution R represented by the mathematical formula below indicates a value of 0.5 or more:

$$R = \frac{1.18 \times |t_1 - t_2|}{W_1 + W_2}$$

wherein $t_1$ represents a retention time (min) of the first derivative, $t_2$ represents a retention time (min) of the second derivative, $W_1$ represents a peak width at half-height (min) of the first derivative, $W_2$ represents a peak width at half-height (min) of the second derivative, the denominator represents an absolute value, and R has a positive value.

(18) A compound represented by the general formula (I') below or a salt thereof:

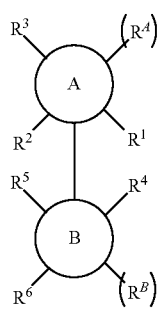

(I')

wherein
ring A and ring B each independently represent a benzene ring or a heteroaromatic ring,
a bond between the ring A and the ring B represents an axis of chirality,
$R^1$ represents a group bonded to one ring-constituting atom adjacent to a ring A-constituting atom bonded to the ring B,
$R^2$ represents a group bonded to the other ring-constituting atom adjacent to the ring A-constituting atom bonded to ring B,
$R^3$ represents a hydrogen atom or a group,
or $R^2$ and $R^3$ may form a ring together,
$R^4$ represents a group bonded to one ring-constituting atom adjacent to a ring B-constituting atom bonded to the ring A,
$R^5$ represents a group bonded to the other ring-constituting atom adjacent to the ring B-constituting atom bonded to the ring A,
$R^6$ represents a hydrogen atom or a group,
or $R^5$ and $R^6$ may form a ring together,
the rings A and B may further have one or two $R^A$s and one or two $R^B$s that are bonded to an atom constituting each ring (wherein the one or two $R^A$s and the one or two $R^B$s each represent a group),
the groups are (a') a group represented by the general formula (i), a group represented by the general formula (ii), or a group containing the group represented by the general formula (i) or (ii), (b) a group having a charged atom or a chargeable atom, or (c) a substituent,
(a') the group represented by the general formula (i), the group represented by the general formula (ii), or the group containing the group represented by general formula (i) or (ii) exists only in any one of $R^1$ to $R^6$, $R^A$, and $R^B$,
at least one of $R^1$ to $R^6$, $R^A$, and $R^B$ is the group having a charged atom or a chargeable atom,
the group having a charged atom or a chargeable atom is a di($C_1$ to $C_6$ alkyl)amino group, a tri($C_1$ to $C_6$ alkyl)ammonio group, a piperidino group, a morpholino group, or a group represented by the general formula (d1) or the general formula (d2),
the general formula (i) is as below:

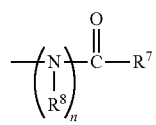

(i)

wherein
$R^7$ represents a hydroxy group or a leaving group (wherein the leaving group is selected from the group consisting of $C_1$ to $C_6$ alkylcarbonyloxy, a halogen atom, succinimidooxy, phenyloxy having an electron-withdrawing group, imidazolyl, and triazolyl),
n represents 0 or 1,
$R^8$ does not exist when n is 0, and
$R^8$ represents a hydrogen atom or a $C_1$ to $C_6$ alkyl group when n is 1,
the general formula (ii) is as below:

(ii)

wherein $R^9$ and $R^{10}$ each independently represent a hydrogen atom or a $C_1$ to $C_6$ alkyl group, the general formula (d1) is as below:

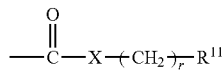
(d1)

wherein

X represents a nitrogen atom or an oxygen atom, r represents an integer of 0 to 10, $R^{11}$ represents a substituent having a positively charged nitrogen atom or a substituent having an uncharged nitrogen atom, and the general formula (d2) is as below:

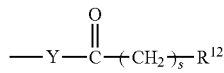
(d2)

wherein

Y represents a nitrogen atom or an oxygen atom, s represents an integer of 0 to 10, $R^{12}$ represents a substituent having a positively charged nitrogen atom or a substituent having an uncharged nitrogen atom.

(19) A compound represented by the general formula (I″) below, a salt thereof, or a mixture thereof:

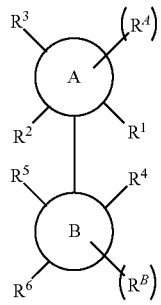
(I″)

wherein ring A and ring B each independently represent a benzene ring or a six-membered heteroaromatic ring, a bond between the ring A and the ring B represents an axis of chirality, $R^1$ represents a group bonded to one ring-constituting atom adjacent to a ring A-constituting atom bonded to the ring B, $R^2$ represents a group bonded to the other ring-constituting atom adjacent to the ring A-constituting atom bonded to the ring B, $R^3$ represents a hydrogen atom or a group, or $R^2$ and $R^3$ may form a ring together, $R^4$ represents a group bonded to one ring-constituting atom adjacent to a ring B-constituting atom bonded to the ring A, $R^5$ represents a group bonded to the other ring-constituting atom adjacent to the ring B-constituting atom bonded to the ring A, $R^6$ represents a hydrogen atom or a group, or $R^5$ and $R^6$ may form a ring together, the ring A and the ring B may further have one or two $R^A$s and one or two $R^B$s that are bonded to an atom constituting each ring (wherein the one or two $R^A$s and the one or two $R^B$s each represent a group), the groups are (a″) a group represented by the general formula (i′), a group represented by the general formula (i″), a group represented by the general formula (ii′), or a group containing the group represented by the general formula (i′), (i″), or (ii′), (b) a group having a charged atom or a chargeable atom, or (c) a substituent, (a″) the group represented by the general formula (i′), the group represented by the general formula (i″), the group represented by the general formula (ii′), or the group containing the group represented by the general formula (i′), (i″), or (ii′) exists only in any one of $R^1$ to $R^6$, $R^A$, and $R^B$, when the group having a charged atom or a chargeable atom does not exist in any of $R^1$ to $R^6$, $R^A$, and $R^B$, at least one of the ring A and the ring B represents a heteroaromatic ring having a charged atom or a chargeable atom, or at least one of the ring formed by $R^2$ and $R^3$ together and the ring formed by $R^5$ and $R^6$ together exits and represents a ring having a charged atom or a chargeable atom, the general formula (i′) is as below:

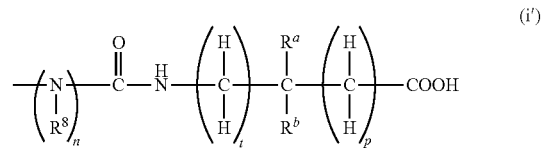
(i′)

wherein $R^a$ and $R^b$ each independently represent a group, different from each other, selected from the group consisting of a hydrogen atom, a halogen atom, hydroxy, sulfanyl, guanidino, formyl, carbamoyl, carbamoylamino, cyano, $C_1$ to $C_6$ alkyl optionally substituted with one to three substituents which are the same as or different from each other, phenyl optionally substituted with one to three substituents which are the same as or different from each other, and heteroaryl optionally substituted with one to three substituents which are the same as or different from each other (the substituent is an atom or a group selected from (i) to (iv) below, and the heteroaryl is a monocyclic or bicyclic nitrogen-containing heteroaromatic ring group:

(i) a halogen atom, hydroxy, sulfanyl, amino, guanidino, carboxy, formyl, carbamoyl, carbamoylamino, or cyano;

(ii) $C_1$ to $C_6$ alkyl, $C_1$ to $C_6$ alkyloxy, $C_1$ to $C_6$ alkylcarbonyl, $C_1$ to $C_6$ alkyloxycarbonyl, $C_1$ to $C_6$ alkylcarbonyloxy, $C_1$ to $C_6$ alkylthio, mono($C_1$ to $C_6$ alkyl)amino, or di($C_1$ to $C_6$ alkyl)amino (wherein these groups may be substituted with one to three substituents selected from the group consisting of a halogen atom, hydroxy, sulfanyl, amino, guanidino, carboxy, formyl, carbamoyl, carbamoylamino, and cyano);

(iii) phenyl, phenyloxy, phenylcarbonyl, phenyloxy carbonyl, phenylcarbonyloxy, phenylthio, monophenylamino, phenyl($C_1$ to $C_6$ alkyl)amino, or diphenylamino (wherein these groups may be substituted with one to three substituents selected from the group consisting of a halogen atom, hydroxy, sulfanyl, amino, guanidino, carboxy, formyl, carbamoyl, carbamoylamino, and cyano); and (iv) heteroaryloxy, heteroarylcarbonyl, heteroaryloxycarbonyl, heteroarylcarbonyloxy, heteroarylthio, monoheteroarylamino, N-heteroaryl-N—($C_1$ to $C_6$ alkyl)amino, N-heteroaryl-N-(phenyl)amino, or diheteroarylamino (wherein the heteroaryl is a monocyclic or bicyclic nitrogen-containing heteroaromatic ring group, and these groups may be substituted with one to three substituents selected from the group consisting of a halogen atom, hydroxy, sulfanyl, amino, guanidino, carboxy, formyl, carbamoyl, carbamoylamino, and cyano), n represents 0 or 1, $R^8$ does not exist when n is 0, $R^8$ represents a hydrogen atom or a $C_1$ to $C_6$ alkyl group when n is 1, t represents an integer of 0 to 3, and p represents an integer of 0 to 3), the general formula (i″) is as below:

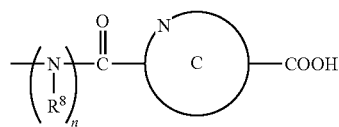

wherein ring C represents a five-membered or six-membered nitrogen-containing ring, n represents 0 or 1, $R^8$ does not exist when n is 0, and $R^8$ represents a hydrogen atom or a $C_1$ to $C_6$ alkyl group when n is 1, the general formula (ii′) is as below:

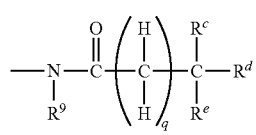

wherein $R^9$ represents a hydrogen atom or a $C_1$ to $C_6$ alkyl group, $R^c$, $R^d$, and $R^e$ each independently represent a hydrogen atom, a halogen atom, hydroxy, sulfanyl, guanidino, formyl, carbamoyl, carbamoylamino, cyano, $C_1$ to $C_6$ alkyl optionally substituted with one to three substituents which are the same as or different from each other, phenyl optionally substituted with one to three substituents which are the same as or different from each other, heteroaryl optionally substituted with one to three substituents which are the same as or different from each other (wherein the substituent is an atom or a group selected from the aforementioned (i) to (iv), and the heteroaryl is a monocyclic or bicyclic nitrogen-containing heteroaromatic ring group), or amino, and $R^c$, $R^d$, and $R^e$ are different from each other, and q represents an integer of 0 to 3, and the charged atom or the chargeable atom is a positively charged nitrogen atom or an uncharged nitrogen atom.

(20) The compound, the salt thereof, or the mixture thereof according to (19), wherein in the general formula (i′), $R^a$ represents a hydrogen atom, and $R^b$ represents methyl, 1-methylethyl, 2-methylpropyl, 1-methylpropyl, hydroxymethyl, 1-hydroxyethyl, sulfanylmethyl, 4-aminobutyl, 3-guanidinopropyl, carboxymethyl, 2-carboxyethyl, carbamoylmethyl, 2-carbamoylethyl, 2-(methylthio)ethyl, phenylmethyl, 4-hydroxyphenylmethyl, indolylmethyl, imidazolylmethyl, 3-aminopropyl, 3-(carbamoylamino)propyl, 2-hydroxyethyl, or 4-guanidinobutyl, and in the general formula (i″), the ring C is pyrrolidine.

Effect of Invention

According to the present invention, an enantiomer can be analyzed at high sensitivity in a short time with high resolution. The present invention has high general versatility, and also has an advantage in which a chiral compound such as a chiral amino acid can be comprehensively analyzed.

DETAILED DESCRIPTION OF THE PREFERRED EMBODIMENTS

The present invention provides a method for analyzing an enantiomer.

The enantiomer to be analyzed by the method of the present invention is an isomer having a chiral element. Examples of the chiral element may include an asymmetric atom (for example, asymmetric carbon atom), an axis of chirality, and a planar chirality. The enantiomer may have one or more (for example, two or three) chiral elements. The enantiomer has preferably one chiral element, more preferably one asymmetric atom, and further preferably one asymmetric carbon atom.

The enantiomer to be analyzed by the method of the present invention may be a small molecule (small substance). The term "small molecule" used herein refers to a compound having a molecular weight of less than 1,500. The small molecule may be a natural substance or a synthesized substance. The small molecule may have a molecular weight of less than 1,200, less than 1,000, less than 800, less than 700, less than 600, less than 500, less than 400, or less than 300. The small molecule may have a molecular weight of 50 or more, 60 or more, 70 or more, 80 or more, 90 or more, 100 or more, 120 or more, 150 or more, or 200 or more.

The enantiomer to be analyzed by the method of the present invention is an enantiomer that may be contained in any sample. Examples of such a sample may include biological samples derived from organisms, and non-biological samples such as a synthesized sample obtained by an organic synthesis reaction and an environment sample present in a natural environment. Examples of the organisms from which the biological samples are derived may include animals such as mammals (for example, human, monkey, mouse, rat, rabbit, cattle, pig, horse, gorgonian, and sheep), and birds, insects, mollusks, microorganisms, and plants. The organisms are preferably mammals. Examples of the biological sample may include blood samples (for example, whole blood, serum, and plasma), saliva, urine, feces, bile, sweat, tear, cerebrospinal fluid, and tissue and cell extracts. Examples of the synthesized sample may include reaction products obtained by an organic synthesis reaction to obtain a chiral compound. Examples of the environment sample may include samples derived from soil, stone, meteorite, seawater, and fresh water.

The method of the present invention includes the following (1) to (3):

(1) reacting a mixture of a first compound and a second compound that are a pair of enantiomers with an axially chiral compound that is one of a pair of axially chiral isomers, to generate a derivative mixture containing a first derivative and a second derivative, the first derivative obtained by a reaction of the first compound with the axially chiral compound, and the second derivative obtained by a reaction of the second compound with the axially chiral compound;

(2) separating the first derivative and the second derivative in the derivative mixture; and (3) detecting the separated first derivative and second derivative by mass spectrometry.

Step (1)

In this step, the mixture of the first compound and the second compound is reacted with the axially chiral compound. By this reaction, the derivative mixture containing the first derivative and the second derivative is produced. The first compound and the second compound are a pair of enantiomers. The axially chiral compound is one of a pair of axially chiral isomers. The first derivative is a derivative obtained by the reaction of the first compound with the axially chiral compound. The second derivative is a derivative obtained by the reaction of the second compound with the axially chiral compound.

The mixture used in the step (1) is a sample containing the first compound and the second compound that are a pair of enantiomers. Derivation of the mixture is not particularly limited. For example, the biological sample or non-biological sample described above can be used as the mixture. The number of units of the "pair of enantiomers" contained in the mixture varies depending on the kind of the sample, and is one or more (for example, 2, 3, 4, 5, 10, 15, 20, 25, or 30 or more). The ratio of the amount of the first compound to the amount of the second compound in the sample (amount of first compound/amount of second compound) is not particularly limited, and for example, may be 1/1,000 or more, 1/100 or more, or 1/10 or more. For example, this ratio may be 1,000 or less, 100 or less, or 10 or less.

The mixture used in the step (1) may be pre-treated before the step (1). Examples of the pre-treatment may include centrifugation, extraction, filtration, precipitation, an affinity treatment, heating, dilution, concentration, deproteinization, and freezing. The first compound and the second compound that are the pair of enantiomers may be subjected to the step (1) without purification or after purification.

First Compound and Second Compound that are a Pair of Enantiomers

The first compound and the second compound have a relationship between a pair of enantiomers. The first compound and the second compound may have the same chemical structure except for chirality. The first compound and the second compound used in the method of the present invention are not particularly limited as long as they are reacted with the axially chiral compound used. The first compound and the second compound can be appropriately selected. For facilitation of reaction with the axially chiral compound, the first compound and the second compound are preferably a pair of enantiomers having a predetermined functional group with high reactivity. Examples of such a functional group may include amino, carboxyl, hydroxy, sulfanyl (thiol), haloformyl, aldehyde, ketone, and alkyl halide.

Specific examples of the first compound and the second compound that can be analyzed by the method of the present invention and are the pair of enantiomers may include chiral compounds selected from the group consisting of chiral amino acids, chiral carboxylic acids, chiral amines, chiral alcohols, chiral aldehydes, chiral ketones, chiral thiols, and chiral alkyl halides, and salts thereof. Examples of the salts may include metal salts (for example, monovalent metal salts such as sodium salts and potassium salts, and divalent metal salts such as calcium salts and magnesium salts), inorganic salts (for example, salts of halides such as a fluoride, a chloride, a bromide, and an iodide, and ammonium salts), organic salts (for example, ammonium salts substituted with an alkyl group), and acid addition salts (for example, salts with inorganic acids such as sulfuric acid, hydrochloric acid, hydrobromic acid, nitric acid, and phosphoric acid, and salts with organic acids such as acetic acid, oxalic acid, lactic acid, citric acid, trifluoromethanesulfonic acid, and trifluoroacetic acid). The first compound and the second compound that are the pair of enantiomers may be a natural compound or an unnatural compound (for example, synthesized compound).

Examples of chiral amino acids that can be analyzed by the method of the present invention may include chiral α-amino acids (for example, alanine, valine, leucine, isoleucine, serine, threonine, cysteine, lysine, arginine, aspartic acid, glutamic acid, asparagine, glutamine, methionine, phenylalanine, tyrosine, tryptophan, histidine, proline, allothreonine, alloisoleucine, homoserine, homoarginine, homocysteine, citrulline, selenocysteine, ornithine, pyrrolysine, hydroxyproline, hydroxylysine, α-aminobutyric acid, thyroxine, DOPA, phosphoserine, 2-phenylglycine, theanine, kainic acid, ibotenic acid, tricholomic acid, azetidine-2-carboxylic acid, 2-amino-4-bromobutyric acid, 2-allylglycine, 2-cyclohexyiglycine, and cystine), chiral β-amino acids (for example, 3-amino-3-phenylpropionic acid, 3-aminoisobutyric acid, 3-aminobutyric acid, 2-aminocyclohexanecarboxylic acid, and β-phenylalanine), and chiral γ-amino acids (for example, statin, and 3-aminocyclohexanecarboxylic acid).

Examples of chiral carboxylic acids that can be analyzed by the method of the present invention may include lactic acid, malic acid, isocitric acid, oxasuccinic acid, phosphogluconic acid, glyceric acid, 3-hydroxyisobutyric acid, mandelic acid, tartaric acid, 2-methylbutyric acid, 2-bromopropionic acid, 2-bromoisovaleric acid, 2-chioroisovaleric acid, 2-hydroxy-4-phthalimidebutyric acid, methylglutaric acid, α-methoxy-α-methyl-1-naphthaleneacetic acid, and ascorbic acid.

Examples of chiral amines that can be analyzed by the method of the present invention may include glucosamine, galactosamine, alaninol, isoleucinol, noradrenaline, epinephrine, amfetamine, methamphetamine, methylenedioxymethamphetamine, bupropion, ephedrine, α-methyltryptamine, and cyclohexanediamine.

Examples of chiral alcohols that can be analyzed by the method of the present invention may include 2-butanol, 1,2-butanediol, 1,3-butanediol, 2,3-butanediol, 3-butyn-2-ol, α-hydroxy-γ-butyrolactone, 2-octanol, 1-(2-naphthyl) ethanol, 1-phenylethylalcohol, α-tetralol, glycidol, glucose, allose, mannose, galactose, ribose, deoxyribose, xylose, erythrose, threose, glyceraldehyde, fructose, ribulose, erythrulose, sucrose, ascorbic acid, adenosine, guanosine, uridine, cytidine, and methyl mandelate.

Examples of chiral aldehydes that can be analyzed by the method of the present invention may include glyceraldehyde, citronellal, glucose, allose, mannose, galactose, ribose, and deoxyribose.

Examples of chiral ketones that can be analyzed by the method of the present invention may include muscone, menthone, camphor, fenchone, thujone, pulegone, carvone, verbenone, jasmonic acid, and fructose.

Examples of chiral thiols that can be analyzed by the method of the present invention may include N-acetyl-L- cysteine, glutathione, thiolactic acid, 10-mercaptoborneol, 10-mercaptoisoborneol, thiomalic acid, captopril, and N-isobutyrylcysteine.

The first compound and the second compound that can be analyzed by the method of the present invention may be pre-reacted to enhance the reactivity with the axially chiral compound. When the first compound and the second compound are, for example, a chiral carboxylic acid (D form and L form), a carboxyl group in the chiral carboxylic acid may be converted into a "carbonyl group having a leaving group" described below, or the chiral carboxylic acid may be converted into an anhydride, which can be obtained by dehydration. A converted compound having a carbonyl group having a leaving group or a converted compound that is the anhydride may be favorably reacted with an axially chiral compound having an amino group.

When the first compound and the second compound that can be analyzed by the method of the present invention and the axially chiral compound have the same reactive group, the reactive groups in the first compound and the second compound may be protected to specifically react the first compound and the second compound with the axially chiral compound. For example, when the first compound and the second compound are a chiral amino acid having an amino group and a carboxyl group and the axially chiral compound has an amino group that is the reactive group as described below, the carboxyl group of the chiral amino acid can be specifically reacted with the amino group of the axially chiral compound by protecting the amino group in the first compound and the second compound.

Axially Chiral Compound

The axially chiral compound used in the present invention is one (i.e., one of R form or S form) of a pair of axially chiral isomers (i.e., combination of R form and S form).

The axially chiral isomers are a compound having an axis of chirality. Examples of the axis of chirality may include an axis of covalent bond between two rings (for example, covalent bond between carbon atoms) (i.e., axis of chirality of atropisomer), an axis of double bond formed by allene (basic structure having two coupled double bonds), and an axis based on a Spiro ring (quaternary spiro carbon atom). The axis of chirality is preferably an axis of a covalent bond between two rings. Such an axis of a covalent bond is preferably a single bond. It is preferable that the axially chiral isomers each have only one axis of chirality, which is a chiral element. Therefore, the axially chiral isomers are preferably a compound having two rings (ring A and ring B) as described below. The chiral element of this compound is only an axis of covalent bond that crosslinks the two rings (preferably an axis of a single bond between carbon atoms).

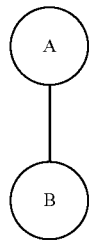

The two rings of each of the axially chiral isomers may be the same or different. It is preferable that the two rings are the same from the viewpoint of synthesis and easy avail-ability. The rings are a benzene ring, a heteroaromatic ring, or a condensed ring of a benzene ring or a heteroaromatic ring with another ring.

The term "heteroaromatic ring" used herein means a five- or six-membered heteroaromatic ring that has one or two heteroatoms (for example, nitrogen atom, oxygen atom, and sulfur atom) as a ring-constituting atom in addition to a carbon atom and in which the number of atoms constituting the ring is five or six, respectively. The heteroaromatic ring is preferably a six-membered heteroaromatic ring. Examples of the six-membered heteroaromatic ring may include as follows.

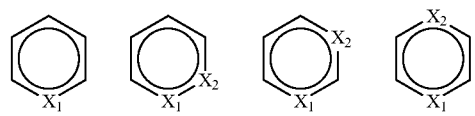

($X_1$ and $X_2$ (if they are present) each independently represent a nitrogen atom, an oxygen atom, or a sulfur atom. A solid line circle in the ring represents that the ring has aromaticity. Crosslinking is formed on a carbon atom or a nitrogen atom (if $X_1$ and/or $X_2$ is a nitrogen atom) that is the ring-constituting atom, and preferably on the carbon atom.)

Specific examples of the six-membered heteroaromatic ring may include six-membered nitrogen-containing heteroaromatic rings (for example, pyridine, pyridazine, pyrimidine, and pyrazine), six-membered oxygen-containing heteroaromatic rings (for example, pyrylium), and six-membered sulfur-containing heteroaromatic rings (for example, thiopyrlium).

Examples of the other ring used for formation of the condensed ring may include five- to seven-membered aromatic or non-aromatic rings. The other ring is preferably a five- or six-membered aromatic or non-aromatic ring. Specific examples of the five- or six-membered aromatic or non-aromatic ring may include as follows.

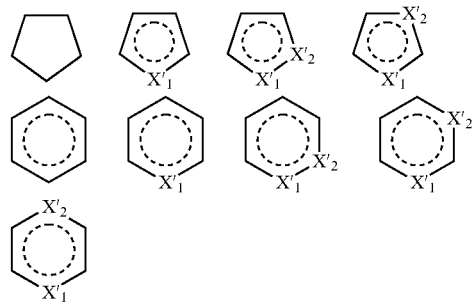

($X'_1$ and $X'_2$ (if they are present) each independently represent a nitrogen atom, an oxygen atom, or a sulfur atom. A dotted line circle in the ring represents that the ring has aromaticity or non-aromaticity.)

Specific examples of the five- or six-membered aromatic or non-aromatic ring may include five-membered heteroaromatic rings (for example, pyrrole, furan, thiophene, pyrazole, isoxazole, isothiazole, imidazole, oxazole, and thiazole), five-membered non-aromatic rings (for example, cyclopentane, pyrrolidine, imidazolidine, oxolane, and dioxolane), six-membered aromatic rings (for example, benzene, and the six-membered heteroaromatic rings described above) and six-membered non-aromatic rings (for example, cyclohexane, piperidine, piperazine, oxane, and dioxane).

The condensed ring of a benzene ring or a heteroaromatic ring with the other ring is a polycyclic condensed ring obtained by condensation of the benzene ring or heteroaromatic ring with the other ring described above. A ring-constituting part that is shared by the two rings and is a condensed part of the polycyclic condensed ring is a bonding part between carbon atoms. A part that contains a nitrogen atom, an oxygen atom, or a sulfur atom is not shared by the two rings as a condensed part. The polycyclic condensed ring is preferably a bicyclic or tricyclic condensed ring, and more preferably a bicyclic condensed ring. The polycyclic condensed ring is preferably a polycyclic aromatic ring. The polycyclic condensed ring is particularly preferably a bicyclic aromatic ring. Examples of the bicyclic aromatic ring may include naphthalene, indole, benzopyrazole, benzisoxazole, benzisothiazole, benzimidazole, benzoxazole, benzothiazole, quinoline, isoquinoline, cinnoline, phthalazine, quinazole, quinoxaline, pteridine, and purine.

When the axially chiral isomers each have an axis of a covalent bond between the two rings as an axis of chirality, it is necessary that free rotation of the axially chiral compound that is one of the axially chiral isomers with respect to the axis of chirality as a rotation axis be restricted from the viewpoint of maintenance of chirality. The free rotation can be restricted by introduction of substituent into the axially chiral isomer or use of the aforementioned condensed ring as the ring. Specifically, the free rotation can be restricted by substituting hydrogen atoms bonded to ring-constituting atoms (two ring-constituting atoms adjacent to one ring-constituting atom used for crosslinking in the ring A and two ring-constituting atoms adjacent to one ring-constituting atom used for crosslinking in the ring B: four ring-constituting atoms in total (hereinafter sometimes simply referred to as "adjacent atoms")) adjacent to each of ring-constituting atoms used for crosslinking in the two rings (ring A and ring B) (one ring-constituting atom in the ring A and one ring-constituting atom in the ring B) with an atom or group that is larger than the hydrogen atoms, or by using the adjacent atoms for condensation with the other ring. When the hydrogen atoms bonded to the four adjacent atoms are substituted with an atom or group that is larger than the hydrogen atoms, for example, with another atom (for example, halogen atom) or a methyl group (the smallest alkyl group), the free rotation can be restricted. This has been known. When the adjacent atoms are used for condensation with the other ring, the free rotation can be restricted. This has also been known. Accordingly, in the method of the present invention, such an axially chiral isomer is used as an axially chiral isomer having an axis of a covalent bond between two rings that is an axis of chirality.

The axially chiral isomers preferably have hydrophobicity. "Hydrophobicity" means that a substance is insoluble in water or has low solubility in water.

In the present invention, the first derivative and/or the second derivative can be detected by mass spectrometry as long as the first derivative and/or the second derivative, which are produced by a reaction of the first compound and/or the second compound with the axially chiral compound, contain a charged atom or a chargeable atom. Therefore, the first compound and/or the second compound can be detected by mass spectrometry. Accordingly, when the axially chiral compound used in the present invention contains a charged atom or a chargeable atom, the first compound and/or the second compound that can be analyzed by the method of the present invention may not contain the charged atom or the chargeable atom. In contrast, when the axially chiral compound used in the present invention does not contain a charged atom or a chargeable atom, it is necessary that the first compound and/or the second compound contain the charged atom or the chargeable atom.

The term "charged atom" used herein refers to a positively or negatively charged atom. Examples of a positively charged atom may include positively charged nitrogen and phosphorus atoms. Examples of a negatively charged atom may include negatively charged oxygen, boron, and sulfur atoms. When the axially chiral compound is one of a pair of axially chiral isomers containing a charged atom, ionization can be omitted in mass spectrometry used for detection of the first derivative and the second derivative that are obtained by a reaction of the first compound and the second compound with the axially chiral compound. The charged atom is preferably a positively charged atom, and more preferably a positively charged nitrogen atom.

The term "chargeable atom" used herein refers to an uncharged atom that may be charged by ionization. Specifically, the chargeable atom is in an uncharged state during use as the axially chiral compound. In mass spectrometry used for detection of the first derivative and the second derivative that are obtained by a reaction of the first compound and the second compound with the axially chiral compound, the chargeable atom is ionized, and as a result, positively or negatively charged. Examples of the chargeable atom may include uncharged atoms that are positively chargeable (for example, uncharged nitrogen atom and uncharged phosphorus atom), and uncharged atoms that are negatively chargeable (for example, uncharged oxygen atom, uncharged boron atom, and uncharged sulfur atom). When the axially chiral compound is one of a pair of axially chiral isomers containing the chargeable atom, there is a need for ionization of the chargeable atom in mass spectrometry. The chargeable atom is preferably an uncharged atom that is positively chargeable, and more preferably an uncharged nitrogen atom.

When the charged atom or the chargeable atom is contained in the axially chiral compound, the charged atom or the chargeable atom may be contained as a ring-constituting atom in one or both of the two rings of the axially chiral compound. When the charged atom or the chargeable atom is contained as the ring-constituting atom, one or both of the two rings are a heteroaromatic ring or a condensed ring thereof. Alternatively, the charged atom or the chargeable atom may not be contained as the ring-constituting atom. In this case, one or both of the two rings contain a group containing the charged atom or the chargeable atom. The group containing the charged atom or the chargeable atom is used in substitution of the hydrogen atoms bonded to the adjacent atoms described above, and the free rotation can be restricted. The first compound and the second compound that can be analyzed by the method of the present invention may contain the charged atom or the chargeable atom as a constituent atom. Examples of such compounds may include lysine, arginine, homoarginine, histidine, cysteic acid, and nucleic acid.

Examples and preferable examples of the term "charged atom or chargeable atom" in the "group containing the charged atom or the chargeable atom" are as described above. Examples of the group containing the charged atom or the chargeable atom may include the following groups (1) to (13):

(1) an optionally substituted amino group (for example, an unsubstituted amino group and an amino group having a substituent);

(2) an optionally substituted ammonio group (for example, an unsubstituted ammonio group and an ammonio group having a substituent);

(3) an optionally substituted guanidino group (for example, an unsubstituted guanidino group and a guanidino group having a substituent);

(4) an optionally substituted guanidium group (for example, an unsubstituted guanidium group and a guanidium group having a substituent);

(5) an optionally substituted imino group (for example, an unsubstituted imino group and an imino group having a substituent);

(6) an optionally substituted iminium group (for example, an unsubstituted iminium group and an iminium group having a substituent);

(7) an optionally substituted nitrogen-containing ring group (for example, an unsubstituted nitrogen-containing ring group and a nitrogen-containing ring group having a substituent);

(8) an optionally substituted phosphino group (for example, an unsubstituted phosphino group and a phosphino group having a substituent);

(9) an optionally substituted phosphonio group (for example, an unsubstituted phosphonio group and a phosphonio group having a substituent);

(10) an optionally substituted oxy group (for example, a hydroxy group and an oxy group having a substituent);

(11) an optionally substituted thio group (for example, a sulfonyl group (sulfonic acid group), a sulfanyl group (thiol group), and a thio group having a substituent);

(12) a boron-containing group; and

(13) a group containing any of the groups (1) to (12).

Examples of a nitrogen-containing ring of the nitrogen-containing ring group (7) described above may include five-membered nitrogen-containing heteroaromatic rings (for example, pyrrole, pyrazole, and imidazole), the six-membered nitrogen-containing heteroaromatic rings described above, five-membered nitrogen-containing hetero non-aromatic rings (for example, pyrrolidine and imidazolidine), and six-membered nitrogen-containing hetero non-aromatic rings (for example, piperidine, piperazine, and morpholine). The nitrogen-containing ring is preferably a six-membered nitrogen-containing heteroaromatic ring.

In the group (12) described above, the boron-containing group refers to a monovalent group containing a negatively charged boron atom or an uncharged boron atom.

Examples of the monovalent group containing a negatively charged boron atom may include a group represented by the following formula.

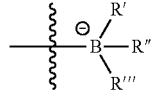

(wherein R', R", and R''' each independently represent a hydrogen atom, a halogen atom, $C_1$ to $C_6$ alkyl optionally substituted with one to five substituents which are the same as or different from each other, phenyl optionally substituted with one to five substituents which are the same as or different from each other, or a heteroaromatic ring optionally substituted with one to five substituents which are the same as or different from each other. Details of the $C_1$ to $C_6$ alkyl, heteroaromatic ring, and substituents are as described below.)

Preferable examples of the monovalent group containing a negatively charged boron atom may include as follows.

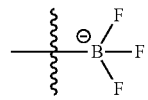

Examples of the monovalent group containing an uncharged boron atom may include groups represented by the following formula.

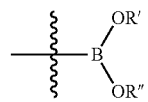

(Wherein R' and R" each independently represent a hydrogen atom, $C_1$ to $C_6$ alkyl optionally substituted with one to five substituents which are the same as or different from each other, phenyl optionally substituted with one to five substituents which are the same as or different from each other, or a heteroaromatic ring optionally substituted with one to five substituents which are the same as or different from each other. Details of the $C_1$ to $C_6$ alkyl, heteroaromatic ring, and substituents are as described below.)

Specifically, preferable examples of the monovalent group containing an uncharged boron atom may include as follows.

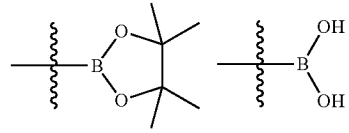

A predetermined group containing a specific atom or group (for example, the group containing the charged atom or the chargeable atom described above, the group containing any group of (1) to (12) described above, and a group containing a reactive group described below) used herein means that the predetermined group contains the specific atom or group with a linker interposed therebetween. Even when the specific atom or group is present with the linker interposed between the atom or group and the predetermined group, a desired effect to be obtained by the specific atom or group is exerted. Therefore, the predetermined group containing the specific atom or group is also to be considered. The linker can be represented by the formula: $-(L)_m-$ (wherein L is a repeatable unit, and m is an integer of 1 to 10).

Examples of the repeatable unit represented by L may include a minimum unit constituting a chain including a carbon atom, a hydrogen atom, an oxygen atom, a nitrogen atom, and a sulfur atom. Examples of the minimum unit may include units represented by the following formulae.

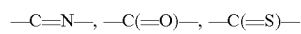

(wherein R' and R" are each independently a hydrogen atom or a substituent.)

Preferable examples of the repeatable unit represented by L may include general-purpose units represented by the following formulae.

—CH$_2$—, —O—, —NH—, —CH=CH—,

—C(=O)—

Since the repeatable unit represented by L is the minimum unit, the linker may naturally have a predetermined group constituted by a combination of the minimum unit (for example, an ester group constituted by a combination of —C(=O)— and —O— and an amido group constituted by a combination of —C(=O)— and —NH—).

m is an integer of 1 to 10, preferably an integer of 1 to 5, and more preferably an integer of 1 to 3.

Examples of the substituent in (1) to (13) described above may include as follows.

Among the examples described above, the group containing the charged atom or the chargeable atom is preferably di($C_1$ to $C_6$ alkyl)amino (more preferably dimethylamino or diethylamino), tri($C_1$ to $C_6$ alkyl)ammonio, a piperidino group, a morpholino group, or a group represented by the general formula (d1) or a group represented by the general formula (d2).

Herein, the group represented by the general formula (d1) is as follows.

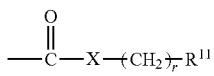

(d1)

(wherein
X represents a nitrogen atom or an oxygen atom,
r represents an integer of 0 to 10, and
$R^{11}$ represents a substituent having a positively charged nitrogen atom or a substituent having an uncharged nitrogen atom.)

X is preferably a nitrogen atom.

r is preferably an integer of 0 to 5, more preferably an integer of 0 to 3, and further preferably 0, 1, or 2.

The term "substituent having a positively charged nitrogen atom" used herein refers to a substituent that contains a positively charged nitrogen atom as a constituent atom. The term "substituent having an uncharged nitrogen atom" refers to a substituent that contains an uncharged nitrogen atom as a constituent atom. The substituent having a positively charged nitrogen atom or the substituent having an uncharged nitrogen atom includes a group containing a positively charged nitrogen atom or an uncharged nitrogen atom among the groups (1) to (13) that are the examples of the group containing the charged atom or the chargeable atom. Specific examples of the substituent having a positively charged nitrogen atom or the substituent having an uncharged nitrogen atom may include the aforementioned groups (1) to (7) and a group containing any of the aforementioned groups (1) to (7).

The substituent having a positively charged nitrogen atom or the substituent having an uncharged nitrogen atom that is represented by $R^{11}$ is preferably the aforementioned group (1) to (7) or a group containing any the aforementioned groups (1) to (7), more preferably the aforementioned group (1), (2), or (7), or a group containing the aforementioned group (1), (2), or (7), and further preferably the aforementioned group (1), (2), or (7).

The group (1) represented by $R^{11}$ is preferably di($C_1$ to $C_6$ alkyl)amino. Definition, examples, and preferable examples of $C_1$ to $C_6$ alkyl are as described below.

The group (2) represented by $R^{11}$ is preferably tri($C_1$ to $C_6$ alkyl)ammonio. The definition, examples, and preferable examples of $C_1$ to $C_6$ alkyl are as described below.

The group (7) represented by $R^{11}$ is preferably an optionally substituted monocyclic or bicyclic nitrogen-containing heteroaromatic ring. Examples of the monocyclic nitrogen-containing heteroaromatic ring may include groups of "five-membered nitrogen-containing heteroaromatic ring" and "six-membered nitrogen-containing heteroaromatic ring" described below. Examples of the bicyclic nitrogen-containing heteroaromatic ring may include groups of "bicyclic nitrogen-containing heteroaromatic ring" described below. The group (7) represented by $R^{11}$ is more preferably a monocyclic nitrogen-containing heteroaromatic ring, and further preferably optionally substituted pyridyl (for example, 2-pyridyl, 3-pyridyl, and 4-pyridyl).

Examples of the group represented by the general formula (d2) may include as follows.

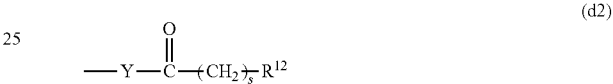

(d2)

(wherein
Y represents a nitrogen atom or an oxygen atom,
s represents an integer of 0 to 10, and
$R^{12}$ represents a substituent having a positively charged nitrogen atom or a substituent having an uncharged nitrogen atom.)

Y is preferably a nitrogen atom.

s is preferably an integer of 0 to 5, more preferably an integer of 0 to 3, and further preferably 0, 1, or 2.

Examples and preferable examples of the "substituent having a positively charged nitrogen atom or substituent having an uncharged nitrogen atom" represented by $R^{12}$ are the same as those of the "substituent having a positively charged nitrogen atom or substituent having an uncharged nitrogen atom" represented by $R^{11}$.

The axially chiral compound used in the present invention is not particularly limited as long as it is reacted with the first compound and the second compound that are a pair of enantiomers. For facilitation of reaction with the first compound and the second compound, the axially chiral compound may have a predetermined reactive group with high reactivity.

The term "reactive group" used herein includes a nucleophilic group, an electrophilic group, or a group containing at least one of a nucleophilic group or an electrophilic group. For example, an axially chiral compound having an electrophilic group is favorably reacted with an amino group, a hydroxyl group, and a thiol group (sulfanyl group). Therefore, the axially chiral compound having an electrophilic group is useful in analysis of chiral amino acids, chiral amines, chiral alcohols, and chiral thiols. An axially chiral compound having a nucleophilic group is favorably reacted with a carboxyl group. Therefore, the axially chiral compound having a nucleophilic group is useful in analysis of chiral amino acids and chiral carboxylic acids. The reactive group is preferably a group represented by the general formula (i), a group represented by the general formula (ii), or a group containing a group represented by the general formula (i) or (ii), as described below.

The term "nucleophilic group" used herein refers to an electron donating group used in a nucleophilic reaction. Examples of the nucleophilic group may include amino, hydrazino, sulfanyl, and hydroxy.

The term "electrophilic group" used herein refers to an electron accepting group used in an electrophilic reaction. Examples of the electrophilic group may include carboxyl, a carbonyl group having a leaving group, maleimide, acryloylamino, methacryloylamino, formyl, ketone, aldehyde, isocyanato, isothiocyanato, and a halogen atom (for example, fluorine atom).

Examples of the "leaving group" used herein may include alkyloxy (preferably $C_1$ to $C_6$ alkyloxy described below), alkylcarbonyloxy (preferably $C_1$ to $C_6$ alkylcarbonyloxy described below), a halogen atom (for example, a fluorine atom, a chlorine atom, a bromine atom, and an iodine atom), succinimidooxy, phenyloxy having an electron withdrawing group (for example, nitrophenyloxy, cyanophenyloxy, pentafluorophenyloxy, trichlorophenyloxy, tetrachlorophenyloxy, pentachlorophenyloxy, acetylphenyloxy, trifluoromethylphenyloxy, and methylsulfonylphenyloxy), imidazolyl, and triazolyl. A carbonyl group having the leaving group can act as a carbonyl group having a positively charged carbon atom (i.e., active carbonyl group).

The leaving group is preferably $C_1$ to $C_6$ alkyloxy, $C_1$ to $C_6$ alkylcarbonyloxy, a halogen atom, succinimidooxy, phenyloxy having an electron withdrawing group, imidazolyl, or triazolyl, more preferably $C_1$ to $C_6$ alkylcarbonyloxy, a halogen atom, succinimidooxy, phenyloxy having an electron withdrawing group, imidazolyl, or triazolyl, and further preferably a halogen atom, succinimidooxy, or phenyloxy having an electron withdrawing group. The halogen atom that is the leaving group is preferably a chlorine atom. The phenyloxy having an electron withdrawing group that is the leaving group is preferably nitrophenyloxy, and more preferably p-nitrophenyloxy.

The group containing at least one of the nucleophilic group and the electrophilic group is a group having at least one of the nucleophilic group and the electrophilic group and a part other than the group. Examples of the part may include alkyl and phenyl. An axially chiral compound having such a group can be favorably reacted with the first compound and the second compound.

The axially chiral compound preferably has one reactive group as described above. When the axially chiral compound has a plurality of reactive groups, a plurality of first derivatives and a plurality of second derivatives are produced by a reaction of the first compound and the second compound with the axially chiral compound. This is due to the presence of the plurality of reactive groups. In this case, the analysis of the pair of enantiomers requires comprehensive detection of the plurality of first derivatives and the plurality of second derivatives. Therefore, the analysis is complex. When the axially chiral compound has one reactive group, one first derivative and one second derivative that have a diastereomeric relationship are produced by a reaction of the first compound and the second compound that are the pair of enantiomers with the axially chiral compound. Therefore, the analysis of the pair of enantiomers can be facilitated.

Reaction of First Compound and Second Compound with Axially Chiral Compound

The reaction of the first compound and the second compound with the axially chiral compound can be performed by a publicly known method. For example, the reaction can be performed by appropriately setting a reaction condition such as a solvent, a temperature, a time, and a reagent.

It is preferable that the reaction is performed so that from the first compound and the second compound that are the pair of enantiomers, one kind of first derivative and one kind of second derivative that have a diastereomeric relationship can be obtained. This is because the detection of only the one kind of first derivative and the one kind of second derivative can facilitate the analysis of the pair of enantiomers.

Therefore, it is preferable that the reaction is performed under a gentle reaction condition in which the chirality (R form or S form) of the axially chiral compound that is one of the pair of axially chiral isomers is maintained. When the reaction is performed under a severe reaction condition in which the chirality of the axially chiral compound cannot be maintained (for example, under a high-temperature and high-pressure condition), the axis of chirality in which the free rotation is restricted may be energetically rotated. As a result, a mixture of the R form and the S form may be produced. When there is the mixture of the R form and the S form, the mixture (R form and S form) of the axially chiral compound may be reacted with the first compound and the second compound by the reaction, to produce at least two kinds of first derivatives ((R)-first derivative obtained by a reaction of the first compound with the axially chiral compound of R form and (S)-first derivative obtained by a reaction of the first compound with the axially chiral compound of S form), and at least two kinds of second derivatives ((R)-second derivative obtained by a reaction of the second compound with the axially chiral compound of R form and (S)-second derivative obtained by a reaction of the second compound with the axially chiral compound of S form). In this case, the analysis of the pair of enantiomers requires comprehensive detection of the two kinds of first derivatives and the two kinds of second derivatives. Therefore, the analysis is complex. When the reaction is performed under the condition in which the chirality of the axially chiral compound is maintained, the first compound and the second compound that are the pair of enantiomers are reacted with the axially chiral compound, to produce one kind of first derivative and one kind of second derivative that have a diastereomeric relationship. Therefore, the analysis of the pair of enantiomers can be facilitated.

The gentle reaction condition in which the chirality of the axially chiral compound is maintained varies depending on the kind of axially chiral compound. Examples thereof may include an atmospheric pressure and a temperature of 100° C. or lower.

The derivative mixture obtained by the reaction may be subjected to a predetermined treatment after the reaction and before the step (2). Examples of the treatment may include centrifugation, extraction, filtration, precipitation, an affinity treatment, heating, concentration, dilution, and freezing.

Step (2)

In this step, the first derivative and the second derivative in the derivative mixture are separated. During use of mass spectrometry, a substance to be detected can be generally separated from another substance at a mass spectrometry part as long as the substance has a mass-to-charge ratio different from the other substance. Therefore, the separation is not necessarily performed. However, in the method of the present invention, the separation of the first derivative and the second derivative is necessary. This is because the mass-to-charge ratios of the first compound and the second compound that are the pair of enantiomers are the same.

The separation can be performed by any separation method capable of separating the first derivative and the second derivative. Examples of the separation method may include chromatography such as liquid chromatography, supercritical fluid chromatography, gas chromatography, and thin layer chromatography, electrophoresis, ion mobility spectroscopy (for example, ion mobility), precipitation, crystallization, and membrane separation. The liquid chromatography is preferably high performance liquid chromatography (HPLC). These methods can be performed by publicly known methods.

It is preferable that the separation is performed by liquid chromatography. Examples of liquid chromatography may include normal phase liquid chromatography of a separation system in which the polarity of stationary phase is higher than that of mobile phase, reverse phase liquid chromatography of a separation system in which the polarity of stationary phase is lower than that of mobile phase, hydrophilic interaction chromatography (HILIC), ion exchange chromatography (IEX), and size exclusion chromatography (SEC).

The normal phase liquid chromatography can be performed by a publicly known method. For example, the normal phase liquid chromatography can be performed using a stationary phase such as silica and alumina and a mobile phase such as hexane, ethyl acetate, methylene chloride, isopropanol, ethanol, methanol, tetrahydrofuran, and a mixed solvent of these. Of the normal phase liquid chromatography, a hydrophilic interaction column chromatography is preferable.

The reverse phase liquid chromatography can be performed by a publicly known method. Examples of stationary phase of the reverse phase liquid chromatography may include a filler modified with a hydrophobic compound. Specific examples of stationary phase of the reverse phase liquid chromatography may include a silica gel modified with a hydrophobic compound. Examples of mobile phase of the reverse phase liquid chromatography may include an organic solvent, an aqueous solution, and a mixed solvent of these. Preferable examples of the organic solvent may include acetonitrile, methanol, ethanol, and isopropanol. Preferable examples of the aqueous solution may include water, a formic acid aqueous solution, an ammonium formate aqueous solution, a trifluoroacetic acid aqueous solution, an acetic acid aqueous solution, an ammonium acetate aqueous solution, an ammonium bicarbonate aqueous solution, aqueous ammonia, and a buffer solution. When peak resolution is low, an ion-pair reagent may be added to the solvent to improve the resolution. As the ion-pair reagent, sodium alkylsulfonate or a salt thereof, or tetraalkylammonium or trialkylamine or a salt thereof is used. When the mobile phase in the liquid chromatography is a mixed solvent, the mixing ratio may be changed stepwise or continuously. The temperature condition and the flow rate of the mobile phase in the liquid chromatography may be appropriately set depending on the properties of the first derivative and the second derivative and the resolution of the first derivative and the second derivative.

The liquid chromatography is preferably the reverse phase liquid chromatography.

In the separation, a hydrophobic column may be used. The term "hydrophobic column" used herein means a column using a hydrophobic filler material for a stationary phase. Examples of the hydrophobic filler material may include fillers (for example, silica gels and polymer fillers) modified with an alkyl compound (for example, $C_1$ to $C_{40}$ compound and adamantyl group) or an aromatic compound (for example, aryl compounds such as benzene and naphthalene). In the modification, a linker may be contained between a surface of a filler and a modifying group. When a filler modified with an aromatic compound is used for the hydrophobic column and a hydrophobic material is used as the axially chiral compound, the enantiomers can be analyzed at high sensitivity in a short time with high resolution.

It is preferable that the separation is performed by the reverse phase high performance liquid chromatography (reverse phase HPLC) using the hydrophobic column described above. In this case, a mixed solvent of an aqueous solution (for example, water, a formic acid aqueous solution, an ammonium formate aqueous solution, a trifluoroacetic acid aqueous solution, an acetic acid aqueous solution, an ammonium acetate aqueous solution, an ammonium bicarbonate aqueous solution, and aqueous ammonia) with an organic solvent (for example, acetonitrile, methanol, ethanol, and isopropanol) can be used as the mobile phase. The separation can be performed under a gradient condition. The gradient condition used may be a condition in which a mixed solvent having the ratio of the aqueous solution higher than that of the organic solvent is first used, and a mixed solvent having the ratio of the aqueous solution lower than that of the organic solvent, which is obtained by decreasing the ratio of the aqueous solution stepwise or continuously, is used.

In the separation, the retention times of the first derivative and the second derivative can be appropriately set. According to the method of the present invention, when the retention times of the first derivative and the second derivative are set to a short time, the enantiomers can be analyzed in a short time. The retention times of the first derivative and the second derivative are not particularly limited. The retention times of the first derivative and the second derivative can be appropriately set according to the kind of enantiomers to be analyzed by the method of the present invention and the object of the method of the present invention. The retention times of the first derivative and the second derivative are, for example, within about 120 minutes, within about 90 minutes, within about 60 minutes, within about 50 minutes, within about 40 minutes, within about 30 minutes, within about 20 minutes, within about 15 minutes, or within about 10 minutes. When an amino acid and a carboxylic acid compound are used as the enantiomers, the retention time can be set within about 20 minutes according to the method of the present invention. Therefore, the method of the present invention can be performed in a short time. In the method of the present invention, 19 kinds of L-amino acids (except for glycine) of proteinogenic amino acids (20 kinds) and 19 kinds of D-amino acids that are enantiomers of the L-amino acids can be all comprehensively analyzed at a retention time set within 20 minutes. Therefore, the method of the present invention is excellent in rapid analysis of proteinogenic amino acids that are the enantiomers.

When there are a small peak and a large peak in one chromatogram and elution of the large peak first occurs, the small peak may be laid on a tailing of the large peak. This configuration may reduce quantitative properties and make the analysis complex. Therefore, elution of a peak on a low concentration side that is found before elution of a peak on a high concentration side has a technical significance. When an amino acid contained in a higher organism (for example, an amino acid contained in blood plasma) is analyzed, it is important that a D-amino acid of which the concentration is low is eluted before an L-amino acid of which the concentration is high from the viewpoint described above. When among biological samples, a sample to be analyzed is a sample taken from some tissues, a sample produced by fermentation or the like, or a synthesized product, a D-amino acid may be contained at a high concentration. In this case, by changing a stereo structure of the axially chiral compound used, the elution order of D form and L form can be easily changed. For all 19 kinds of L-amino acids (except for glycine) of proteinogenic amino acids (20 kinds) and 19 kinds of D-amino acids that are enantiomers of the L-amino acids, a D-amino acid derivative can be successfully eluted before an L-amino acid derivative by the method of the present invention. The relationship between the concentrations of D-amino acid and L-amino acid to be measured may be inversed depending on the kinds thereof. For example, this is applied to analysis of a compound of a synthesized chemical compound and analysis of a moiety rich in D-amino acid. In this case, when the axially chiral compound in an S form is used, the elution order can be changed, and an L-amino acid can be easily first eluted.

The separation may be performed so that the resolution R represented by the following expression is 0.5 or more. When the resolution R is 0.5 or more, the enantiomers can be sufficiently separated and analyzed.

$$R = \frac{1.18 \times |t_1 - t_2|}{W_1 + W_2}$$

(wherein $t_1$ is the retention time (minute) of the first derivative, $t_2$ is the retention time (minute) of the second derivative, $W_1$ is the peak width at half-height (minute) of the first derivative, $W_2$ is the peak width at half-height (minute) of the second derivative, the denominator is an absolute value, and R is a positive value.)

The resolution R may be 0.6 or more, 0.7 or more, 0.8 or more, 0.9 or more, 1.0 or more, 1.2 or more, 1.3 or more, 1.4 or more, or 1.5 or more. A higher resolution R is more excellent in resolution performance of enantiomers.

Step (3)

In this step, the first derivative and the second derivative separated are detected by mass spectrometry.

The mass spectrometry is not particularly limited. Mass spectrometry that is combination of various types of ionization method, various types of ion separation method, and various types of detector may be used.

Examples of the ionization method may include an electron ionization (EI) method, a chemical ionization (CI) method, a fast atom bombardment (FAB) method, an electrospray ionization (ESI) method, an atmospheric pressure chemical ionization (APCI) method, an atmospheric pressure photoionization (APPI) method, a matrix-assisted laser desorption/ionization (MALDI) method, a soft laser desorption/ionization mass spectrometry (LDI) method, a desorption electrospray ionization (DESI) method, and a probe electrospray ionization (PESI) method.

Examples of the ion separation method may include a magnetic field mass separation method, a quadrupole mass separation method, an ion trap mass separation method, a time-of-flight mass separation method, a Fourier transform ion cyclotron mass separation method, and an ion separation method using an electric field Fourier transform mass spectrometer.

Examples of the detector may include a secondary electron multiplier, a post-deflection acceleration detector, a channeltron, a multichanneltron, an array detector, a position and time-resolved array detector, and a photoelectron multiplier.

In the mass spectrometry, a negative mode of detecting a negative charge or a positive mode of detecting a positive charge may be performed. It is preferable that a positive mode of detecting a positive charge is performed.

In detection by the mass spectrometry, one mass separator or a device including two or more mass separators connected in series may be used. For example, the detection can be performed by a device including three mass separators connected in series (for example, a triple quadrupole mass spectrometer, a quadrupole-time-of-flight mass spectrometer, and a quadrupole-kingdon trap mass spectrometer). When a triple quadrupole mass spectrometer is used in the detection, the detection can be performed by any method of selected reaction monitoring (SRM), a product ion scan mode, a precursor ion scan mode, or a neutral loss scan mode. Before use of the mass spectrometer, a mass spectrometer with an ion mobility separation function may be used.

When a triple quadrupole mass spectrometer is used in the detection, it is preferable that the detection is performed by SRM. Herein, three quadrupoles are named Q1, Q2, and Q3 from a side near an ion source. In Q1, a specific ion is selected as a precursor ion. In Q2, the precursor ion is fragmented. In Q3, a certain ion is selected from fragment ions generated by the fragmentation of the precursor ion. Therefore, detection by SRM can be detection in which an influence by a contaminant component is eliminated. When only a compound bonded to the axially chiral compound is tried to be particularly comprehensively detected, measurement is performed by a precursor ion scan in which a fragment ion derived from a reagent is specified, or in some cases, a neutral loss scan. Thus, a compound reacted with the axially chiral compound can be detected.

Since the first derivative and the second derivative contain the charged atom or the chargeable atom, the first derivative and the second derivative can be easily detected by the mass spectrometry.

In detection of the first derivative and the second derivative separated, a method other than the mass spectrometry may be used in combination with the mass spectrometry. Examples of the method may include a method of detecting ultraviolet absorption, a method of detecting visible light absorption, and a method of detecting fluorescence.

In measurement of the first derivative and the second derivative by the mass spectrometry, a component can be separated not only by column chromatography but also according to the mass. This makes it possible to shorten a time required for analysis. In particular, according to the method of the present invention, separation of D forms and L forms regarding at least 19 kinds of proteinogenic amino acids can be completed within 20 minutes.

In the method of the present invention, the separation and detection in the steps (2) and (3) can be performed by using a separator and a detector in combination or using one device for separation and detection. When the method of the present invention is intended to be performed in a short time, it is preferable that the device for separation and detection is used. In this case, for example, LC-MS or LC-MS/MS in which liquid chromatography and mass spectroscopy are performed in parallel can be adopted.

The method of the present invention can be performed as described above. It is preferable that specific embodiments of the method of the present invention described in detail below are performed.

In a specific embodiment, the axially chiral isomer used in the present invention is a substance containing no charged atom or chargeable atom. Specifically, the substance is a compound represented by the following general formula (I):

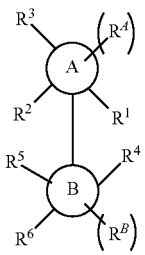

(I)

(wherein
ring A and ring B each independently represent a benzene ring or a heteroaromatic ring,
a bond between the ring A and the ring B represents an axis of chirality,
$R^1$ represents a group bonded to one ring-constituting atom adjacent to a ring A-constituting atom bonded to the ring B,
$R^2$ represents a group bonded to the other ring-constituting atom adjacent to the ring A-constituting atom bonded to the ring B,
$R^3$ represents a hydrogen atom or a group,
or $R^2$ and $R^3$ may form a ring together,
$R^4$ represents a group bonded to one ring-constituting atom adjacent to a ring B-constituting atom bonded to the ring A,
$R^5$ represents a group bonded to the other ring-constituting atom adjacent to the ring B-constituting atom bonded to the ring A,
$R^6$ represents a hydrogen atom or a group,
or $R^5$ and $R^6$ may form a ring together,
the rings A and B may further have one or two $R^A$s and one or two $R^B$s that are bonded to an atom constituting each ring (wherein the one or two $R^A$s and the one or two $R^B$s each represent a group),
the groups are (a) a reactive group or (b) a substituent, and
the reactive group exists only in any one of $R^1$ to $R^6$, $R^A$, and $R^B$.)

In another specific embodiment, the axially chiral isomer used in the present invention is a substance containing a charged atom or a chargeable atom. Specifically, the substance is a compound represented by the following general formula (I'):

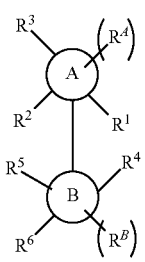

(I')

(wherein
ring A and ring B each independently represent a benzene ring or a heteroaromatic ring,
a bond between the ring A and the ring B represents an axis of chirality,
$R^1$ represents a group bonded to one ring-constituting atom adjacent to a ring A-constituting atom bonded to the ring B,
$R^2$ represents a group bonded to the other ring-constituting atom adjacent to the ring A-constituting atom bonded to the ring B,
$R^3$ represents a hydrogen atom or a group,
or $R^2$ and $R^3$ may form a ring together,
$R^4$ represents a group bonded to one ring-constituting atom adjacent to a ring B-constituting atom bonded to the ring A,
$R^5$ represents a group bonded to the other ring-constituting atom adjacent to the ring B-constituting atom bonded to the ring A,
$R^6$ represents a hydrogen atom or a group,
or $R^5$ and $R^6$ may form a ring together,
the ring A and the ring B may further have one or two $R^A$s and one or two $R^B$s that are bonded to an atom constituting each ring (wherein the one or two $R^A$s and the one or two $R^B$s each represent a group),
the groups are (a) a reactive group, (b) a group having a charged atom or a chargeable atom, or (c) a substituent,
the reactive group exists only in any one of $R^1$ to $R^6$, $R^A$, and $R^B$, and
when the group having a charged atom or a chargeable atom does not exist in any of $R^1$ to $R^6$, $R^A$, and $R^B$, at least one of the ring A and the ring B represents a heteroaromatic ring having a charged atom or a chargeable atom, or at least one of the ring formed by $R^2$ and $R^3$ together and the ring formed by $R^5$ and $R^6$ together exists and represents a ring having a charged atom or a chargeable atom.)

In the compound represented by the general formula (I) or (I'), definitions, examples, and preferable examples of the heteroaromatic ring, the reactive group, and the group having a charged atom or a chargeable atom are as described above. The ring formed by $R^2$ and $R^3$ together and the ring formed by $R^5$ and $R^6$ together are the aromatic or non-aromatic ring described above. Specifically, the ring formed by $R^2$ and $R^3$ together and the ring formed by $R^5$ and $R^6$ together exist in a form condensed with a benzene ring or a heteroaromatic ring, and form the bicyclic condensed ring described above (preferably, the bicyclic aromatic ring described above) with a benzene ring or a heteroaromatic ring.

The groups in the compound represented by general formula (I) or (I'), that is, the group of $R^1$ (the group bonded to one ring-constituting atom adjacent to the ring A-constituting atom bonded to the ring B), the group of $R^2$ (the group bonded to the other ring-constituting atom adjacent to the ring A-constituting atom bonded to the ring B), the group of $R^3$, the group of $R^4$ (the group bonded to one ring-constituting atom adjacent to the ring B-constituting atom bonded to the ring A), the group of $R^5$ (the group bonded to the other ring-constituting atom adjacent to the ring B-constituting atom bonded to the ring A), the group of $R^6$, the group of $R^A$, and the group of $R^B$ are a reactive group, a group having a charged atom or a chargeable atom, or a substituent. Since $R^1$, $R^2$, $R^4$, and $R^5$ have such a group, but not a hydrogen atom, the free rotation with respect to the axis of chirality of the axially chiral compound that is a rotation axis can be restricted. When the reactive group exists only in any one of $R^1$ to $R^6$, $R^A$, and $R^B$, one kind of first derivative and one kind of second derivative that have a diastereomeric relationship are produced by a reaction of the first compound and the second compound that are the pair of enantiomers with the axially chiral compound as described above. Therefore, the analysis of the pair of enantiomers can be facilitated.

Unless otherwise specified, the term "substituent" used herein may be the following substituents (i) to (iv):

(i) a halogen atom, hydroxy, sulfanyl, amino, guanidino, carboxy, formyl, carbamoyl, carbamoylamino, or cyano;

(ii) $C_1$ to $C_6$ alkyl, $C_1$ to $C_6$ alkyloxy, $C_1$ to $C_6$ alkylcarbonyl, $C_1$ to $C_6$ alkyloxycarbonyl, $C_1$ to $C_6$ alkylcarbonyloxy, $C_1$ to $C_6$ alkylthio, mono($C_1$ to $C_6$ alkyl)amino, or di($C_1$ to $C_6$ alkyl)amino (herein, the groups may be substituted with one to three substituents selected from the group consisting of a halogen atom, hydroxy, sulfanyl, amino, guanidino, carboxy, formyl, carbamoyl, carbamoylamino, and cyano);

(iii) phenyl, phenyloxy, phenylcarbonyl, phenyloxycarbonyl, phenylcarbonyloxy, phenylthio, monophenylamino, phenyl($C_1$ to $C_6$ alkyl)amino, or diphenylamino (herein, the groups may be substituted with one to three substituents selected from the group consisting of a halogen atom, hydroxy, sulfanyl, amino, guanidino, carboxy, formyl, carbamoyl, carbamoylamino, and cyano); or (iv) heteroaryl, heteroaryloxy, heteroarylcarbonyl, heteroaryloxycarbonyl, heteroarylcarbonyloxy, heteroarylthio, monoheteroarylamino, N-heteroaryl-N—($C_1$ to $C_6$ alkyl) amino, N-heteroaryl-N-(phenyl)amino, or diheteroarylamino (herein, heteroaryl is a monocyclic or bicyclic heteroaromatic ring group. The groups may be substituted with one to three substituents selected from the group consisting of a halogen atom, hydroxy, sulfanyl, amino, guanidino, carboxy, formyl, carbamoyl, carbamoylamino, and cyano).

Examples of the term "halogen atom" used herein may include a fluorine atom, a chlorine atom, a bromine atom, and an iodine atom.

The expression "$C_x$ to $C_y$" (wherein x and y are a positive integer satisfying that y is larger than x) means that the number of carbon atoms of a group or ring described after the expression falls within a range of x to y.

The term "$C_1$ to $C_6$ alkyl" used herein means a linear or branched alkyl of one to six carbon atoms. Examples of the $C_1$ to $C_6$ alkyl may include methyl, ethyl, propyl, iso-propyl, butyl, iso-butyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl. The $C_1$ to $C_6$ alkyl is preferably $C_1$ to $C_4$ alkyl.

The term "$C_1$ to $C_6$ alkyloxy" used herein means an oxy group having the "$C_1$ to $C_6$ alkyl" described above (i.e., $C_1$ to $C_6$ alkyl-O—). Examples of the "$C_1$ to $C_6$ alkyl" in the term "$C_1$ to $C_6$ alkyloxy" are as described above. Specific examples of the $C_1$ to $C_6$ alkyloxy may include methoxy, ethoxy, propyloxy, 1-methylethyloxy, and butyloxy. The $C_1$ to $C_6$ alkyloxy is preferably $C_1$ to $C_4$ alkyloxy.

The term "$C_1$ to $C_6$ alkylcarbonyl" used herein means a carbonyl group having the "$C_1$ to $C_6$ alkyl" described above (i.e., $C_1$ to $C_6$ alkyl-CO—). Examples of the "$C_1$ to $C_6$ alkyl" in the term "$C_1$ to $C_6$ alkylcarbonyl" are as described above. Specific examples of the $C_1$ to $C_6$ alkylcarbonyl may include acetyl, propanoyl, and butanoyl. The $C_1$ to $C_6$ alkylcarbonyl is preferably $C_1$ to $C_4$ alkylcarbonyl.

The term "$C_1$ to $C_6$ alkyloxycarbonyl" used herein means an oxycarbonyl group having the "$C_1$ to $C_6$ alkyl" described above (i.e., $C_1$ to $C_6$ alkyl-O—CO—). Examples of the "$C_1$ to $C_6$ alkyl" in the term "$C_1$ to $C_6$ alkyloxycarbonyl" are as described above. Specific examples of the $C_1$ to $C_6$ alkyloxycarbonyl may include methyloxycarbonyl, ethyloxycarbonyl, and butyloxycarbonyl. The $C_1$ to $C_6$ alkyloxycarbonyl is preferably $C_1$ to $C_4$ alkyloxycarbonyl.

The term "$C_1$ to $C_6$ alkylcarbonyloxy" used herein means a carbonyloxy group having the "$C_1$ to $C_6$ alkyl" described above (i.e., $C_1$ to $C_6$ alkyl-CO—O—). Examples of the "$C_1$ to $C_6$ alkyl" in the term "$C_1$ to $C_6$ alkylcarbonyloxy" are as described above. Specific examples of the $C_1$ to $C_6$ alkylcarbonyloxy may include acetoxy and ethylcarbonyloxy. The $C_1$ to $C_6$ alkylcarbonyloxy is preferably $C_1$ to $C_4$ alkylcarbonyloxy.

The term "$C_1$ to $C_6$ alkylthio" used herein means a thio group having the "$C_1$ to $C_6$ alkyl" described above (i.e., $C_1$ to $C_6$ alkyl-S—). Examples of the "$C_1$ to $C_6$ alkyl" in the term "$C_1$ to $C_6$ alkylthio" are as described above. Specific examples of the $C_1$ to $C_6$ alkylthio may include methylthio and ethylthio. The $C_1$ to $C_6$ alkylthio is preferably $C_1$ to $C_4$ alkylthio.

The term "mono($C_1$ to $C_6$ alkyl)amino" used herein means an amino group mono-substituted with the "$C_1$ to $C_6$ alkyl" described above. Examples of the "$C_1$ to $C_6$ alkyl" in the term "mono($C_1$ to $C_6$ alkyl)amino" are as described above. Specific examples of the mono($C_1$ to $C_6$ alkyl)amino may include methylamino and ethylamino. The mono($C_1$ to $C_6$ alkyl)amino is preferably mono($C_1$ to $C_4$ alkyl)amino.

The term "di($C_1$ to $C_6$ alkyl)amino" used herein means an amino group di-substituted with the "$C_1$ to $C_6$ alkyl" described above. Examples of the "$C_1$ to $C_6$ alkyl" in the term "di($C_1$ to $C_6$ alkyl)amino" are as described above. Specific examples of the di($C_1$ to $C_6$ alky)amino may include dimethylamino and diethylamino. The di($C_1$ to $C_6$ alkyl)amino is preferably di($C_1$ to $C_4$ alkyl)amino.

The term "phenyl($C_1$ to $C_6$ alkyl)amino" used herein means an amino group substituted with phenyl and the "$C_1$ to $C_6$ alkyl" described above. Examples of the "$C_1$ to $C_6$ alkyl" in the term "di($C_1$ to $C_6$ alkyl)amino" are as described above. Specific examples of the phenyl($C_1$ to $C_6$ alky)amino may include methylphenylamino and ethylphenylamino.

The term "heteroaryl" and "heteroaryl" in terms "heteroaryloxy", "heteroarylcarbonyl", "heteroaryloxy carbonyl", "heteroarylcarbonyloxy", "heteroarylthio", "monoheteroarylamino", "N-heteroaryl-N—($C_1$ to $C_6$ alkyl)amino", "N-heteroaryl-N-(phenyl)amino", and "diheteroarylamino" used herein are a monocyclic or bicyclic heteroaromatic ring group. Examples of the monocyclic heteroaromatic ring may include groups of "five-membered heteroaromatic ring" and "six-membered heteroaromatic ring" described above. The monocyclic heteroaromatic ring is preferably a group of a five-membered nitrogen-containing heteroaromatic ring (for example, pyrrole, pyrazole, isoxazole, isothiazole, imidazole, oxazole, and thiazole), or a group of six-membered nitrogen-containing heteroaromatic ring (for example, as described above). The bicyclic heteroaromatic ring group is preferably a group of a bicyclic nitrogen-containing heteroaromatic ring (for example, indole, benzopyrazole, benzisoxazole, benzisothiazole, benzimidazole, benzoxazole, benzothiazole, quinoline, isoquinoline, cinnoline, phthalazine, quinazole, quinoxaline, pteridine, and purine).

The term "heteroaryloxy" used herein means an oxy group having the "heteroaryl" described above (i.e., heteroaryl-O—). Examples and preferable examples of "heteroaryl" in the term "heteroaryloxy" are as described above. Specific examples of the heteroaryloxy may include pyrrolyloxy, oxazolyloxy, thiazolyloxy, and pyridyloxy.

The term "heteroarylcarbonyl" used herein means a carbonyl group having the "heteroaryl" described above (i.e., heteroaryl-CO—). Examples of "heteroaryl" in the term "heteroarylcarbonyl" are as described above. Specific examples of the heteroarylcarbonyl may include pyrrolylcarbonyl, oxazolylcarbonyl, thiazolylcarbonyl, and pyridylcarbonyl.

The term "heteroaryloxycarbonyl" used herein means an oxycarbonyl group having the "heteroaryl" described above (i.e., heteroaryl-O—CO—). Examples of "heteroaryl" in the term "heteroaryloxycarbonyl" are as described above. Specific examples of the heteroaryloxycarbonyl may include pyrrolyloxycarbonyl, oxazolyloxycarbonyl, thiazolyloxycarbonyl, and pyridyloxycarbonyl.

The term "heteroarylcarbonyloxy" used herein means a carbonyloxy group having the "heteroaryl" described above (i.e., heteroaryl-CO—O—). Examples of "heteroaryl" in the term "heteroarylcarbonyloxy" are as described above. Specific examples of the heteroarylcarbonyloxy may include pyrrolylcarbonyloxy, oxazolylcarbonyloxy, thiazolylcarbonyloxy, and pyridylcarbonyloxy.

The term "heteroarylthio" used herein means a thio group having the "heteroaryl" described above (i.e., heteroaryl-S—). Examples of "heteroaryl" in the term "heteroarylthio" are as described above. Specific examples of the heteroarylthio may include pyrrolylthio, oxazolylthio, thiazolylthio, and pyridylthio.

The term "N-heteroaryl-N—($C_1$ to $C_6$ alkyl)amino" used herein means an amino group di-substituted with the "heteroaryl" and "$C_1$ to $C_6$ alkyl" described above. Examples of the "$C_1$ to $C_6$ alkyl" in the term "N-heteroaryl-N—($C_1$ to $C_6$ alkyl)amino" are as described above.

The term "substituent" is as described above. The term "substituent" is preferably a group that cannot be charged and cannot be reacted with the first compound and the second compound that are the pair of enantiomers. The group that cannot be charged and cannot be reacted with the first compound and the second compound that are the pair of enantiomers varies depending on the kinds of the first compound and the second compound and the kind of charging state to be detected by the mass spectrometry. The group that cannot be charged and cannot be reacted with the first compound and the second compound that are the pair of enantiomers can be appropriately selected according to details of the method of the present invention to be adopted. The group that cannot be charged and cannot be reacted with the first compound and the second compound that are the pair of enantiomers is preferably $C_1$ to $C_6$ alkyl among the aforementioned substituents.

In a preferable embodiment, the compound represented by the general formula (I) described above is a compound represented by the following general formula (II):

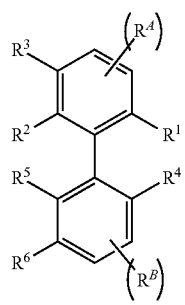

(II)

(wherein
a bond between benzene rings represents an axis of chirality,
$R^1$ and $R^4$ each represents a group,
$R^2$ represents a group,
$R^3$ represents a hydrogen atom or a group,
or $R^2$ and $R^3$ may form a ring together,
$R^5$ represents a group,
$R^6$ represents a hydrogen atom or a group,
or $R^5$ and $R^6$ may form a ring together,
the two benzene rings may further have one or two $R^A$s and one or two $R^B$s that are bonded to an atom constituting each ring (wherein the one or two $R^A$s and the one or two $R^B$s each represent a group), the groups are (a) a reactive group or (b) a substituent, and
the reactive group exists only in any one of $R^1$ to $R^6$, $R^A$, and $R^B$.)

In another preferable embodiment, the compound represented by the general formula (I') described above is a compound represented by the following general formula (II'):

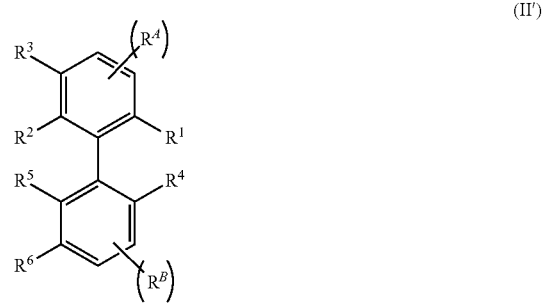

(II')

(wherein
a bond between benzene rings represents an axis of chirality,
$R^1$ and $R^4$ each represent a group,
$R^2$ represents a group,
$R^3$ represents a hydrogen atom or a group,
or $R^2$ and $R^3$ may form a ring together,
$R^5$ represents a group,
$R^6$ represents a hydrogen atom or a group,
or $R^5$ and $R^6$ may form a ring together,
the two benzene rings may further have one or two $R^A$s and one or two $R^B$s that are bonded to an atom constituting each ring (wherein the one or two $R^A$s and the one or two $R^B$s each represent a group),
the groups are (a) a reactive group, (b) a group having a charged atom or a chargeable atom, or (c) a substituent,
the reactive group exists only in any one of $R^1$ to $R^6$, $R^A$, and $R^B$, and
when the group having a charged atom or a chargeable atom does not exist in any of $R^1$ to $R^6$, $R^A$, and $R^B$, at least one of the ring formed by $R^2$ and $R^3$ together and the ring formed by $R^5$ and $R^6$ together exists and represents a ring having a charged atom or a chargeable atom.)

In the compound represented by the general formula (II) or (II'), definitions, examples, and preferable examples of the reactive group and the group having a charged atom or a chargeable atom are as described above. The ring formed by $R^2$ and $R^3$ together and the ring formed by $R^5$ and $R^6$ together are the same as those in the compound represented by the general formula (I) described above.

The groups in the compound represented by the general formula (II) or (II'), that is, the groups of $R^1$ to $R^6$, $R^A$, and $R^B$ are a reactive group, a group having a charged atom or a chargeable atom, or a substituent. Details of the groups are the same as those of the compound represented by the general formula (I) or (I').

In a more preferable embodiment, the axially chiral isomers used in the present invention are a compound represented by the following general formula (II-1):

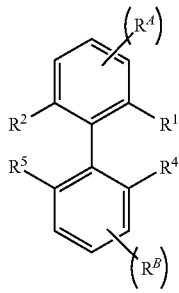

(II-1)

(wherein a bond between two benzene rings represents an axis of chirality, $R^1$ represents a reactive group, $R^4$ represents a group having a charged atom or a chargeable atom, $R^2$ and $R^5$ each represent a substituent, and the two benzene rings may further have one or two $R^A$s and one or two $R^B$s that are bonded to an atom constituting each ring (wherein the one or two $R^A$s and the one or two $R^B$s each represent a substituent).)

In the compound represented by the general formula (II-1) described above, details of the reactive group and the group having a charged atom or a chargeable atom are as described above.

In a further preferable embodiment, the axially chiral compound that is one of the axially chiral isomers used in the present invention is a compound represented by the following general formula (II-1-1). The compound represented by the following general formula (II-1-1) is an R form with respect to an axis of chirality.

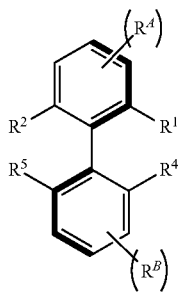

(II-1-1)

(wherein a bold line is a bond located before the paper, and $R^1$, $R^2$, $R^4$, $R^5$, $R^A$, and $R^B$ have the same meaning as $R^1$, $R^2$, $R^4$, $R^5$, $R^A$, and $R^B$, respectively, in the aforementioned general formula (II-1).)

In another more preferable embodiment, the axially chiral isomers used in the present invention are a compound represented by the following general formula (II-2):

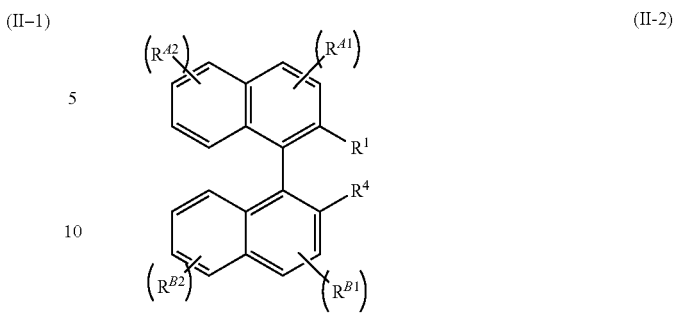

(II-2)

(wherein a bond between two naphthalene rings represents an axis of chirality, $R^1$ represents a reactive group, $R^4$ represents a group having a charged atom or a chargeable atom, and the two naphthalene rings may further have one or two $R^{A1}$ s and one to four $R^{A2}$s and one or two $R^{B1}$s and one to four $R^{B2}$s that are bonded to an atom constituting each ring (wherein the one or two $R^{A1}$ s and the one to four $R^{A2}$s and the one or two $R^{B1}$s and the one to four $R^{B2}$s each represent a substituent).)

In the compound represented by the general formula (II-2) described above, details of the reactive group and the group having a charged atom or a chargeable atom are as described above.

In a further preferable embodiment, the axially chiral compound that is one of the axially chiral isomers used in the present invention is a compound represented by the following general formula (II-2-1). The compound represented by the following general formula (II-2-1) is an R form with respect to an axis of chirality.

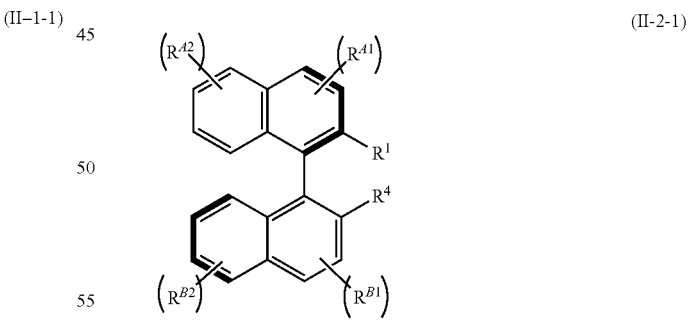

(II-2-1)

(wherein a bold line is a bond located before the paper, and $R^1$, $R^4$, $R^{A1}$, $R^{A2}$, $R^{B1}$, and $R^{B1}$ have the same meaning as $R^1$, $R^4$, $R^{A1}$, $R^{A2}$, $R^{B1}$, and $R^{B1}$, respectively, in the aforementioned general formula (II-2).)

In a particularly preferable embodiment, examples of the axially chiral isomers used in the present invention may include compounds represented by the following general formulae (101) to (114).

(101) 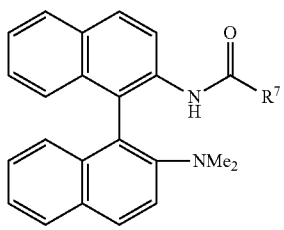
(102) 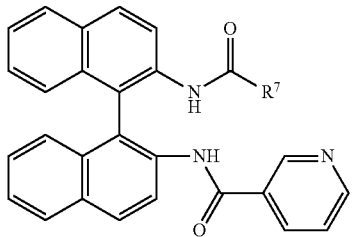
(103) 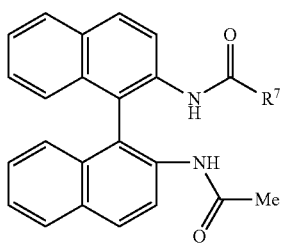
(104) 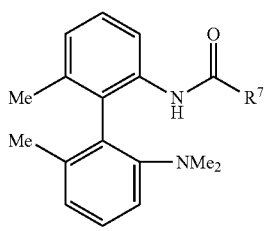
(105) 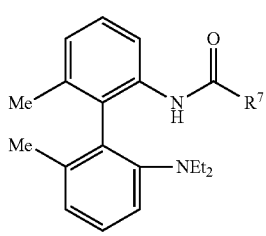
(106) 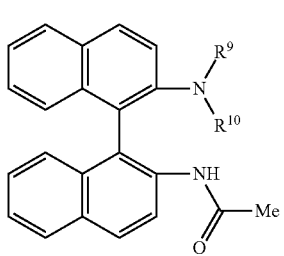
-continued
(107) 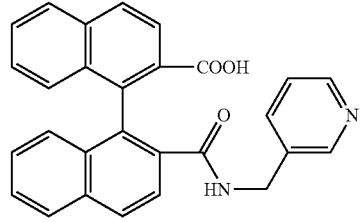
(108) 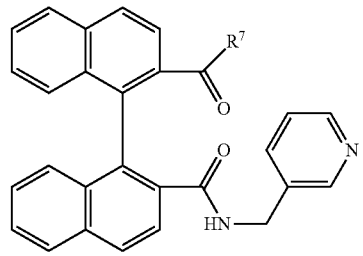
(109) 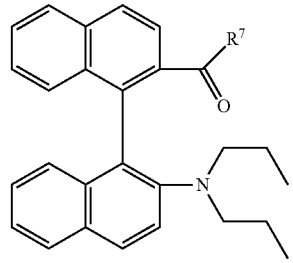
(110) 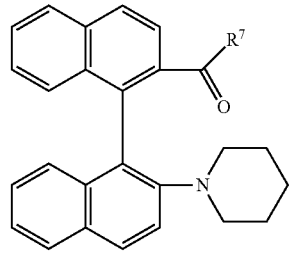
(111) 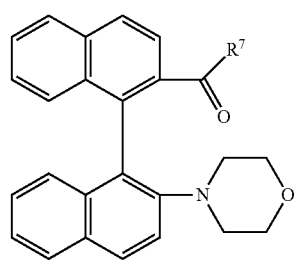
(112) 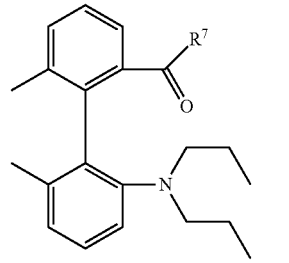

-continued (113)

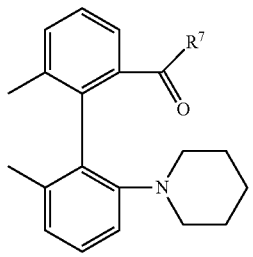

(114)

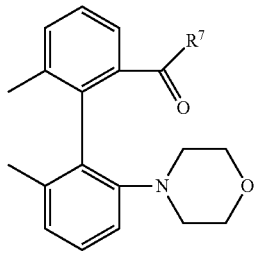

In the aforementioned formulae (101) to (105) and (108) to (114), $R^7$ represents a leaving group. Definition, examples, and preferable examples of the leaving group represented by $R^7$ are the same as described above.

In the aforementioned formula (106), $R^9$ and $R^{10}$ each independently represent a hydrogen atom or a $C_1$ to $C_6$ alkyl group. Definitions, examples, and preferable examples of the $C_1$ to $C_6$ alkyl groups represented by $R^9$ and $R^{10}$ are the same as described above.

The present invention also provides a novel axially chiral compound or a salt thereof.

Examples of the salt of the novel axially chiral compound may include metal salts (for example, monovalent metal salts such as sodium salts and potassium salts, and divalent metal salts such as calcium salts and magnesium salts), inorganic salts (for example, salts of halides such as a fluoride, a chloride, a bromide, and an iodide, and ammonium salts), organic salts (for example, ammonium salts substituted with an alkyl group), and acid addition salts (for example, salts with inorganic acids such as sulfuric acid, hydrochloric acid, hydrobromic acid, nitric acid, and phosphoric acid, and salts with organic acids such as acetic acid, oxalic acid, lactic acid, citric acid, trifluoromethanesulfonic acid, and trifluoroacetic acid).

Specifically, the axially chiral compound of the present invention is the compound represented by the aforementioned formula (I') or (II') wherein the reactive group is (a') a group represented by the general formula (i), a group represented by the general formula (ii), or a group containing a group represented by the general formula (i) or (ii), and the group having a charged atom or a chargeable atom is di($C_1$ to $C_6$ alkyl)amino, tri($C_1$ to $C_6$ alkyl)ammonio, a piperidino group, a morpholino group, or a group represented by the aforementioned general formula (d1) or the aforementioned general formula (d2), and at least one of $R^1$ to $R^6$, $R^A$, and $R^B$ is a group having a charged atom or a chargeable atom; or a compound represented by the aforementioned formula (II-1), (II-1-1), (II-2), or (II-2-1) wherein the reactive group in the formula is (a') a group represented by the general formula (i), a group represented by the general formula (ii), or a group containing a group represented by the general formula (i) or (ii), and the group having a charged atom or a chargeable atom is di($C_1$ to $C_6$ alkyl)amino, tri($C_1$ to $C_6$ alkyl)ammonio, a piperidino group, a morpholino group, or a group represented by the aforementioned general formula (d1) or the aforementioned general formula (d2). When the reactive group is the specific reactive group described above, a sign "'" may be assigned to the number for the aforementioned formula for discrimination.

The group represented by the general formula (i) is as follows.

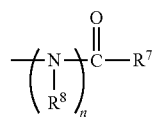

(i)

(wherein
$R^7$ represents a hydroxy group or a leaving group,
n represents 0 or 1, and
$R^8$ does not exist when n is 0, or
$R^8$ represents a hydrogen atom or a $C_1$ to $C_6$ alkyl group when n is 1.)

In the general formula (i), the $C_1$ to $C_6$ alkyl group represented by $R^8$ is the same as described above. n is preferably 1.

In the general formula (i), the leaving group represented by $R^7$ is the same as described above, and is preferably $C_1$ to $C_6$ alkylcarbonyloxy, a halogen atom, succinimidooxy, phenyloxy having an electron withdrawing group, imidazolyl, or triazolyl.

The group represented by the general formula (ii) is as follows.

(ii)

(wherein
$R^9$ and $R^{10}$ each independently represent a hydrogen atom or a $C_1$ to $C_6$ alkyl group.)

In the general formula (ii), the $C_1$ to $C_6$ alkyl group represented by $R^9$ and $R^{10}$ is the same as described above. $R^9$ and $R^{10}$ are each preferably a hydrogen atom.

The group containing the group represented by the aforementioned general formula (i) or (ii) is intended to be a group containing the group represented by the general formula (i) or (ii) through a linker represented by a formula: $-(L)_m-$ (wherein L is a repeatable unit, and m is an integer of 1 to 10), as described above. Examples and preferable examples of L and m are as described above. Such a group can also act as a reactive group.

The axially chiral compound of the present invention can be produced by using a conventionally known method.

For example, a compound represented by the following general formula (I'a) that is a preferable example of the aforementioned general formula (I) or (I') can be produced by the following reaction.

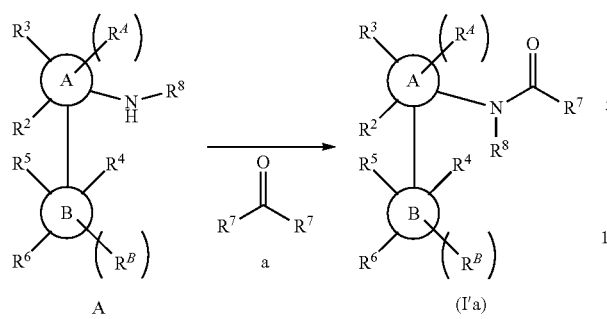

In the general formula A and the general formula (I'a) of the aforementioned reaction formula, a ring A, a ring B, $R^2$, $R^3$, $R^4$, $R^5$, $R^6$, $R^A$, and $R^B$ have the same meaning as the ring A, the ring B, $R^2$, $R^3$, $R^4$, $R^5$, $R^6$, $R^A$, and $R^B$, respectively, in the general formula (I) described above, $R^7$ represents a leaving group, and $R^8$ represents a hydrogen atom or $C_1$ to $C_6$ alkyl.

As a compound a in the aforementioned reaction formula, for example, N,N'-disuccinimidyl carbonate (DSC), bispentafuluorophenyl carbonate, or 1,1'-carbonyldiimidazole (CDT) can be used.

Instead of the compound a, for example, chloroformate containing a group $R^7$ (for example, 4-nitrophenyl chloroformate) may be used.

The equivalent of the compound a with respect to the compound represented by the general formula A is preferably one equivalent or more. As a solvent in the aforementioned reaction, a reaction solvent that is unreactive with the compound a and the compound represented by the general formula A can be used. Examples of the reaction solvent may include dichloromethane. The reaction temperature and the reaction time can be set according to properties of the compound represented by the general formula A and the compound a. For example, the reaction temperature is room temperature (for example, 15° C. to 25° C.) and the reaction time is 8 hours or more.

The axially chiral compound of the present invention is useful for, for example, derivatizing an enantiomer. Therefore, the present invention also provides an enantiomer-derivatizing agent (for example, a derivatizing agent for mass spectrometry) including the axially chiral compound according to the present invention or a salt thereof. Specifically, the axially chiral compound contained in the derivatizing agent according to the present invention is a compound represented by the aforementioned formula (I), (I'), (II), (II-1), (II-1-1), (II-2), or (II-2-1).

In a preferable embodiment, the axially chiral compound contained in the derivatizing agent according to the present invention is:

a compound in which in the aforementioned formula (I') or (II'), the reactive group is (a') a group represented by the general formula (i), a group represented by the general formula (ii), or a group containing the group represented by the general formula (i) or (ii), the group having a charged atom or a chargeable atom is di($C_1$ to $C_6$ alkyl)amino, tri($C_1$ to $C_6$ alkyl)ammonio, a piperidino group, a morpholino group, or a group represented by the aforementioned general formula (d1) or (d2), and at least one of $R^1$ to $R^6$, $R^A$, and $R^B$ is a group having a charged atom or a chargeable atom; or a compound in which in the aforementioned formula (II-1), (II-1-1), (II-2), or (II-2-1), the reactive group is (a') a group represented by the general formula (i), a group represented by the general formula (ii), or a group containing a group represented by the general formula (i) or (ii), and the group having a charged atom or a chargeable atom is di($C_1$ to $C_6$ alkyl)amino, tri($C_j$ to $C_6$ alkyl)ammonio, a piperidino group, a morpholino group, or a group represented by the aforementioned general formula (d1) or (d2).

In another specific preferable embodiment, the pair of enantiomers is a specific chiral amino acid. An example of the specific chiral amino acid is an amino acid represented by the following general formula (A-1) or general formula (A-2).

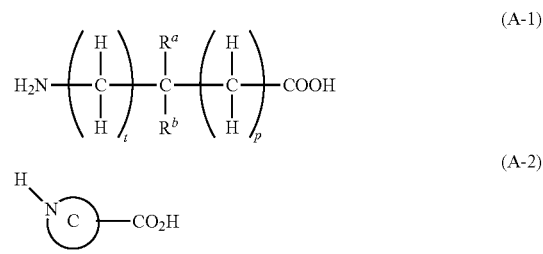

In the aforementioned general formula (A-1), $R^a$ and $R^b$ are each independently a group selected from the group consisting of a hydrogen atom, a halogen atom, hydroxy, sulfanyl, guanidino, formyl, carbamoyl, carbamoylamino, cyano, $C_1$ to $C_6$ alkyl optionally substituted with one to three substituents which are the same as or different from each other, phenyl optionally substituted with one to three substituents which are the same as or different from each other, and heteroaryl optionally substituted with one to three substituents which are the same as or different from each other, provided that $R^a$ and $R^b$ are different from each other. t represents an integer of 0 to 3. Preferably, t represents an integer of 0, 1, or 2. p represents an integer of 0 to 3. Preferably, p represents an integer of 0, 1, or 2.

The "$C_1$ to $C_6$ alkyl" represented by $R^a$ and $R^b$ is the same as the aforementioned $C_1$ to $C_6$ alkyl.

The "heteroaryl" of the "heteroaryl optionally substituted with one to three substituents which are the same as or different from each other" represented by $R^a$ and $R^b$ is a monocyclic or bicyclic nitrogen-containing heteroaromatic ring group. Examples of the monocyclic or bicyclic nitrogen-containing heteroaromatic ring group may include the aforementioned "five-membered nitrogen-containing heteroaromatic ring" group and "six-membered nitrogen-containing heteroaromatic ring" group. Examples of the bicyclic nitrogen-containing heteroaromatic ring group may include the aforementioned "bicyclic nitrogen-containing heteroaromatic ring" group.

The "$C_1$ to $C_6$ alkyl", "phenyl", and "heteroaryl" represented by $R^a$ and $R^b$ may have one to three substituents, and preferably one or two substituents. When multiple substituents exist, the substituents may be the same as or different from each other. Examples of the substituent may include the aforementioned substituents of (i) to (iv).

Preferably, $R^a$ represents a hydrogen atom, and $R^b$ represents $C_1$ to $C_6$ alkyl optionally substituted with one to three substituents which are the same as or different from each other.

Preferably, the "substituents" of the "$C_1$ to $C_6$ alkyl optionally substituted with one to three substituents which are the same as or different from each other" as $R^a$ and $R^b$ are the following groups:

(1) hydroxy, sulfanyl, amino, guanidino, carboxy, carbamoyl, or carbamoylamino;

(2) $C_1$ to $C_6$ alkylthio (optionally substituted with one to three substituents selected from the group consisting of a halogen atom, hydroxy, sulfanyl, amino, guanidino, carboxy, formyl, carbamoyl, carbamoylamino, and cyano);

(3) phenyl (optionally substituted with one to three substituents selected from the group consisting of a halogen atom, hydroxy, sulfanyl, amino, guanidino, carboxy, formyl, carbamoyl, carbamoylamino, and cyano); or (4) indolyl or imidazolyl (optionally substituted with one to three substituents selected from the group consisting of a halogen atom, hydroxy, sulfanyl, amino, guanidino, carboxy, formyl, carbamoyl, carbamoylamino, and cyano).

More preferably, the "substituents" of the "$C_1$ to $C_6$ alkyl optionally substituted with one to three substituents which are the same as or different from each other" represented by $R^a$ and $R^b$ are the following groups:

(1') hydroxy, sulfanyl, amino, guanidino, carboxy, carbamoyl, or carbamoylamino;

(2') methylthio;

(3') phenyl or hydroxyphenyl; or (4') indolyl or imidazolyl.

Preferably, $R^a$ represents a hydrogen atom, and $R^b$ represents methyl, 1-methylethyl, 2-methylpropyl, 1-methylpropyl, hydroxymethyl, 1-hydroxyethyl, sulfanylmethyl, 4-aminobutyl, 3-guanidinopropyl, carboxymethyl, 2-carboxyethyl, carbamoylmethyl, 2-carbamoylethyl, 2-(methylthio)ethyl, phenylmethyl, 4-hydroxyphenylmethyl, 3-indolylmethyl, imidazolylmethyl, 3-aminopropyl, 3-(carbamoylamino)propyl, 2-hydroxyethyl, or 4-guanidinobutyl. The relationship between an amino acid, and $R^a$ and $R^b$ is illustrated in the following Table 1.

TABLE 1

Relationship between amino acid, and $R^a$ and $R^b$

| Amino acid | $R^a$ | $R^b$ |
| --- | --- | --- |
| Alanine | Hydrogen atom | Methyl |
| Valine | Hydrogen atom | 1-Methylethyl |
| Leucine | Hydrogen atom | 2-Methylpropyl |
| Isoleucine | Hydrogen atom | 1-Methylpropyl |
| Serine | Hydrogen atom | Hydroxymethyl |
| Threonine | Hydrogen atom | 1-Hydroxyethyl |
| Cysteine | Hydrogen atom | Sulfanylmethyl |
| Lysine | Hydrogen atom | 4-Aminobutyl |
| Arginine | Hydrogen atom | 3-Guanidinopropyl |
| Aspartic acid | Hydrogen atom | Carboxymethyl |
| Glutamic acid | Hydrogen atom | 2-Carboxyethyl |
| Asparagine | Hydrogen atom | Carbamoylmethyl |
| Glutamine | Hydrogen atom | 2-Carbamoylethyl |
| Methionine | Hydrogen atom | 2-(Methylthio)ethyl |
| Phenylalanine | Hydrogen atom | Phenylmethyl |
| Tyrosine | Hydrogen atom | 4-Hydroxyphenylmethyl |
| Tryptophan | Hydrogen atom | 3-Indolylmethyl |
| Histidine | Hydrogen atom | Imidazolylmethyl |
| Ornithine | Hydrogen atom | 3-Aminopropyl |
| Citrulline | Hydrogen atom | 3-(Carbamoylamino)propyl |
| Homoserine | Hydrogen atom | 2-Hydroxyethyl |
| Homoarginine | Hydrogen atom | 4-Guanidinobutyl |
| Proline | — | — |

In the aforementioned general formula (A-2), the ring C represents a five-membered or six-membered nitrogen-containing ring. Examples of the five-membered nitrogen-containing ring may include pyrrole, pyrrolidine, pyrroline, imidazolidine, imidazoline, pyrazolidine, and pyrazoline. Examples of the six-membered nitrogen-containing ring may include pyridine, piperidine, piperazine, and morpholine. The ring C is preferably a five-membered nitrogen-containing ring, more preferably pyrrolidine. When the ring C is pyrrolidine, the amino acid represented by the general formula (A-2) can be proline.

In the chiral amino acid, the amino group or the carboxyl group may be protected by a protecting group. The protecting group may include conventionally known protecting groups. Examples of the protecting group for carboxyl may include methyl, methoxymethyl, methylthiomethyl, benzyloxymethyl, tert-butyl, benzyl, trimethylsilyl, and tert-butyldimethylsilyl. Examples of the protecting group for amino may include methoxycarbonyl, trimethylsilylethyloxycarbonyl, tert-butyloxycarbonyl, benzyloxycarbonyl, formyl, acetyl, benzoyl, and 9-fluorenylmethoxycarbonyl.

Examples of the chiral carboxylic acid as the first compound and the second compound may include a carboxylic acid represented by the following formula (C-1).

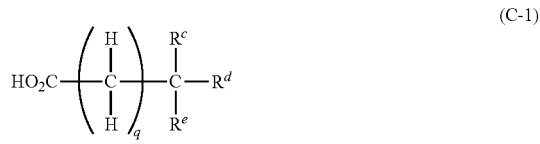

(C-1)

In the aforementioned general formula (C-1), $R^c$, $R^d$, and $R^e$ each independently represent a group selected from the group consisting of a hydrogen atom, a halogen atom, hydroxy, sulfanyl, guanidino, formyl, carbamoyl, carbamoylamino, cyano, $C_1$ to $C_6$ alkyl optionally substituted with one to three substituents which are the same as or different from each other, phenyl optionally substituted with one to three substituents which are the same as or different from each other, and heteroaryl optionally substituted with one to three substituents which are the same as or different from each other, provided that $R^c$, $R^d$, and $R^e$ are different from each other. The definitions and examples of atoms or groups represented by $R^c$, $R^d$, and $R^e$ are the same as the definitions and examples described on $R^a$ and $R^b$ of the chiral amino acid as the first compound and the second compound. q represents an integer of 0 to 3. Preferably, q represents an integer of 0, 1, or 2.

Preferably, $R^c$, $R^d$, and $R^e$ are each independently a hydrogen atom, hydroxy, or $C_1$ to $C_6$ alkyl (for example, methyl) optionally substituted with one to three substituents which are the same as or different from each other.

In a preferable specific embodiment, the first derivative and the second derivative are a compound in which the axially chiral compound of the present invention, which is a compound represented by the aforementioned formula (I), (I'), (II), (II'), (II-1), (II-1-1), (II-2), or (II-2-1), reacts with a chiral compound. Since the axially chiral compound of the present invention is novel, the derivative obtained by the reaction between the axially chiral compound of the present invention and a chiral compound is also considered novel. The present invention also provides a compound being such a derivative or a salt thereof. Examples of the salt are the same as those described on a salt of the novel axially chiral compound.

Specifically, the derivative of the present invention is a compound in which the reactive group in the compound represented by the aforementioned formula (I), (I'), (II), (II'), (II-1), (II-1-1), (II-2), or (II-2-1) reacts with a chiral compound to be converted into a specific group, for example, (a") a group represented by the general formula (i'), a group represented by the general formula (i"), a group represented by the general formula (ii'), or a group containing the group represented by the general formula (i'), (i"), or (ii'). When describing the derivative of the present invention, a sign "'" may be assigned to the number for the formula of the original axially chiral compound so that the derivative is distinguished from the axially chiral compound used in the method of the present invention.

The derivative of the present invention is preferably:
a compound in which the reactive group in the aforementioned formula (I') or (II') reacts with a chiral compound to be converted into a specific group, for example, (a") a group represented by the general formula (i'), a group represented by the general formula (i"), a group represented by the general formula (ii'), or a group containing the group represented by the general formula (i'), (i"), or (ii'),
the group having a charged atom or a chargeable atom is di($C_1$ to $C_6$ alkyl)amino, tri($C_1$ to $C_6$ alkyl)ammonio, a piperidino group, a morpholino group, or a group represented by the aforementioned general formula (d1) or the aforementioned general formula (d2), and
at least one of $R^1$ to $R^6$, $R^A$, and $R^B$ is the group having a charged atom or a chargeable atom; or
a compound in which the reactive group in the aforementioned formula (II-1), (II-1-1), (II-2), or (II-2-1) reacts with a chiral compound to be converted into a specific group, for example, (a") a group represented by the general formula (i'), a group represented by the general formula (i"), a group represented by the general formula (ii'), or a group containing the group represented by the general formula (i'), (i"), or (ii'), and
the group having a charged atom or a chargeable atom is di($C_1$ to $C_6$ alkyl)amino, tri($C_1$ to $C_6$ alkyl)ammonio, a piperidino group, a morpholino group, or a group represented by the aforementioned general formula (d1) or the aforementioned general formula (d2).

The group represented by the general formula (i') is as follows:

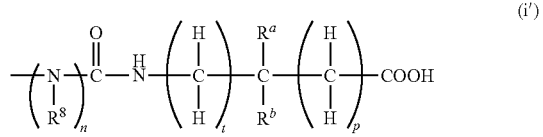

(i')

(wherein
$R^a$ and $R^b$ each independently represent an atom or a group selected from the group consisting of a hydrogen atom, a halogen atom, hydroxy, sulfanyl, guanidino, formyl, carbamoyl, carbamoylamino, cyano, $C_1$ to $C_6$ alkyl optionally substituted with one to three substituents which are the same as or different from each other, phenyl optionally substituted with one to three substituents which are the same as or different from each other, and heteroaryl optionally substituted with one to three substituents which are the same as or different from each other (provided that $R^a$ and $R^b$ are different from each other),
n represents 0 or 1,
$R^8$ does not exist when n is 0,
$R^8$ represents a hydrogen atom or a $C_1$ to $C_6$ alkyl group when n is 1,
t represents an integer of 0 to 3, and
p represents an integer of 0 to 3).

The definitions, examples, and preferable examples of $R^a$, $R^b$, t, and p in the general formula (i') are the same as those in the general formula (A-1). The $C_1$ to $C_6$ alkyl group represented by $R^8$ is the same as that previously described. n is preferably 1.

The group represented by the general formula (i") is as follows:

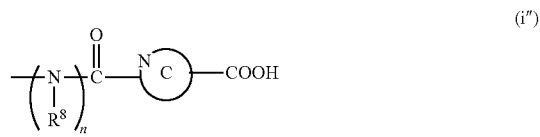

(i")

(wherein
ring C represents a five-membered or six-membered nitrogen-containing ring,
n represents 0 or 1,
$R^8$ does not exist when n is 0, and
$R^8$ represents a hydrogen atom or a $C_1$ to $C_6$ alkyl group when n is 1).

The definition, examples, and preferable examples of the ring C in the general formula (i") are the same as those in the general formula (A-2). The $C_1$ to $C_6$ alkyl group represented by $R^8$ is the same as that previously described. n is preferably 1.

The group represented by the general formula (ii') is as follows:

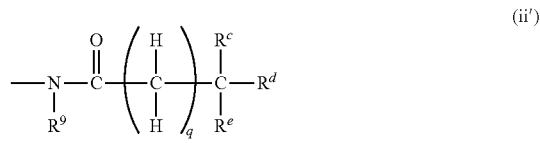

(ii')

(wherein
$R^9$ represents a hydrogen atom or a $C_1$ to $C_6$ alkyl group,
$R^c$, $R^d$, and $R^e$ each independently represent a group selected from the group consisting of a hydrogen atom, a halogen atom, hydroxy, sulfanyl, guanidino, formyl, carbamoyl, carbamoylamino, cyano, $C_1$ to $C_6$ alkyl optionally substituted with one to three substituents which are the same as or different from each other, phenyl optionally substituted with one to three substituents which are the same as or different from each other, and heteroaryl optionally substituted with one to three substituents which are the same as or different from each other, or amino (provided that, $R^c$, $R^d$, and $R^e$ are different from each other), and
q represents an integer of 0 to 3).

The definitions, examples, and preferable examples of $R^c$, $R^d$, $R^e$, and q in the general formula (ii') are the same as those in the general formula (C-1) except for amino. The $C_1$ to $C_6$ alkyl group represented by $R^e$ is the same as that previously described.

When any one of $R^c$, $R^d$, and $R^e$ represents amino, the amino may be protected by a protecting group.

Examples of the protecting group for amino may include those previously described.

Specific examples of the derivative according to the present invention may include compounds represented by the following formulae (201-1) to (207-1).

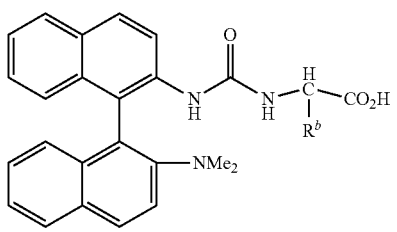
(201-1)
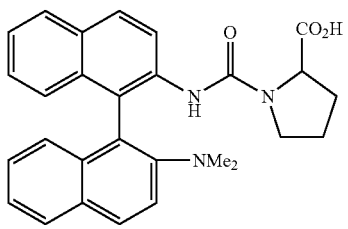
(201-2)
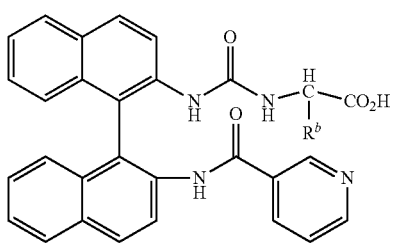
(202-1)
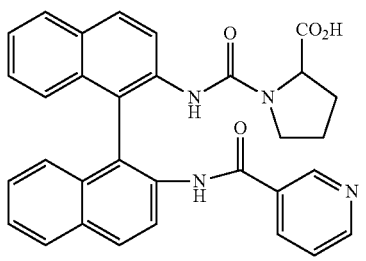
(202-2)
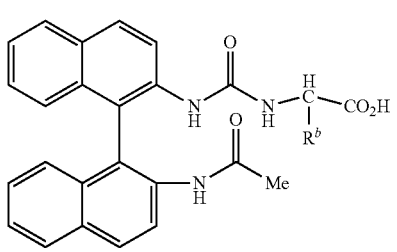
(203-1)
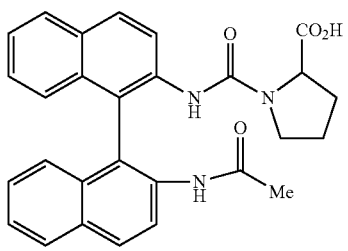
(203-2)
-continued
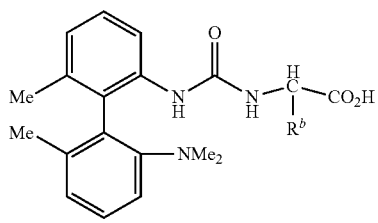
(204-1)
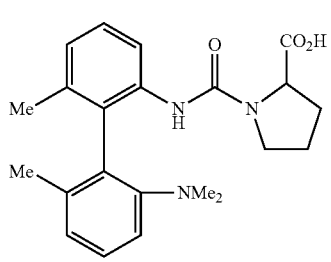
(204-2)
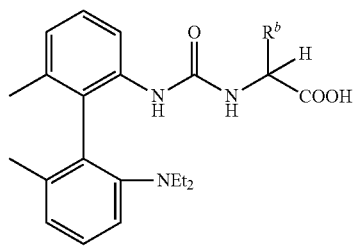
(205-1)
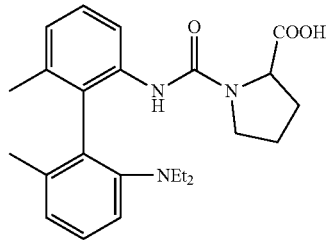
(205-2)
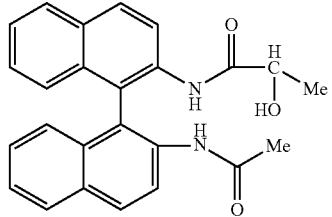
(206-1)
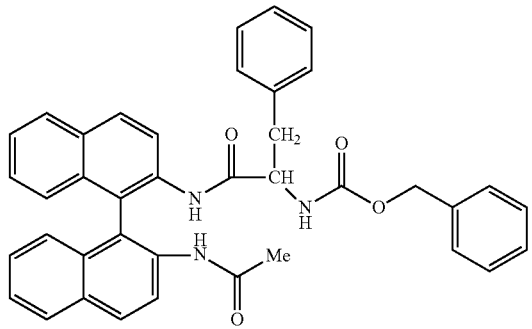
(206-2)

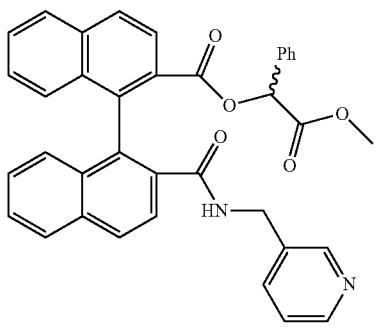

(207-1)

In the aforementioned formulae (201-1) to (206-2), $R^b$ represents methyl, 1-methylethyl, 2-methylpropyl, 1-methylpropyl, hydroxymethyl, 1-hydroxyethyl, sulfanylmethyl, 4-aminobutyl, 3-guanidinopropyl, carboxymethyl, 2-carboxyethyl, carbamoylmethyl, 2-carbamoylethyl, 2-(methylthio)ethyl, phenylmethyl, 4-hydroxyphenylmethyl, 3-indolylmethyl, or imidazolylmethyl.

A preferable embodiment of the compound represented by the general formula (I″) also includes tautomers of the compounds represented by the formulae (201-1) to (206-2). For example, the derivative of the present invention also includes a compound in which $R^b$ in the formulae (201-1) to (206-2) is imidazole-5-ylmethyl, and a compound in which $R^b$ in the formulae (201-1) to (206-2) is imidazole-4-ylmethyl.

Other features of the invention will become apparent in the course of the following descriptions of exemplary embodiments which are given for illustration of the invention and are not intended to be limiting thereof.

EXAMPLES

As described in the following examples, (R)-BDMA, (R)-BNCA, (R)-BACA, (R)-PDMA, (R)-PDEA, (R)—PNP-PDEA, and PBNA-TFA have the following chemical structures.

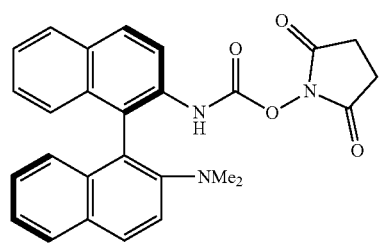

(R)-BDMA

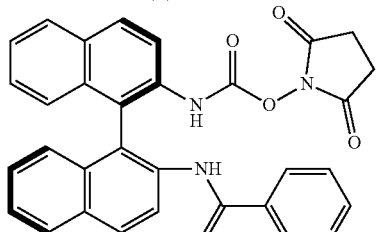

(R)-BNCA

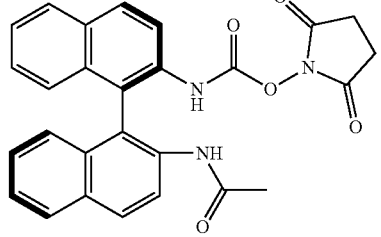

(R)-BACA

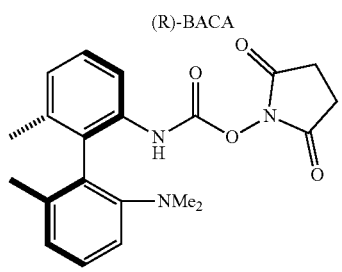

(R)-PDMA

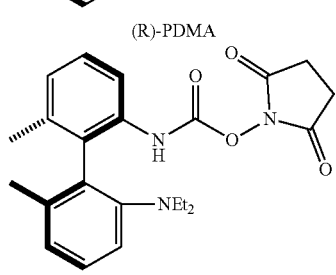

(R)-PDEA

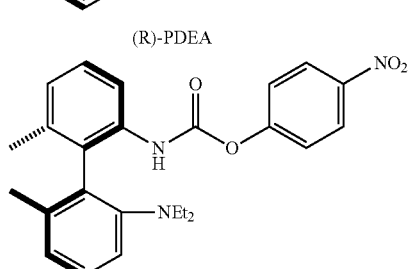

(R)-PNP-PDEA

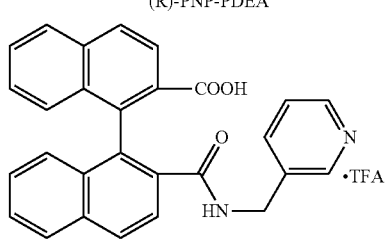

PBNA-TFA

Synthesis Example 1: Preparation of Axially Chiral Compound (R)-BDMA

In this synthesis example, an axially chiral compound (R)-BDMA was prepared by the following steps A to D.

Step A. Synthesis of (R)—N-(1-(2-aminonaphthalen-1-yl)naphthalen-2-yl)acetamide

Into a 50 mL round bottom flask, (R)-1,1'-binapthyl-2,2'-diamine (284 mg, 1.0 mmol, obtained from Sigma-Aldrich Corporation) and acetic acid (0.6 mL, 10 mmol) were charged, and dissolved in 10 mL of dichloromethane. Into this solution, acetic anhydride (104 mL, 1.0 mmol) was dropped using a pipetter while stirring in an ice bath. After stirring at room temperature overnight, approximately 5 mL of water was added, and a 1 mol/L sodium hydroxide aqueous solution was added to adjust the pH to approximately 7. The reaction was thus terminated. The target product was extracted from the solution with dichloromethane three times, and the organic layer was washed with brine once. Then, the organic layer was dried with sodium sulfate, and the solvent was distilled away under reduced pressure. Accordingly, a crude product was obtained. The crude product was purified by silica gel column chromatography. Thus, a target white crystal of (R)—N-(1-(2-aminonaphthalen-1-yl)naphthalen-2-yl)acetamide was obtained with a yield of 78% (253 mg).

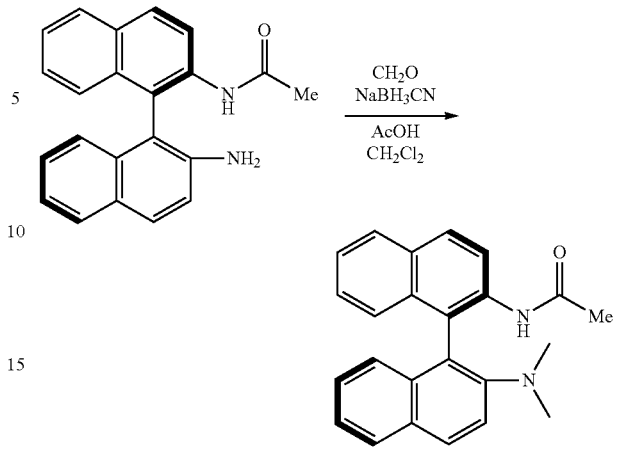

$^1$H NMR (CDCl$_3$, 400 MHz): δ 8.48 (d, J=8.9 Hz, 1H), 7.95 (dd, J=8.9, 2.3 Hz, 2H), 7.90-7.77 (m, 2H), 7.53 (br, 1H), 7.48 (d, J=9.0 Hz, 1H), 7.40-7.08 (m, 5H), 6.93 (d, J=8.6 Hz, 1H), 2.55 (s, 6H), 1.84 (s, 3H).

Step C. Synthesis of (R)-1-(2-(dimethylamino) naphthalen-1-yl)naphthalen-2-amine Into a 50 mL round bottom flask, the (R)—N-(1-(2-(dimethylamino)naphthalen-1-yl)naphthalen-2-yl)acetamide (217 mg, 0.611 mmol) obtained in Step B was charged, and suspended in 20 mL of ethanol. A 6 mL portion of 6 mol/L hydrochloric acid was added.

After 5 hours, 5 mL of concentrated hydrochloric acid was further added. After stirring at room temperature for approximately 70 hours, water and sodium hydroxide were added to the resultant product in an ice bath to obtain a basic aqueous solution. Thereafter, extraction was performed with 20 mL of dichloromethane three times. The organic layer was washed with brine once, and dried with sodium sulfate. The solvent was distilled away under reduced pressure to obtain a crude product. The obtained crude product was purified by silica gel column chromatography. Thus, (R)-1-(2-(dimethylamino)naphthalen-1-yl)naphthalen-2-amine was obtained as a reddish brown solid with a yield of 59% (113 mg).

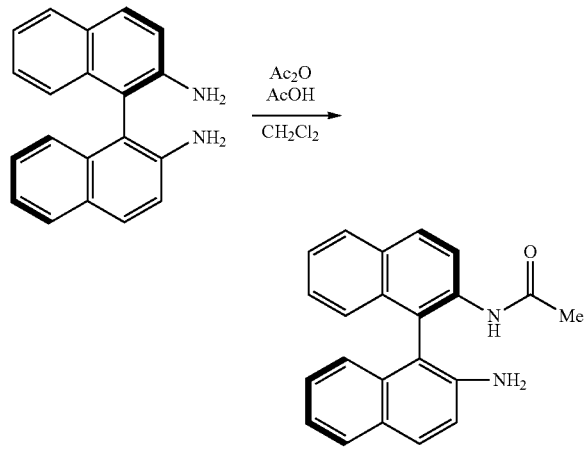

$^1$H NMR (CDCl$_3$, 400 MHz): δ 8.60 (d, J=9.1 Hz, 1H), 7.98 (d, J=9.0 Hz, 1H), 7.89 (dt, J=8.1, 0.9 Hz, 1H), 7.86-7.76 (m, 2H), 7.39 (ddd, J=8.2, 6.7, 1.3 Hz, 1H), 7.27-7.08 (m, 5H), 7.04 (br, 1H), 6.90 (d, J=8.3 Hz, 1H), 3.65 (s, 2H), 1.82 (s, 3H).

Step B. Synthesis of (R)—N-(1-(2-(dimethylamino) naphthalen-1-yl)naphthalen-2-yl)acetamide Into a 50 mL round bottom flask, the (R)—N-(1-(2-aminonaphthalen-1-yl)naphthalen-2-yl)acetamide (210 mg, 0.644 mmol) obtained in Step A and an approximately 36% formaldehyde aqueous solution (0.75 mL, 9.0 mmol) were charged, and dissolved in 10 mL of tetrahydrofuran. After stirring for 15 minutes, NaBH$_3$CN (200 mg, 3.1 mmol) was added, and 1.0 mL of acetic acid was slowly dropped. After stirring for 4 hours, the pH was adjusted to approximately pH 7 with a 1 mol/L sodium hydroxide aqueous solution. Extraction was performed with approximately 10 mL of dichloromethane three times. The organic layer was dried with sodium sulfate, and the solvent was distilled away under reduced pressure. Accordingly, a crude product was obtained. The obtained crude product was purified by silica gel column chromatography.

Thus, a target white, solid product was obtained with a yield of 95% (217 mg).

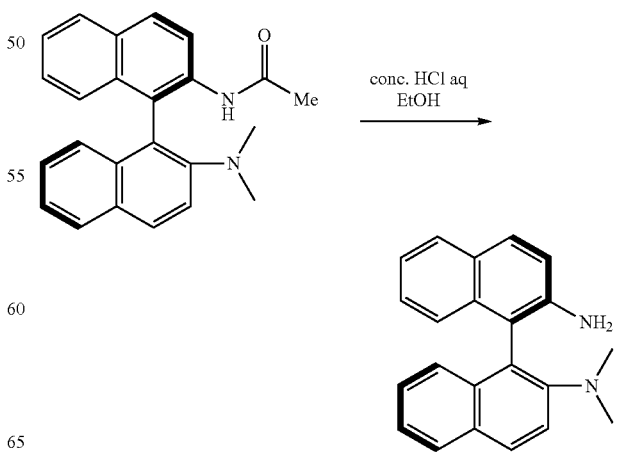

¹H NMR (CDCl₃, 400 MHz): δ 7.85 (d, J=8.9 Hz, 1H), 7.80-7.65 (m, 3H), 7.42 (d, J=9.0 Hz, 1H), 7.28-7.06 (m, 5H), 7.01 (d, J=8.7 Hz, 2H), 3.58 (br, 1H), 2.55 (s, 6H).

Step D. Synthesis of (R)-BDMA

Into a 10 mL round bottom flask, the (R)-1-(2-(dimethylamino)naphthalen-1-yl)naphthalen-2-amine (113.2 mg, 0.362 mmol) obtained in Step C was charged. Then, dichloromethane was added, and the (R)-1-(2-(dimethylamino)naphthalen-1-yl)naphthalen-2-amine was dissolved in dichloromethane. Furthermore, 1 equivalent of N,N'-disuccinimidyl carbonate (DSC) was added to initiate a reaction at room temperature. After stirring overnight, the solvent was distilled away under reduced pressure. Thus, (R)-BDMA was obtained. The obtained carbamate was checked for its purity by ¹H NMR, and then used as the axially chiral compound without performing purification.

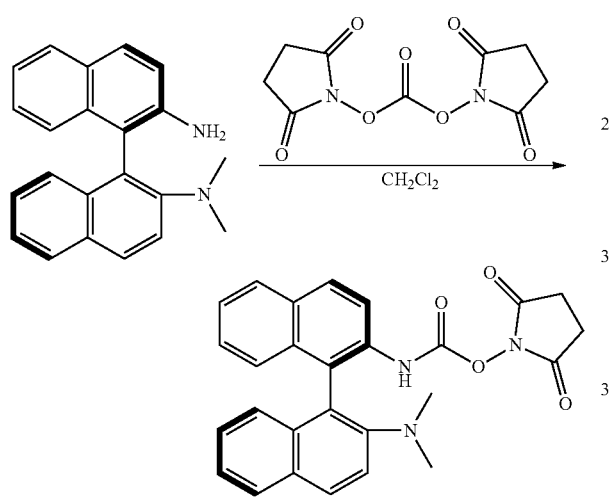

¹H NMR (CDCl₃, 400 MHz): δ 8.22 (d, J=9.0 Hz, 1H), 7.98 (d, J=9.0 Hz, 2H), 7.89 (d, J=8.1 Hz, 1H), 7.84 (d, J=8.0 Hz, 1H), 7.65 (br, 1H), 7.54 (d, J=9.0 Hz, 1H), 7.40 (m, 1H), 7.32 (m, 1H), 7.27-7.20 (m, 1H), 7.19-7.10 (m, 2H), 6.90 (d, J=8.5 Hz, 1H), 2.71 (s, 4H), 2.61 (s, 6H).

Synthesis Example 2: Preparation of Axially Chiral Compound (R)-BNCA

In this synthesis example, an axially chiral compound (R)-BNCA was prepared by the following steps E to G.

Step E. Synthesis of (R)—N-[1-(2-acetamidonaphthalen-1-yl)naphthalen-2-yl]pyridine-3-carboxamide Into a 50 mL round bottom flask, the (R)—N-(1-(2-aminonaphthalen-1-yl)naphthalen-2-yl)acetamide (48 mg, 0.27 mmol) obtained in Step A of Synthesis Example 1 was charged. Then, dehydrated tetrahydrofuran was added, and the (R)—N-(1-(2-aminonaphthalen-1-yl)naphthalen-2-yl)acetamide was dissolved in dehydrated tetrahydrofuran. Triethylamine (approximately 10 mL, approximately 0.4 mmol) and nicotinoyl chloride hydrochloride (80 mg, 0.25 mmol) were added. The mixture was stirred at room temperature for 4 days. The reaction product was suspended in water and a saturated sodium hydrogen carbonate aqueous solution. Extraction was performed with 10 mL of dichloromethane three times. The organic layer was dried with sodium sulfate, and the solvent was distilled away under reduced pressure. Accordingly, a crude product was quantitatively obtained as a white crystal (119 mg).

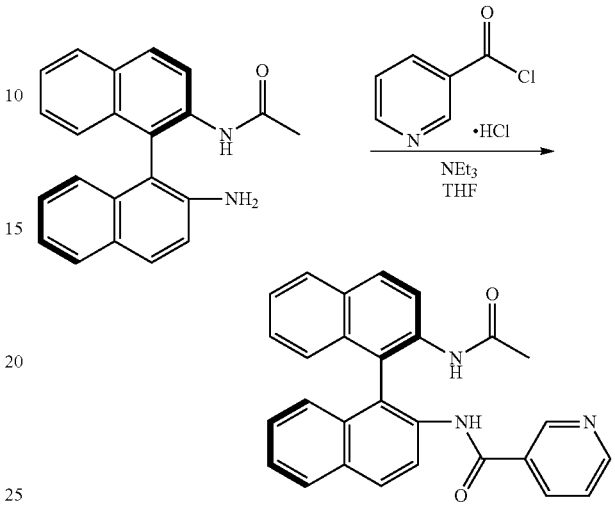

¹H NMR (CDCl₃, 400 MHz): δ 8.62 (s, 1H), 8.38-8.33 (m, 1H), 8.24 (dd, J=4.9, 1.7 Hz, 1H), 8.11 (d, J=8.9 Hz, 1H), 7.97 (d, J=9.0 Hz, 2H), 7.87 (t, J=9.2 Hz, 2H), 7.80 (d, J=8.2 Hz, 1H), 7.71 (ddd, J=7.9, 2.4, 1.7 Hz, 1H), 7.68 (s, 1H), 7.46-7.30 (m, 2H), 7.24-7.12 (m, 2H), 7.09-6.98 (m, 3H), 1.80 (s, 3H).

Step F. Synthesis of (R)—N-[1-(2-aminonaphthalen-1-yl)naphthalen-2-yl]pyridine-3-carboxamide Into a 20 mL flask, the (R)—N-[1-(2-acetamidonaphthalen-1-yl)naphthalen-2-yl]pyridine-3-carboxamide (119 mg, 0.276 mmol) obtained in Step E was charged, and dissolved in 1 mL of ethanol. Then, 1 mL of concentrated hydrochloric acid was added, and the solution was stirred at room temperature for 2 days. The resultant product was adjusted to be basic with an 8 mol/L sodium hydroxide aqueous solution. Extraction was performed with 5 mL of dichloromethane three times. The organic layer was dried with sodium sulfate. Thereafter, the solvent was distilled away under reduced pressure. Accordingly, a crude product was obtained. The obtained crude product was purified by silica gel column chromatography. Thus, the target product was obtained as a white solid with a yield of 38% (41.0 mg).

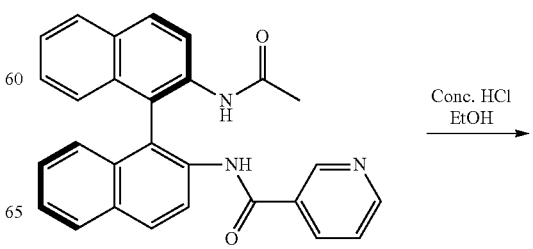

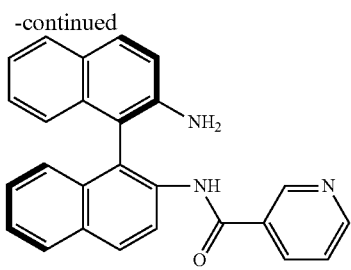

¹H NMR (CDCl₃, 400 MHz): δ 8.82 (d, J=9.0 Hz, 1H), 8.55 (dd, J=4.9, 1.7 Hz, 1H), 8.39-8.33 (m, 1H), 8.06 (d, J=9.0 Hz, 1H), 8.00-7.90 (m, 2H), 7.92-7.77 (m, 2H), 7.69 (dt, J=7.9, 2.0 Hz, 1H), 7.50-7.38 (m, 1H), 7.37-7.11 (m, 5H), 7.00-6.93 (m, 1H), 3.77 (br, 2H).

Step G. Synthesis of (R)-BNCA

Into a 10 mL round bottom flask, the (R)—N-[1-(2-aminonaphthalen-1-yl)naphthalen-2-yl]pyridine-3-carboxamide (41.0 mg, 0.105 mmol) obtained in Step F was charged. Then, dichloromethane was added, and the (R)—N-[1-(2-aminonaphthalen-1-yl)naphthalen-2-yl]pyridine-3-carboxamide was dissolved in dichloromethane. Furthermore, 1 equivalent of DSC was added to initiate a reaction at room temperature. After stirring overnight, the solvent was distilled away under reduced pressure. Thus, (R)-BNCA was obtained. The obtained carbamate was checked for its purity by ¹H NMR, and then used as the axially chiral compound without performing purification.

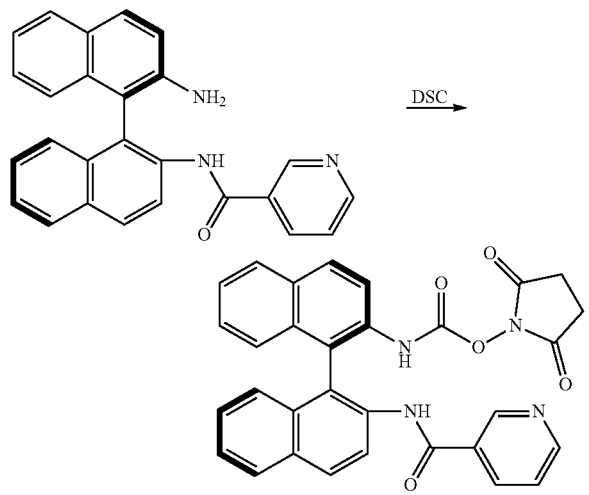

¹H NMR (CDCl₃, 400 MHz): δ 8.82 (d, J=9.0 Hz, 1H), 8.55 (dd, J=4.9, 1.7 Hz, 1H), 8.39-8.33 (m, 1H), 8.06 (d, J=9.0 Hz, 1H), 8.00-7.90 (m, 2H), 7.92-7.77 (m, 2H), 7.69 (dt, J=7.9, 2.0 Hz, 1H), 7.50-7.38 (m, 1H), 7.37-7.11 (m, 5H), 7.00-6.93 (m, 1H), 3.77 (br, 2H).

Synthesis Example 3: Preparation of Axially Chiral Compound (R)-BACA

In this synthesis example, an axially chiral compound (R)-BACA was prepared.

Into a 10 mL round bottom flask, the N-(1-(2-aminonaphthalen-1-yl)naphthalen-2-yl)acetamide (95.0 mg, 0.291 mmol) obtained in Step A of Synthesis Example 1 was charged. Then, dichloromethane was added, and the N-(1-(2-aminonaphthalen-1-yl)naphthalen-2-yl)acetamide was dissolved in dichloromethane. Furthermore, 1 equivalent of DSC was added to initiate a reaction at room temperature. After stirring overnight, the solvent was distilled away under reduced pressure. Thus, (R)-BACA was obtained. The obtained (R)-BACA was checked for its purity by ¹H NMR, and then used as the axially chiral compound without performing purification.

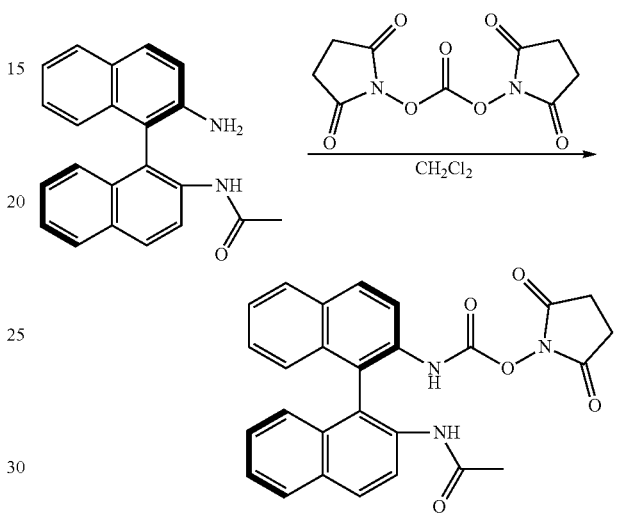

¹H NMR (CDCl₃, 400 MHz): δ 8.44-8.35 (m, 2H), 8.19 (s, 1H), 8.13-8.01 (m, 2H), 7.99-7.90 (m, 2H), 7.89-7.78 (m, 3H), 7.45-7.31 (m, 2H), 7.27-7.13 (m, 3H), 7.06-6.91 (m, 3H), 2.68 (s, 4H).

Synthesis Example 4: Preparation of Axially Chiral Compound (R)-PDMA

In this synthesis example, an axially chiral compound (R)-PDMA was prepared.

Step A. Synthesis of (R)-2-(2-amino-6-methylphenyl)-N,N,3-trimethylaniline

In a 25 mL round bottom flask, (R)-6,6'-dimethyl-2,2'-biphenyldiamine (212 mg, 1.0 mmol, obtained from Sigma-Aldrich Corporation) and acetic acid (0.6 mL, 10 mmol) were dissolved in 10 mL of dichloromethane. Acetic anhydride (104 mL, 1.0 mmol) was dropped using a pipetter while stirring in an ice bath. After stirring at room temperature overnight, approximately 5 mL of water was added, and a 1 mol/L sodium hydroxide aqueous solution was added to adjust the pH to approximately 7. The reaction was terminated. The target product was extracted from the solution with dichloromethane three times, and the organic layer was washed with brine once. Then, the organic layer was dried with sodium sulfate, and the solvent was distilled away under reduced pressure. Accordingly, a crude product of (R)—N-(2-(2-amino-6-methylphenyl)-3-methylphenyl)acetamide was obtained. Into 52.9 mg of the crude product, 0.4 mL of an approximately 36% formaldehyde aqueous solution (4.8 mmol) was dropped. The mixture was stirred for 15 minutes. Thereafter, NaBH₃CN (100 mg, 1.6 mmol) was added. After stirring for 5 minutes, 0.5 mL of acetic acid was slowly dropped. The mixture was stirred at room temperature overnight. After the pH was adjusted to approximately pH 7 with a 1 mol/L sodium hydroxide aqueous solution, extraction was performed with approximately 10 mL of dichloromethane three times. The organic layer was dried with sodium sulfate, and the solvent was distilled away under reduced pressure. Accordingly, a crude product of (R)—N-(2-(2-dimethylamino-6-methylphenyl)-3-methylphenyl)acetamide was obtained. To this crude product, 1 mL of saturated hydrochloric acid was further added. The mixture was stirred for 3 days, and neutralized with sodium hydroxide. Thereafter, extraction was performed with 10 mL of dichloromethane three times. The obtained dichloromethane solution was dried with sodium sulfate, and the solvent was distilled away under reduced pressure. Accordingly, a crude product was obtained. The crude product was purified by silica gel column chromatography. Thus, 18.8 mg of the product was obtained.

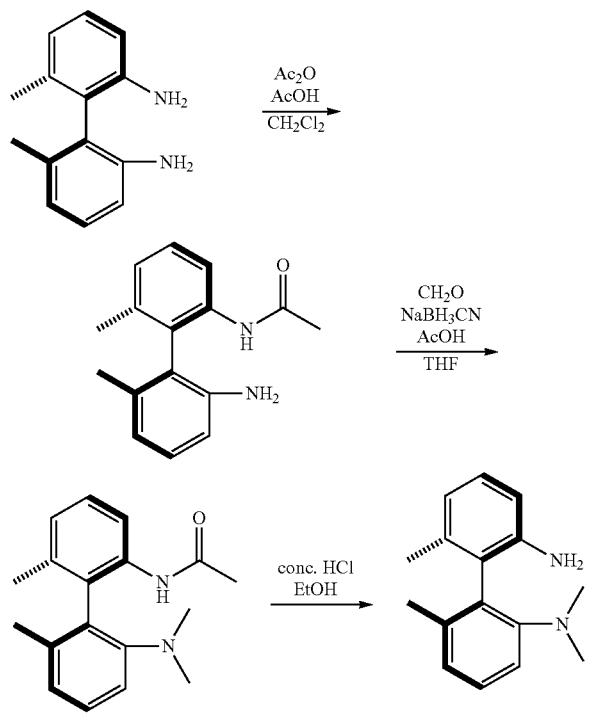

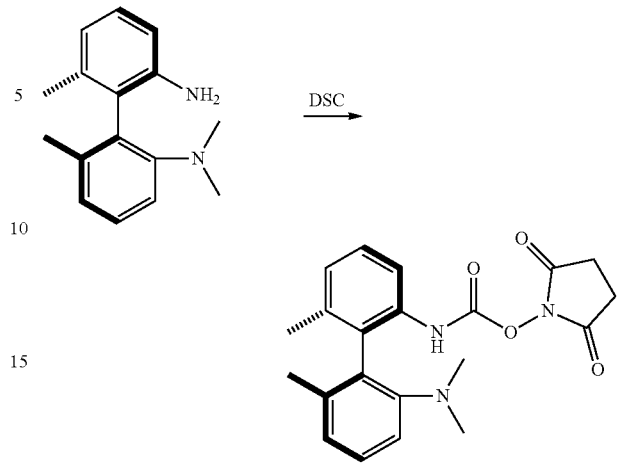

$^1$H NMR (CDCl$_3$, 400 MHz): δ 7.80 (d, J=7.9 Hz, 1H), 7.32-7.25 (m, 2H), 7.14-7.08 (m, 1H), 7.04-6.97 (m, 2H), 2.80 (s, 4H), 2.52 (s, 6H), 2.03 (s, 3H), 1.93 (s, 3H).

Synthesis Example 5: Preparation of (R)-PDEA

In this synthesis example, an axially chiral compound (R)-PDEA was prepared.

Step A. Synthesis of 2-(2-amino-6-methylphenyl)-N,N-diethyl-3-methylaniline

Into 74.5 mg of the crude product of (R)—N-(2-(2-amino-6-methylphenyl)-3-methylphenyl)acetamide obtained as an intermediate product in Step A of Synthesis Example 4, 0.5 mL (8.9 mmol) of acetaldehyde was dropped. After stirring for 15 minutes, NaBH$_3$CN (92 mg, 1.46 mmol) was added. After stirring for 5 minutes, 0.5 mL of acetic acid was slowly dropped. The mixture was stirred at room temperature overnight. After the pH was adjusted to approximately pH 7 with a 1 mol/L sodium hydroxide aqueous solution, extraction was performed with approximately 10 mL of dichloromethane three times. The organic layer was dried with sodium sulfate, and the solvent was distilled away under reduced pressure. Accordingly, a crude product of (R)—N-(2-(2-diethylamino-6-methylphenyl)-3-methylphenyl)acetamide was obtained. To this crude product, 1 mL of saturated hydrochloric acid was further added. The mixture was stirred overnight, and neutralized with sodium hydroxide. Thereafter, extraction was performed with 10 mL of dichloromethane three times. The obtained dichloromethane solution was dried with sodium sulfate, and the solvent was distilled away under reduced pressure. Accordingly, a crude product was obtained. The crude product was purified by silica gel column chromatography. Thus, 22.3 mg of the product was obtained.

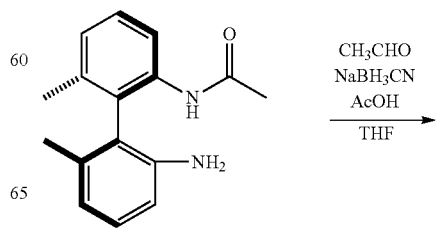

$^1$H NMR (CDCl$_3$, 400 MHz): δ 7.21 (t, J=7.8 Hz, 1H), 7.05 (t, J=7.7 Hz, 1H), 6.93 (d, J=7.9 Hz, 2H), 6.70 (dt, J=7.5, 1.0 Hz, 1H), 6.60 (dd, J=7.9, 1.1 Hz, 1H), 3.40 (br, 2H), 2.54 (s, 6H), 1.97 (s, 3H), 1.91 (s, 3H).

Step B. Synthesis of (R)-PDMA

Into a 25 mL round bottom flask, the (R)-2-(2-amino-6-methylphenyl)-N,N,3-trimethylaniline obtained in Step A of Synthesis Example 4 was charged, and 1 equivalent of DSC was added. The mixture was stirred overnight. After stirring overnight, the solvent was distilled away under reduced pressure. Thus, (R)-PDMA was obtained. The obtained (R)-PDMA was checked for its purity by $^1$H NMR, and then used as the axially chiral compound without performing purification.

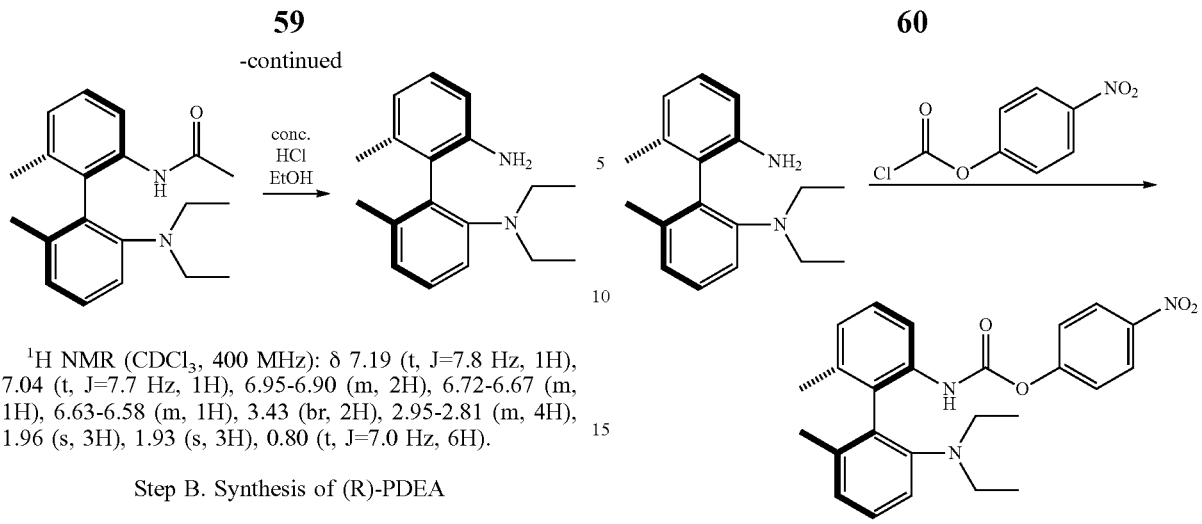

$^1$H NMR (CDCl$_3$, 400 MHz): δ 7.19 (t, J=7.8 Hz, 1H), 7.04 (t, J=7.7 Hz, 1H), 6.95-6.90 (m, 2H), 6.72-6.67 (m, 1H), 6.63-6.58 (m, 1H), 3.43 (br, 2H), 2.95-2.81 (m, 4H), 1.96 (s, 3H), 1.93 (s, 3H), 0.80 (t, J=7.0 Hz, 6H).

Step B. Synthesis of (R)-PDEA

Into a 25 mL round bottom flask, the 2-(2-amino-6-methylphenyl)-N,N-diethyl-3-methylaniline obtained in Step A of Synthesis Example 5 was charged, and 1 equivalent of DSC was added. The mixture was stirred overnight. After stirring overnight, the solvent was distilled away under reduced pressure. Thus, (R)-PDEA was obtained. The obtained (R)-PDMA was checked for its purity by $^1$H NMR, and then used as the axially chiral compound without performing purification.

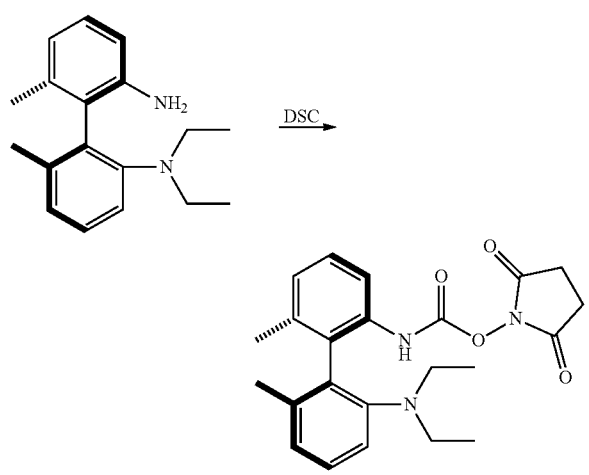

$^1$H NMR (CDCl$_3$, 400 MHz): δ 7.84 (d, J=8.2 Hz, 1H), 7.35-7.21 (m, 3H), 7.10 (d, J=7.6 Hz, 1H), 7.00 (dd, J=7.9, 4.7 Hz, 2H), 6.54 (br, 2H), 2.98-2.75 (m, 8H), 2.02 (s, 3H), 1.92 (s, 3H), 0.86 (t, J=7.1 Hz, 6H).

Synthesis Example 6: Synthesis of (R)—PNP-PDEA

In this synthesis example, an axially chiral compound (R)—PNP-PDEA was prepared.

Into a 25 mL round bottom flask, the 2-(2-amino-6-methylphenyl)-N,N-diethyl-3-methylaniline obtained in Step A of Synthesis Example 5 was charged, and 1 equivalent of 4-nitrophenyl chloroformate was added. The mixture was stirred overnight. After stirring overnight, the solvent was distilled away under reduced pressure. Thus, (R)—PNP-PDEA was obtained. The obtained (R)—PNP-PDMA was checked for its purity by $^1$H NMR, and then used as the axially chiral compound without performing purification.

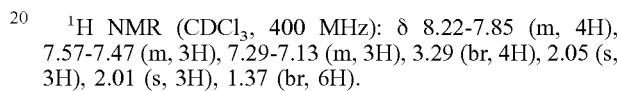

$^1$H NMR (CDCl$_3$, 400 MHz): δ 8.22-7.85 (m, 4H), 7.57-7.47 (m, 3H), 7.29-7.13 (m, 3H), 3.29 (br, 4H), 2.05 (s, 3H), 2.01 (s, 3H), 1.37 (br, 6H).

Synthesis Example 7: Synthesis of Chiral PBNA-TFA

In this synthesis example, an axially chiral compound chiral PBNA-TFA was prepared.

Synthesis of 1-(2-((Pyridin-3-yl)methylcarbamoyl) naphthalen-1-yl)naphthalene-2-carboxylic acid (PBNA)

By referring to the following literature, (1,1'-binaphthalene)-2,2'-dicarboxylic acid was synthesized with 1-bromo-2-naphthoic acid (supplied from Tokyo Chemical Industry Co., Ltd.) as a raw material. Literature: Synthesis, 2000, Vol. 2000, pp. 1677-1680, which is incorporated herein by reference in its entirety.

Into a 50 mL round bottom flask, 101 mg (0.295 mmol) of the synthesized (1,1'-binaphthalene)-2,2'-dicarboxylic acid was charged, and picolylamine (38.3 mg, 0.354 mmoL, 1.2 equivalents), N,N'-dicyclohexylcarbodiimide (63.9 mg, 0.310 mmoL, 1.05 equivalents), triethylamine (275 mg, 2.71 mmol, 9.2 equivalents), and THF (10 mL) were added. The mixture was stirred at 45° C. overnight. The reaction liquid was concentrated under reduced pressure to obtain 1-(2-((pyridin-3-yl)methylcarbamoyl)naphthalen-1-yl)naphthalene-2-carboxylic acid (PBNA) as a crude product.

Synthesis of PBNA-TFA

The obtained crude product was fractionated and purified by silica gel column chromatography (dichloromethane:methanol=95:5 to 50:50) and by reverse phase preparative HPLC (0.1% TFA aqueous solution:0.1% TFA acetonitrile solution=85:15 to 40:60). Accordingly, 95 mg of a trifluoroacetic acid salt of PBNA (PBNA-TFA) was obtained.

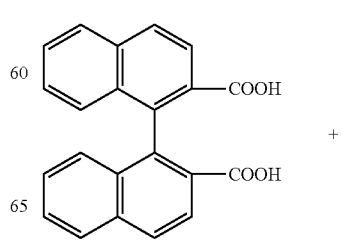

-continued

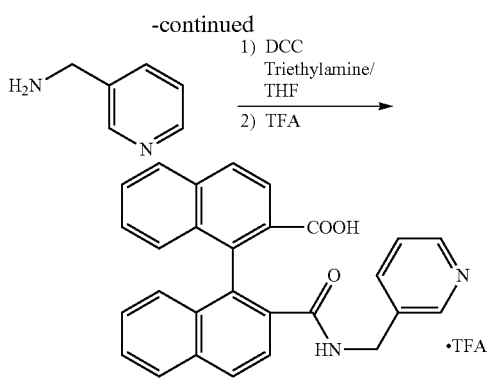

$^1$H NMR (Methanol-d$_4$, 400 MHz): δ 8.53 (t, J=3.5 Hz, 1H), 8.27 (br, 1H), 8.11-7.91 (m, 5H), 7.74 (d, J=8.5 Hz, 1H), 7.58-7.38 (m, 4H), 7.22 (tdd, J=8.6, 6.8, 1.2 Hz, 2H), 6.98 (ddd, J=13.9, 8.6, 1.1 Hz, 2H), 4.46 (d, J=15.2 Hz, 1H), 4.22 (d, J=15.2 Hz, 1H).

Optical Resolution of PBNA-TFA (Preparation of (R)- or (S)-PBNA-TFA)

After a sample was dissolved in an ethanol.hexane (1/1) solution, fractionation was performed in the following condition. Accordingly, a component having been eluted during a retention time of 9 to 13 minutes and a component having been eluted during a retention time of 15 to 20 minutes were separated. The component having been eluted during a retention time of 15 to 20 minutes was recovered, and the solvent was distilled away under reduced pressure. Thus, a trifluoroacetic acid salt of (R)- or (S)-PBNA ((R)- or (S)-PBNA-TFA) was obtained (the absolute configuration is undetermined, hereinafter referred to as chiral PBNA-TFA). The obtained compound was used as a derivatizing agent for a chiral alcohol in Example 5.

Column: CHIRAL ART Amylose-C manufactured by YMC Co., Ltd., (5 μm) 250×30 mm (ID)
Mobile phase: hexane/ethanol/trifluoroacetic acid (50/50/0.1)
Flow velocity: 21.3 mL/min
Column temperature: room temperature
UV detection wavelength: 225 nm
Preparative system: LC-Forte/R manufactured by YMC Co., Ltd.

Synthesis Example 8: Synthesis of Axially Chiral Compound (8b)

An axially chiral compound (8b) is synthesized in a similar manner to that in Synthesis Example 1, except that propanal is used in place of formaldehyde in Step B of Synthesis Example 1.

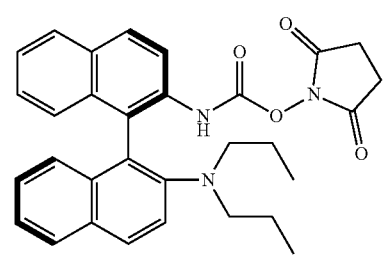

(8b)

Synthesis Example 9: Synthesis of Axially Chiral Compound (9b)

An axially chiral compound (9b) is synthesized with the following compound (9a) as a raw material in a similar manner to that in Step D of Synthesis Example 1.

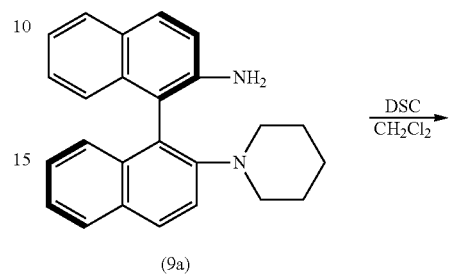

(9a)

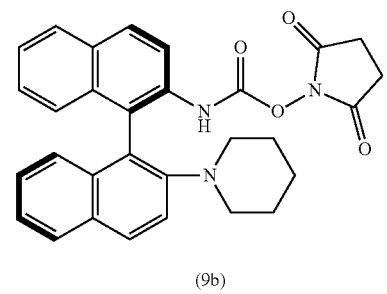

(9b)

Synthesis Example 10: Synthesis of Axially Chiral Compound (10b)

An axially chiral compound (10b) is synthesized with the following compound (10a) as a raw material in a similar manner to that in Step D of Synthesis Example 1.

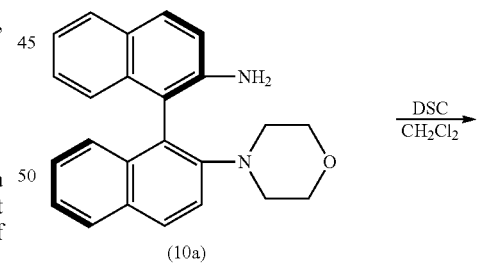

(10a)

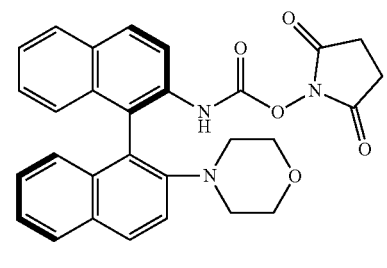

(10b)

Synthesis Example 11: Synthesis of Axially Chiral Compound (11 b)

An axially chiral compound (11b) is synthesized in a similar manner to that in Synthesis Example 4, except that propanal is used in place of formaldehyde in Step A of Synthesis Example 4.

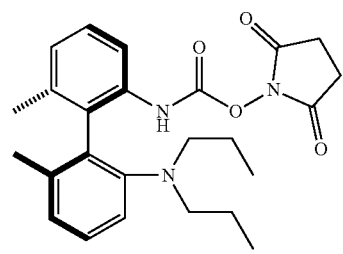

(11b)

Synthesis Example 12: Synthesis of Axially Chiral Compound (12b)

An axially chiral compound (12b) is synthesized with the following compound (12a) as a raw material in a similar manner to that in Step B of Synthesis Example 4.

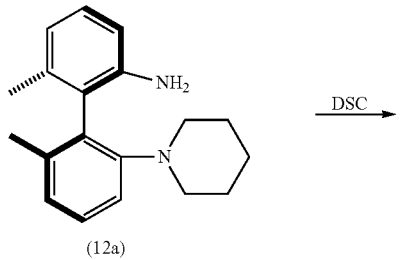

(12a)

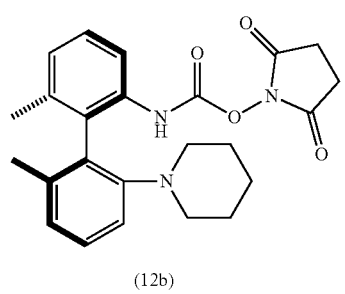

(12b)

Synthesis Example 13: Synthesis of Axially Chiral Compound (13b)

An axially chiral compound (13b) is synthesized with the following compound (13a) as a raw material in a similar manner to that in Step B of Synthesis Example 4.

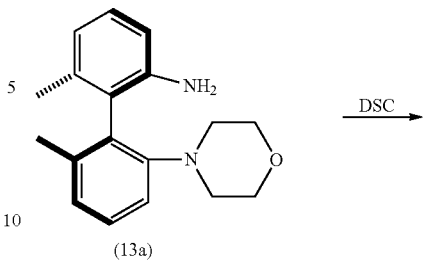

(13a)

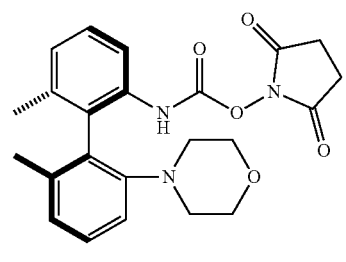

(13b)

Example 1: Analysis Method of Chiral Amino Acid 1-1) Preparation of Axially Chiral Compound Solution Into a 5 mL vial, approximately 10 mg of an axially chiral compound was weighted and charged, and acetonitrile was added so that the concentration of the axially chiral compound became approximately 10 mmol/L. The mixture was thoroughly stirred to obtain an axially chiral compound solution.

1-2) Derivatization of Mixture of Chiral Amino Acid (D Form and L Form)

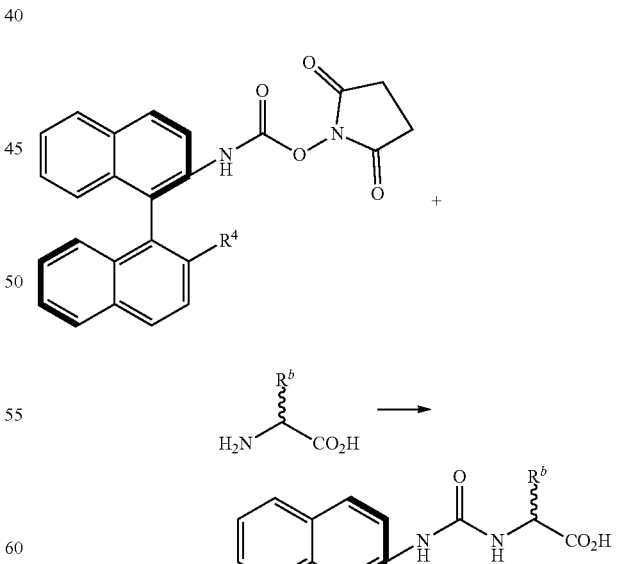

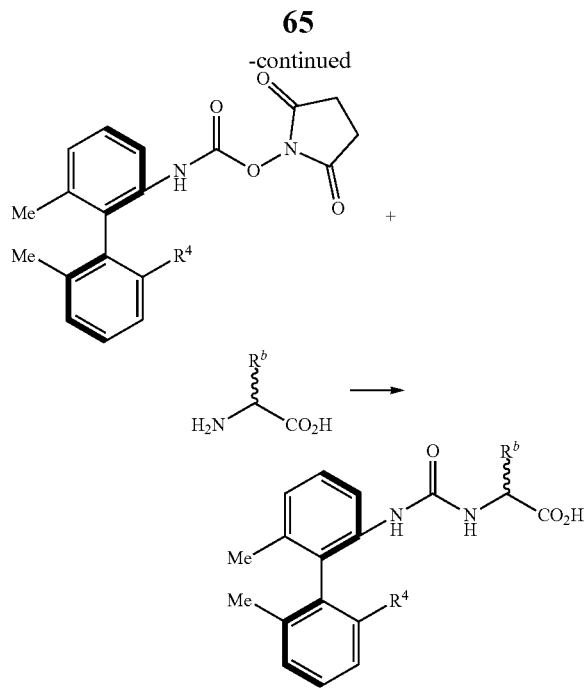

To 20 μL of a 200 mmol/L boric acid buffer and 40 μL of acetonitrile, 10 μL of a chiral amino acid (D form and L form) mixed solution (a mixture of L form (10 μmon) and D form (1 μmol/L)) was added. The mixture was stirred using a vortex mixer. Into the mixture, 104 of the axially chiral compound solution was added, and stirred using a vortex mixer. Thereafter, the resultant product was left to stand at room temperature or at 55° C. for 10 minutes. After the termination of the reaction, 120 μL of a 0.1% formic acid aqueous solution was added. Accordingly, a derivative mixture of the first derivative of a chiral amino acid (D form) and the second derivative of a chiral amino acid (L form) was obtained.

1-3) Separation and Detection of First Derivative and Second Derivative

The first derivative and the second derivative contained in the sample solution were separated by reverse phase high performance liquid column chromatography. The condition is as follows.

Column: Acquity UPLC (registered trademark) BEH-Phenyl manufactured by Waters, 1.7 μm (2.1×50 mm, 186002884) (this column is a hydrophobic column used for hydrophobic chromatography)
Temperature: 40° C.
Mobile phase A: 0.1% formic acid aqueous solution
Mobile phase B: acetonitrile The flow condition of the mobile phases when (R)-BDMA, (R)-BNCA, and (R)-BACA were used as the axially chiral compound is shown in Table 2. The flow condition of the mobile phases when (R)-PDMA and (R)-PDEA were used as the axially chiral compound is shown in Table 3.

TABLE 2

| | Flow condition 1 | | |
|---|---|---|---|
| Min | Flow Rate (μL/min) | % A | % B |
| 0 | 200 | 80 | 20 |
| 19 | 200 | 25 | 75 |
| 20 | 200 | 5 | 95 |
| 24 | 200 | 5 | 95 |
| 25 | 200 | 80 | 20 |
| 30 | 200 | 80 | 20 |

TABLE 3

| | Flow condition 2 | | |
|---|---|---|---|
| min | Flow Rate (μL/min) | % A | % B |
| 0 | 200 | 95 | 5 |
| 19 | 200 | 50 | 50 |
| 20 | 200 | 5 | 95 |
| 24 | 200 | 5 | 95 |
| 25 | 200 | 95 | 5 |
| 30 | 200 | 95 | 5 |

Detection was performed by mass spectrometry using a mass spectrometer (3200 QTrap manufactured by Sciex). The setting parameters of the mass spectrometer and the like are as follows.

Setting of Autosampler
Injection Volume: 3 μL
Autosampler Temperature: 4° C.
Parameter Setting of Ion Source
Ionization Method: ESI (positive ion mode)
Curtain Gas: 30
Collision Gas Setting: 4
Ion Spray Voltage: 5000
Temperature: 500
Ion Source Gas 1: 50
Ion Source Gas 2: 80
Interface Heater: ON The measurement conditions when (R)-BDMA, (R)-BACA, (R)-BNCA, (R)-PDMA, and (R)-PDEA were used as the axially chiral compound are shown in Table 4, Table 5, Table 6, Table 7, and Table 8 respectively.

TABLE 4

| Measurement condition of (R)-BDMA derivative | | | | | | | | |
|---|---|---|---|---|---|---|---|---|
| Amino acid | Q1 (Da) | Q3 (Da) | Time (ms) | DP (V) | EP (V) | CEP (V) | CE (V) | CXP (V) |
| Alanine | 428.085 | 339.2 | 50 | 51 | 7.5 | 30 | 27 | 4 |
| Aspartic acid | 472.049 | 339.3 | 50 | 41 | 6.5 | 14 | 31 | 16 |
| Phenylalanine | 504.222 | 339.2 | 50 | 51 | 9.5 | 20 | 31 | 4 |
| Proline | 454.056 | 339.1 | 50 | 51 | 8.0 | 16 | 27 | 4 |
| Serine | 444.000 | 339.2 | 50 | 51 | 7.5 | 30 | 27 | 4 |
| Threonine | 458.000 | 339.2 | 50 | 51 | 7.5 | 30 | 27 | 4 |
| Asparagine | 471.000 | 339.2 | 50 | 51 | 7.5 | 30 | 27 | 4 |
| Glutamine | 485.000 | 339.2 | 50 | 51 | 7.5 | 30 | 27 | 4 |
| Methionine | 488.000 | 339.2 | 50 | 51 | 7.5 | 30 | 27 | 4 |
| Valine | 456.000 | 339.2 | 50 | 51 | 7.5 | 30 | 27 | 4 |
| Leucine or isoleucine | 470.000 | 339.2 | 50 | 51 | 7.5 | 30 | 27 | 4 |
| Glutamic acid | 486.000 | 339.2 | 50 | 41 | 6.5 | 14 | 31 | 16 |
| Tryptophan | 543.000 | 339.2 | 50 | 51 | 9.5 | 20 | 31 | 4 |
| Tyrosine | 520.070 | 339.2 | 50 | 66 | 5.0 | 64 | 37 | 4 |
| Histidine | 247.643 | 110.0 | 50 | 26 | 7.5 | 14 | 27 | 4 |

TABLE 5

Measurement condition of (R)-BACA derivative

| Amino acid | Q1 (Da) | Q3 (Da) | Time (ms) | DP (V) | EP (V) | CEP (V) | CE (V) | CXP (V) |
|---|---|---|---|---|---|---|---|---|
| Alanine | 442.058 | 311.1 | 50 | 31 | 8.0 | 16 | 29 | 4 |
| Arginine | 527.114 | 201.1 | 50 | 56 | 8.0 | 22 | 29 | 4 |
| Proline | 468.108 | 311.1 | 50 | 41 | 8.5 | 20 | 35 | 4 |
| Serine | 458.000 | 311.1 | 50 | 31 | 8.0 | 16 | 29 | 4 |
| Glutamine | 499.000 | 311.1 | 50 | 31 | 8.0 | 16 | 29 | 4 |
| Methionine | 502.000 | 311.1 | 50 | 31 | 8.0 | 16 | 29 | 4 |
| Valine | 470.000 | 311.1 | 50 | 31 | 8.0 | 16 | 29 | 4 |
| Tryptophan | 557.000 | 310.9 | 50 | 41 | 9.0 | 22 | 35 | 4 |
| Tyrosine | 534.000 | 310.9 | 50 | 41 | 9.0 | 22 | 35 | 4 |
| Histidine | 508.000 | 156.0 | 50 | 56 | 8.0 | 22 | 29 | 4 |
| Lysine | 499.000 | 147.0 | 50 | 56 | 8.0 | 22 | 29 | 4 |

TABLE 6

Measurement condition of (R)-BNCA derivative

| Amino acid | Q1 (Da) | Q3 (Da) | Time (ms) | DP (V) | EP (V) | CEP (V) | CE (V) | CXP (V) |
|---|---|---|---|---|---|---|---|---|
| Alanine | 505.114 | 415.9 | 50 | 36 | 8.0 | 18 | 23 | 6 |
| Arginine | 295.682 | 106.0 | 50 | 36 | 6.0 | 14 | 23 | 4 |
| Threonine | 535.000 | 415.9 | 50 | 36 | 8.0 | 18 | 23 | 6 |
| Asparagine | 548.000 | 415.9 | 50 | 36 | 8.0 | 18 | 23 | 6 |
| Glutamine | 562.000 | 415.9 | 50 | 36 | 8.0 | 18 | 23 | 6 |
| Methionine | 565.000 | 415.9 | 50 | 36 | 8.0 | 18 | 23 | 6 |
| Valine | 533.000 | 415.9 | 50 | 36 | 8.0 | 18 | 23 | 6 |
| Glutamine | 563.000 | 106.2 | 50 | 41 | 9.5 | 22 | 51 | 4 |
| Tryptophan | 620.000 | 105.9 | 50 | 36 | 8.0 | 28 | 61 | 2 |
| Histidine | 286.170 | 106.0 | 50 | 21 | 7.0 | 16 | 27 | 4 |

TABLE 7

Measurement condition of (R)-PDMA derivative

| Amino acid | Q1 (Da) | Q3 (Da) | Time (ms) | DP (V) | EP (V) | CEP (V) | CE (V) | CXP (V) |
|---|---|---|---|---|---|---|---|---|
| Alanine | 356.000 | 267.1 | 50 | 36 | 4.5 | 38 | 25 | 4 |
| Serine | 372.000 | 267.1 | 50 | 36 | 4.5 | 38 | 25 | 4 |
| Threonine | 386.110 | 267.2 | 50 | 46 | 9.5 | 14 | 27 | 4 |
| Cysteine | 388.000 | 267.1 | 50 | 36 | 4.5 | 38 | 25 | 4 |
| Asparagine | 399.000 | 267.1 | 50 | 36 | 4.5 | 38 | 25 | 4 |
| Glutamine | 413.000 | 267.1 | 50 | 36 | 4.5 | 38 | 25 | 4 |
| Methionine | 416.000 | 267.1 | 50 | 36 | 4.5 | 38 | 25 | 4 |
| Valine | 384.000 | 267.1 | 50 | 36 | 4.5 | 38 | 25 | 4 |
| Leucine or isoleucine | 398.141 | 267.3 | 50 | 46 | 10 | 16 | 27 | 4 |
| Proline | 382.010 | 267.1 | 50 | 41 | 7.5 | 14 | 27 | 4 |
| Aspartic acid | 400.016 | 267.1 | 50 | 41 | 6 | 16 | 27 | 4 |
| Glutamic acid | 414.000 | 267.1 | 50 | 41 | 6.5 | 14 | 31 | 16 |
| Phenylalanine | 432.015 | 267.2 | 50 | 46 | 6.5 | 16 | 25 | 4 |
| Tryptophan | 471.000 | 267.2 | 50 | 51 | 9.5 | 20 | 31 | 4 |
| Tyrosine | 448.000 | 267.2 | 50 | 51 | 9.5 | 20 | 31 | 4 |
| Arginine | 221.099 | 267 | 50 | 21 | 5.5 | 14 | 13 | 4 |
| Histidine | 211.564 | 267.2 | 50 | 26 | 7.5 | 14 | 13 | 4 |
| Lysine | 340.282 | 267.2 | 50 | 31 | 10 | 14 | 23 | 4 |

TABLE 8

Measurement condition of (R)-PDEA derivative

| Amino acid | Q1 (Da) | Q3 (Da) | Time (ms) | DP (V) | EP (V) | CEP (V) | CE (V) | CXP (V) |
|---|---|---|---|---|---|---|---|---|
| Alanine | 384.350 | 295.3 | 50 | 56 | 6.5 | 18 | 25 | 4 |
| Serine | 400.000 | 295.3 | 50 | 56 | 6.5 | 18 | 25 | 4 |
| Threonine | 414.000 | 295.3 | 50 | 56 | 6.5 | 18 | 25 | 4 |
| Asparagine | 427.000 | 295.3 | 50 | 56 | 6.5 | 18 | 25 | 4 |
| Glutamine | 441.000 | 295.3 | 50 | 56 | 6.5 | 18 | 25 | 4 |
| Methionine | 444.000 | 295.3 | 50 | 56 | 6.5 | 18 | 25 | 4 |
| Valine | 412.000 | 295.3 | 50 | 56 | 6.5 | 18 | 25 | 4 |
| Leucine or isoleucine | 426.000 | 295.3 | 50 | 56 | 6.5 | 18 | 25 | 4 |
| Proline | 410.312 | 295.3 | 50 | 56 | 7.5 | 14 | 27 | 4 |
| Aspartic acid | 428.240 | 295.4 | 50 | 56 | 10 | 14 | 25 | 4 |
| Glutamic acid | 442.000 | 295.3 | 50 | 56 | 10 | 14 | 25 | 4 |
| Phenylalanine | 460.369 | 295.3 | 50 | 46 | 11 | 54 | 27 | 4 |
| Tryptophan | 499.000 | 295.3 | 50 | 46 | 11 | 54 | 27 | 4 |
| Tyrosine | 476.000 | 295.3 | 50 | 46 | 11 | 54 | 27 | 4 |
| Arginine | 235.217 | 295.3 | 50 | 26 | 8 | 12 | 15 | 4 |
| Histidine | 225.683 | 110.2 | 50 | 21 | 8.5 | 18 | 23 | 4 |
| Lysine | 368.200 | 295.3 | 50 | 56 | 6.5 | 18 | 25 | 4 |

Whether or not the derivative of a chiral amino acid was separated and detected was evaluated on the basis of resolution R. Resolution R was calculated according to the following mathematical formula. In the following mathematical formula, the retention time of the first derivative (D-amino acid derivative) obtained by a reaction between a D-form chiral amino acid and an axially chiral compound and the retention time of the second derivative (L-amino acid derivative) obtained by a reaction between an L-form chiral amino acid and an axially chiral compound are $t_{RD}$ and $t_{RL}$ (min), respectively, and the peak widths at half-height of a D-form derivative and an L-form derivative are $W_{RD}$ and $W_{RL}$ (min), respectively. When a D-form derivative is eluted earlier, the value of resolution R becomes positive.

$$R = \frac{1.18 \times (t_{RL} - t_{RD})}{(W_{RL} + W_{RD})}$$

The separation results when (R)-BDMA, (R)-BACA, (R)-BNCA, (R)-PDMA, and (R)-PDEA were used as the axially chiral compound are shown in Table 9, Table 10, Table 11, Table 12, and Table 13 respectively. It is noted that in the tables, "(allo)threonine" means a mixture of L-threonine and D-allothreonine, and "(allo)isoleucine" means a mixture of L-isoleucine and D-alloisoleucine.

TABLE 9

Separation with (R)-BDMA

| | Mixture of enantiomers | $t_{RD}$ | $W_{RD}$ | $t_{RL}$ | $W_{RL}$ | R |
|---|---|---|---|---|---|---|
| 1 | Alanine | 9.05 | 0.0923 | 9.98 | 0.1000 | 5.71 |
| 2 | Serine | 8.08 | 0.0922 | 8.50 | 0.0904 | 2.71 |
| 3 | (Allo)threonine | 8.35 | 0.0914 | 9.32 | 0.0823 | 6.59 |
| 4 | Aspartic acid | 8.47 | 0.0874 | 8.90 | 0.0876 | 2.90 |
| 5 | Asparagine | 7.74 | 0.0951 | 8.02 | 0.0940 | 1.75 |
| 6 | Glutamic acid | 8.63 | 0.0909 | 9.00 | 0.0870 | 2.45 |
| 7 | Glutamine | 6.90 | 0.1160 | 7.92 | 0.0984 | 5.61 |
| 8 | Methionine | 10.70 | 0.0855 | 11.80 | 0.0870 | 7.52 |
| 9 | Valine | 10.20 | 0.0935 | 11.60 | 0.0844 | 9.29 |
| 10 | Proline | 10.60 | 0.0868 | 10.80 | 0.0897 | 1.34 |
| 11 | Phenylalanine | 11.61 | 0.0908 | 12.82 | 0.0901 | 7.89 |
| 12 | Tryptophan | 11.70 | 0.0866 | 12.80 | 0.0914 | 7.29 |
| 13 | Tyrosine | 9.71 | 0.0899 | 10.80 | 0.0877 | 7.24 |
| 14 | Histidine | 4.33 | 0.2700 | 3.79 | 0.2490 | 1.23 |
| 15 | (Allo)isoleucine | 11.1 | 0.0867 | 12.5 | 0.0863 | 9.55 |
| 16 | Leucine | 11.5 | 0.0875 | 12.7 | 0.0890 | 8.02 |

TABLE 10

Separation with (R)-BACA

| No. | Mixture of enantiomers | $t_{RD}$ | $W_{RD}$ | $t_{RL}$ | $W_{RL}$ | R |
|---|---|---|---|---|---|---|
| 1 | Alanine | 11.90 | 0.0862 | 12.50 | 0.0920 | 3.97 |
| 2 | Serine | 11.20 | 0.1180 | 11.10 | 0.0893 | 0.57 |
| 3 | Glutamine | 9.48 | 0.0826 | 9.71 | 0.0839 | 1.63 |
| 4 | Methionine | 13.30 | 0.0890 | 13.90 | 0.0895 | 3.97 |
| 5 | Valine | 13.10 | 0.0882 | 13.80 | 0.0889 | 4.66 |
| 6 | Proline | 12.20 | 0.0903 | 12.50 | 0.0903 | 1.96 |
| 7 | Tryptophan | 14.30 | 0.0893 | 14.90 | 0.0878 | 4.00 |
| 8 | Tyrosine | 12.50 | 0.0899 | 12.80 | 0.0869 | 2.00 |
| 9 | Arginine | 9.73 | 0.0855 | 9.16 | 0.0861 | 3.92 |
| 10 | Histidine | 9.33 | 0.0897 | 8.53 | 0.0908 | 4.17 |
| 11 | Lysine | 10.80 | 0.0863 | 10.30 | 0.0882 | 3.38 |

TABLE 11

Separation with (R)-BNCA

| No. | Mixture of enantiomers | $t_{RD}$ | $W_{RD}$ | $t_{RL}$ | $W_{RL}$ | R |
|---|---|---|---|---|---|---|
| 1 | Alanine | 11.80 | 0.0863 | 12.20 | 0.0876 | 2.71 |
| 2 | (Allo)threonine | 11.20 | 0.0921 | 11.30 | 0.1050 | 0.60 |
| 3 | Asparagine | 13.90 | 0.1230 | 14.40 | 0.1310 | 2.32 |
| 4 | Glutamic acid | 9.53 | 0.0956 | 10.10 | 0.0870 | 2.57 |
| 5 | Glutamine | 10.50 | 0.0947 | 10.10 | 0.0890 | 3.68 |
| 6 | Methionine | 13.20 | 0.0899 | 13.60 | 0.0874 | 2.66 |
| 7 | Valine | 13.10 | 0.0903 | 13.60 | 0.0873 | 3.32 |
| 8 | Tryptophan | 14.10 | 0.0916 | 14.60 | 0.0875 | 3.29 |
| 9 | Arginine | 9.67 | 0.0884 | 9.10 | 0.0867 | 3.84 |
| 10 | Histidine | 9.14 | 0.0833 | 8.52 | 0.0921 | 4.17 |

TABLE 12

Separation with (R)-PDMA

| No. | Mixture of enantiomers | $t_{RD}$ | $W_{RD}$ | $t_{RL}$ | $W_{RL}$ | R |
|---|---|---|---|---|---|---|
| 1 | Alanine | 11.8 | 0.0802 | 12.2 | 0.1130 | 2.44 |
| 2 | Serine | 11.1 | 0.0794 | 11.6 | 0.0830 | 3.63 |
| 3 | (Allo)threonine | 11.2 | 0.0897 | 12.5 | 0.0760 | 9.26 |
| 4 | Aspartic acid | 11.5 | 0.0797 | 11.7 | 0.0867 | 1.42 |
| 5 | Asparagine | 10.9 | 0.0871 | 11.3 | 0.0814 | 2.80 |
| 6 | Glutamic acid | 11.6 | 0.0908 | 12.5 | 0.0957 | 5.69 |
| 7 | Glutamine | 11.0 | 0.0824 | 11.3 | 0.0857 | 2.11 |
| 8 | Methionine | 14.0 | 0.0908 | 15.9 | 0.0840 | 12.8 |
| 9 | Valine | 13.3 | 0.0902 | 15.7 | 0.0868 | 16.0 |
| 10 | Leucine | 14.5 | 0.0811 | 16.8 | 0.0799 | 16.9 |
| 11 | (Allo)isoleucine | 14.0 | 0.0824 | 16.5 | 0.0805 | 18.1 |
| 12 | Proline | 13.5 | 0.0891 | 14.0 | 0.0895 | 3.30 |
| 13 | Phenylalanine | 15.6 | 0.0876 | 17.8 | 0.0898 | 14.6 |
| 14 | Tryptophan | 15.8 | 0.0886 | 17.8 | 0.0904 | 13.2 |
| 15 | Tyrosine | 13.1 | 0.0890 | 14.8 | 0.0863 | 11.4 |
| 16 | Histidine | 9.21 | 0.0989 | 9.49 | 0.0935 | 1.72 |
| 17 | Lysine | 16.5 | 0.1030 | 17.3 | 0.0969 | 4.72 |
| 18 | Arginine | 9.75 | 0.1010 | 10.4 | 0.0857 | 4.11 |
| 19 | Cysteine | 12.5 | 0.0810 | 14.1 | 0.0962 | 9.32 |

TABLE 13

Separation with (R)-PDEA

| No. | Mixture of enantiomers | $t_{RD}$ | $W_{RD}$ | $t_{RL}$ | $W_{RL}$ | R |
|---|---|---|---|---|---|---|
| 1 | Alanine | 13.0 | 0.0803 | 14.2 | 0.0892 | 8.35 |
| 2 | Serine | 12.3 | 0.0668 | 12.6 | 0.0821 | 2.38 |
| 3 | (Allo)threonine | 12.5 | 0.0770 | 13.5 | 0.0744 | 7.79 |
| 4 | Aspartic acid | 12.7 | 0.0881 | 13.2 | 0.0872 | 3.37 |

TABLE 13-continued

Separation with (R)-PDEA

| No. | Mixture of enantiomers | $t_{RD}$ | $W_{RD}$ | $t_{RL}$ | $W_{RL}$ | R |
|---|---|---|---|---|---|---|
| 5 | Asparagine | 12.0 | 0.0712 | 12.3 | 0.0796 | 2.35 |
| 6 | Glutamic acid | 13.2 | 0.0758 | 13.4 | 0.0798 | 1.52 |
| 7 | Glutamine | 12.2 | 0.0883 | 12.4 | 0.0783 | 1.42 |
| 8 | Methionine | 14.8 | 0.0821 | 16.6 | 0.0840 | 12.8 |
| 9 | Valine | 14.1 | 0.0674 | 16.4 | 0.0841 | 17.9 |
| 10 | Leucine | 15.6 | 0.0829 | 17.9 | 0.0875 | 15.9 |
| 11 | (Allo)isoleucine | 15.1 | 0.0690 | 17.6 | 0.0852 | 19.1 |
| 12 | Proline | 14.5 | 0.0814 | 15.1 | 0.0796 | 4.40 |
| 13 | Phenylalanine | 16.3 | 0.0809 | 18.3 | 0.0863 | 14.1 |
| 14 | Tryptophan | 16.6 | 0.0792 | 18.3 | 0.0795 | 12.6 |
| 15 | Tyrosine | 14.0 | 0.0914 | 15.6 | 0.0764 | 11.3 |
| 16 | Histidine | 10.4 | 0.0645 | 10.6 | 0.0766 | 1.67 |
| 17 | Lysine | 17.3 | 0.0961 | 18.0 | 0.0953 | 4.32 |
| 18 | Arginine | 10.8 | 0.0902 | 11.2 | 0.0675 | 2.99 |

As a result, when (R)-BDMA, (R)-BACA, (R)-BNCA, (R)-PDMA, and (R)-PDEA were used, the D-amino acid derivative was eluted earlier than the L-amino acid derivative. That is, by using the axially chiral compound of R form, the D-amino acid could be eluted earlier, and subsequently the L-amino acid derivative could be eluted. This result demonstrates that a D-amino acid, which is often of low concentration in a biological sample such as blood plasma of higher organisms, can be eluted earlier. This is advantageous in terms of separation. Also, in some samples or tissues to be dealt with, an L-amino acid is of higher concentration in some cases. In such a case, the use of an S-form axially chiral compound enables the derivative of an L-amino acid to be eluted earlier. Furthermore, according to the method of the present invention, a mixed solution of proteinogenic amino acids having various properties such as acidic, basic, hydrophobic, and hydrophilic is possibly measured at once. Since the components are detected by mass spectrometry, interference by a contaminant component is not likely to be caused.

Moreover, it was confirmed that all amino acid derivatives can be separated and detected within 20 minutes.

Consequently, it was demonstrated that according to the method of the present invention, the existence and amount of each of chiral amino acids in a sample as well as the amount ratio between a pair of chiral amino acids can be analyzed with high sensitivity in a short time.

Example 2: Analysis Method of Chiral Carboxylic Acid

Into a reaction glass vial, approximately 0.1 mmol of a chiral carboxylic acid (Cbz-D-Phe-OH: N-benzyloxycarbonyl-D-phenylalanine, Cbz-L-Phe-OH: N-benzyloxycarbonyl-L-phenylalanine, L-lactic acid, or DL-lactic acid) was charged, and dissolved in 0.5 mL of tetrahydrofuran. 10 μL of $SOCl_2$ (0.138 mmol) was dropped. The mixture was stirred at room temperature for 3 hours. Triethylamine (11 μL, 0.123 mmol) was added, and the mixture was further stirred at room temperature for 20 minutes. As the axially chiral compound, the (R)—N-(1-(2-aminonaphthalen-1-yl)naphthalen-2-yl)acetamide (20 mg, 0.061 mmol) obtained in Step A of Synthesis Example 1 was added. The mixture was stirred at room temperature overnight.

The vial was flushed with air thereby to lightly volatilize the volatile solvent or reaction product. Then, the reaction mixture diluted with 500 μL of acetonitrile was diluted with water/acetonitrile=1/1 by a factor of 100. The obtained dilution was further diluted with water by a factor of 100 to obtain a sample of the derivative. The outline of the derivatization reaction is as follows:

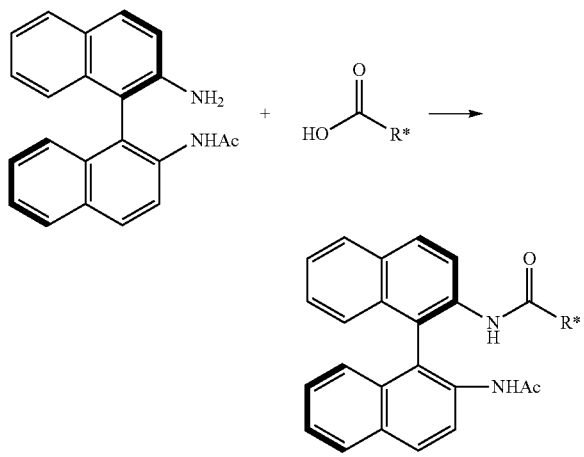

(wherein R* represents N-benzyloxycarbonyl-D-phenylalanyl, N-benzyloxycarbonyl-L-phenylalanyl, N-benzyloxycarbonyl-DL-phenylalanyl, or 1-hydroxyethyl).

Separation and detection were performed by LC-MS/MS (SRM). The separation condition is similar to that in Example 1. The setting parameters of the mass spectrometer and the like are similar to those in Example 1. The measurement condition of mass spectrometry is shown in Table 14.

TABLE 14

Measurement condition of chiral carboxylic acid derivative

| Organic acid | Q1(Da) | Q3(Da) | Time (ms) | DP (V) | EP (V) | CEP (V) | CE (V) | CXP (V) |
|---|---|---|---|---|---|---|---|---|
| Cbz-Phe-OH | 608.019 | 375.2 | 150 | 56 | 7.0 | 20 | 35 | 6 |
| Lactic acid | 399.035 | 285.1 | 150 | 51 | 7.5 | 16 | 31 | 4 |

According to the aforementioned condition, the derivative of an L-lactic acid, the derivative of a DL-lactic acid, the derivative of Cbz-D-Phe-OH, the derivative of Cbz-L-Phe-OH, and the derivative of Cbz-D,L-Phe-OH (mixture of samples of a D-form derivative and an L-form derivative) were each measured by LC-MS/MS (SRM), and the separation of a D-form derivative and an L-form derivative in each of the organic acids was checked. The separation result is shown in Table 15.

TABLE 15

Separation of chiral carboxylic acid derivative

| No. | Mixture of enantiomers | $t_{RD}$ | $W_{RD}$ | $t_{RL}$ | $W_{RL}$ | R |
|---|---|---|---|---|---|---|
| 1 | Lactic acid | 11.9 | 0.0946 | 12.2 | 0.0907 | 1.91 |
| 2 | Cbz-Phe-OH | 10.1 | 0.0649 | 10.3 | 0.0680 | 1.78 |

As a result, it was confirmed that a D-form derivative and an L-form derivative can be separated and detected in each of lactic acid and Cbz-D,L-Phe-OH. It was also confirmed that all of the derivatives can be analyzed within 20 minutes.

Example 3: Analysis Method of Chiral Amino Acid in Biological Sample and Food Product In this example, a chiral amino acid in a biological sample and a food product was analyzed.

3-1) Preparation of Axially Chiral Compound Solution

Into a 5 mL vial, approximately 10 mg of an axially chiral compound (R)—PNP-PDEA was weighted and charged, and acetonitrile was added so that the concentration of the axially chiral compound became approximately 10 mmol/L. The mixture was thoroughly stirred to obtain an axially chiral compound solution.

3-2) Production of Authentic Preparation

There was prepared a hydrochloric acid solution of a chiral amino acid mixture in which glycine, L-histidine, L-arginine, L-lysine, L-alanine, L-serine, L-proline, L-valine, L-threonine, L-leucine, L-isoleucine, L-asparagine, L-aspartic acid, L-glutamine, L-glutamic acid, L-methionine, L-phenylalanine, L-tyrosine, L-tryptophan, and L-cystine each with a concentration of 0.5 µmol/L, as well as D-histidine, D-arginine, D-lysine, D-alanine, D-serine, D-proline, D-valine, D-allothreonine, D-leucine, D-alloisoleucine, D-asparagine, D-aspartic acid, D-glutamine, D-glutamic acid, D-methionine, D-phenylalanine, D-tyrosine, and D-tryptophan each with a concentration of 0.05 µmol/L are contained in a hydrochloric acid with a concentration of 0.01 mol/L. In addition, there was prepared a hydrochloric acid solution of a mixture in which D-cysteine and L-cysteine each with a concentration of 1 µmol/L were contained in a hydrochloric acid with a concentration of 0.01 mol/L. This was used for confirming the peak positions of cystine and cysteine.

3-3) Pretreatment Method of Biological Sample

As a biological sample, blood plasma or cerebrospinal fluid of a rat (male, Iar:Wistar) was used. Each biological sample was pretreated as follows.

Blood plasma: diluted with acetonitrile by a factor of 2, centrifuged at 4° C. and 20000 G for 10 minutes, and supernatants diluted with pure water by a factor of 10

Cerebrospinal fluid: diluted with acetonitrile by a factor of 2, centrifuged at 4° C. and 20000 G for 10 minutes, and supernatants diluted with pure water by a factor of 10

3-4) Pretreatment Method of Food Product

As a food product, black vinegar (Sakamoto Kurozu Satsuma manufactured by Sakamoto Kurozu, Inc.) was used. Black vinegar was pretreated as follows.

Black vinegar: diluted with pure water by a factor of 100

3-5) Derivatization of Mixture of Chiral Amino Acid (D Form and L Form)

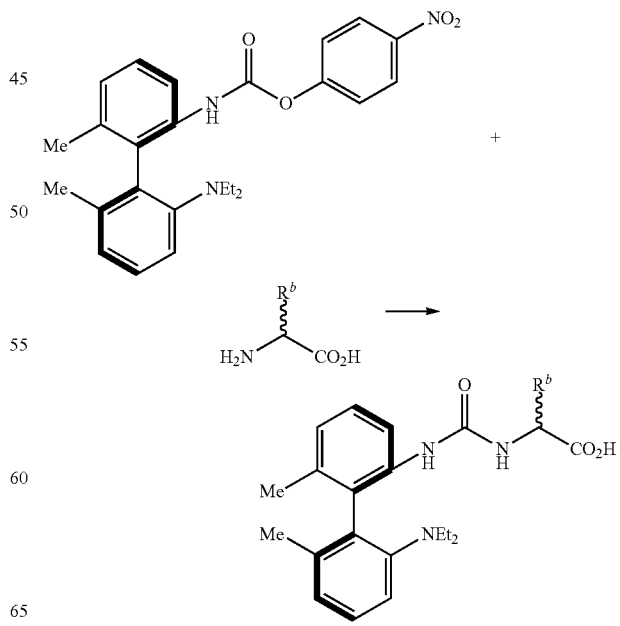

To 30 µL of a 200 mmol/L boric acid buffer and 30 µL of acetonitrile, 104 of a solution of the authentic preparation, the food product, or the biological sample containing a chiral amino acid (D form and L form) was added, and stirred using a vortex mixer. Into the mixture, 10 µL of the axially chiral compound solution was added, and stirred using a vortex mixer. Thereafter, the resultant product was left to stand at room temperature or at 55° C. for 10 minutes. After the termination of the reaction, 120 µL of a 0.1% formic acid aqueous solution was added. Accordingly, a derivative mixture containing the first derivative of a chiral amino acid (D form) and the second derivative of a chiral amino acid (L form) was obtained.

3-6) Separation and Detection of First Derivative and Second Derivative

The first derivative and the second derivative contained in the sample solution were separated by reverse phase high performance liquid column chromatography. The condition is as follows.
Column: Acquity UPLC (registered trademark) BEH-Phenyl manufactured by Waters, 1.7 µm (2.1×50 mm, 186002884) (this column is a hydrophobic column used for hydrophobic chromatography)
Temperature: 40° C.
Mobile Phase A: 0.1% formic acid aqueous solution
Mobile Phase B: acetonitrile/water/formic acid (90/10/0.1) solution
The flow condition of the mobile phases is shown in Table 16.

TABLE 16

Flow condition 3

| min | Flow Rate (µL/min) | % A | % B |
|---|---|---|---|
| 0 | 400 | 89 | 11 |
| 1.5 | 400 | 88 | 12 |
| 3.0 | 400 | 79 | 21 |
| 7.5 | 400 | 70 | 30 |
| 9.5 | 400 | 55 | 45 |
| 10.5 | 400 | 10 | 90 |
| 11.9 | 400 | 10 | 90 |
| 12.0 | 400 | 89 | 11 |
| 14.0 | 400 | 89 | 11 |

Detection was performed by mass spectrometry using a mass spectrometer (Triple Quad 6500 manufactured by Sciex). The setting parameters of the mass spectrometer and the like are as follows.

Setting of Autosampler
Injection Volume: 1 µL
Autosampler Temperature: 4° C.
Parameter Setting of Ion Source
Ionization Method: ESI (positive ion mode)
Curtain Gas: 40
Collision Gas Setting: 8
Ion Spray Voltage: 4500
Temperature: 600
Ion Source Gas 1: 70
Ion Source Gas 2: 70
Entrance Potential: 10
The measurement condition is shown in Table 17.

TABLE 17

Measurement condition of (R)-PNP-PDEA derivative

| Amino acid | Q1 (Da) | Q3 (Da) | Time (ms) | DP (V) | EP (V) | CE (V) | CXP (V) |
|---|---|---|---|---|---|---|---|
| Histidine | 225.6 | 295.2 | 20 | 46 | 10 | 15 | 4 |
| Arginine | 235.2 | 295.1 | 20 | 46 | 10 | 17 | 10 |

TABLE 17-continued

Measurement condition of (R)-PNP-PDEA derivative

| Amino acid | Q1 (Da) | Q3 (Da) | Time (ms) | DP (V) | EP (V) | CE (V) | CXP (V) |
|---|---|---|---|---|---|---|---|
| Cysteine | 355.7 | 295.1 | 20 | 51 | 10 | 25 | 10 |
| Lysine | 368.4 | 295.1 | 20 | 46 | 10 | 29 | 36 |
| Glycine | 370.0 | 295.0 | 20 | 136 | 10 | 29 | 10 |
| Alanine | 384.1 | 295.3 | 20 | 136 | 10 | 29 | 10 |
| Serine | 400.0 | 295.3 | 20 | 136 | 10 | 29 | 10 |
| Proline | 410.2 | 295.2 | 20 | 46 | 10 | 31 | 8 |
| Valine | 412.0 | 295.3 | 20 | 136 | 10 | 29 | 10 |
| (Allo)threonine | 414.0 | 295.3 | 20 | 136 | 10 | 29 | 10 |
| Cystine | 415.3 | 295.1 | 20 | 46 | 10 | 23 | 12 |
| Leucine or (Allo)isoleucine | 426.0 | 295.3 | 20 | 136 | 10 | 29 | 10 |
| Asparagine | 427.0 | 295.3 | 20 | 136 | 10 | 29 | 10 |
| Aspartic acid | 428.2 | 295.1 | 20 | 66 | 10 | 35 | 10 |
| Glutamine | 441.0 | 295.3 | 20 | 136 | 10 | 29 | 10 |
| Glutamic acid | 442.0 | 295.1 | 20 | 66 | 10 | 35 | 10 |
| Methionine | 444.0 | 295.3 | 20 | 136 | 10 | 29 | 10 |
| Phenylalanine | 460.1 | 295.0 | 20 | 26 | 10 | 33 | 8 |
| Tyrosine | 476.0 | 295.0 | 20 | 26 | 10 | 33 | 8 |
| Tryptophan | 499.0 | 295.0 | 20 | 26 | 10 | 33 | 8 |

The separation result of the authentic sample is shown in Table 18. R in the table indicates resolution. The definitions of R, $t_{RD}$, $t_{RL}$, $W_{RD}$, and $W_{RL}$ are the same as the definitions described in Example 1.

TABLE 18

Separation with (R)-PNP-PDEA

| No. | Mixture of enantiomers | $t_{RD}$ | $W_{RD}$ | $t_{RL}$ | $W_{RL}$ | R |
|---|---|---|---|---|---|---|
| 1 | Alanine | 3.84 | 0.0369 | 4.50 | 0.0400 | 10.1 |
| 2 | Serine | 3.53 | 0.0355 | 3.70 | 0.0355 | 2.83 |
| 3 | (Allo)threonine | 3.63 | 0.0343 | 4.14 | 0.0338 | 8.84 |
| 4 | Aspartic acid | 3.73 | 0.0308 | 3.97 | 0.0371 | 4.17 |
| 5 | Asparagine | 3.42 | 0.0376 | 3.57 | 0.0330 | 2.51 |
| 6 | Glutamic acid | 3.78 | 0.0361 | 4.09 | 0.0340 | 5.22 |
| 7 | Glutamine | 3.50 | 0.0331 | 3.61 | 0.0323 | 1.98 |
| 8 | Methionine | 4.86 | 0.0371 | 6.44 | 0.0465 | 22.3 |
| 9 | Valine | 4.43 | 0.0342 | 6.20 | 0.0519 | 24.3 |
| 10 | Leucine | 5.05 | 0.0408 | 7.45 | 0.0550 | 29.6 |
| 11 | (Allo)isoleucine | 5.42 | 0.0494 | 7.70 | 0.0566 | 25.4 |
| 12 | Proline | 4.71 | 0.0443 | 5.11 | 0.0458 | 5.24 |
| 13 | Phenylalanine | 6.12 | 0.0533 | 8.23 | 0.0548 | 23.0 |
| 14 | Tryptophan | 6.31 | 0.0486 | 8.35 | 0.0495 | 24.5 |
| 15 | Tyrosine | 4.38 | 0.0350 | 5.60 | 0.0461 | 17.8 |
| 16 | Histidine | 2.01 | 0.0391 | 2.22 | 0.0507 | 2.76 |
| 17 | Lysine | 7.08 | 0.0590 | 8.02 | 0.0538 | 9.83 |
| 18 | Arginine | 2.29 | 0.0602 | 2.78 | 0.0501 | 5.24 |
| 19 | Cystine | 7.41 | 0.0545 | 8.76 | 0.0378 | 17.3 |
| 20 | Cysteine | 9.00 | 0.0419 | 9.40 | 0.0367 | 6.01 |

* The peak positions of cystine and cysteine were checked with a solution containing D-cysteine and L-cysteine each with a concentration of 1 µmol/L as an authentic preparation.

As a result, in the separation of each of blood plasma, cerebrospinal fluid, and black vinegar, the peak appeared at a position similar to that for the authentic preparation, and the derivatives of the respective amino acids could be sufficiently separated in a similar manner to that for the authentic preparation.

The area value of each peak is shown in Table 19.

TABLE 19

| | | Peak area value(cps) | | | | | | |
|---|---|---|---|---|---|---|---|---|
| | | Authentic preparation | | Black vinegar | | Blood plasma | | Cerebrospinal fluid | |
| No | Enantiomer | D Form | L Form | D Form | L Form | D Form | L Form | D Form | L Form |
| 1 | Alanine | 7.35E+04 | 5.17E+05 | 4.13E+06 | 9.08E+06 | 5.55E+05 | 1.29E+07 | 5.35E+04 | 9.39E+06 |
| 2 | Serine | 2.71E+04 | 2.61E+05 | 2.97E+05 | 3.21E+06 | 3.76E+04 | 4.16E+06 | 1.86E+05 | 5.34E+06 |
| 3 | (Allo)threonine | 2.36E+04 | 2.53E+05 | 3.35E+04 | 1.23E+06 | Tr. | 3.95E+06 | 6.40E+03 | 6.14E+06 |
| 4 | Aspartic acid | 4.57E+04 | 4.59E+05 | 3.66E+05 | 2.02E+06 | 2.84E+04 | 3.14E+06 | ND. | 7.99E+04 |
| 5 | Asparagine | 1.63E+04 | 1.63E+05 | Tr. | 6.34E+04 | 9.60E+04 | 7.65E+05 | 6.70E+03 | 3.70E+05 |
| 6 | Glutamic acid | 2.64E+04 | 2.89E+05 | 1.03E+05 | 8.92E+05 | 7.93E+03 | 2.05E+06 | ND. | 1.32E+05 |
| 7 | Glutamine | 2.24E+04 | 2.48E+05 | N.D. | ND. | 2.25E+04 | 9.69E+06 | 1.13E+05 | 3.86E+07 |
| 8 | Methionine | 3.58E+04 | 3.49E+05 | 5.18E+03 | 2.60E+05 | 4.87E+04 | 1.82E+06 | 1.80E+04 | 6.01E+05 |
| 9 | Valine | 1.75E+04 | 2.36E+05 | 7.58E+03 | 2.12E+06 | 7.20E+03 | 2.48E+06 | Tr. | 3.65E+05 |
| 10 | Leucine | 2.55E+04 | 1.89E+05 | 7.30E+03 | 1.06E+06 | 9.93E+03 | 1.03E+06 | Tr. | 1.62E+05 |
| 11 | (Allo)isoleucine | 2.83E+04 | 1.86E+05 | 4.21E+04 | 1.60E+06 | 2.19E+04 | 1.67E+06 | 7.08E+03 | 4.18E+05 |
| 12 | Proline | 8.15E+04 | 7.96E+05 | 2.12E+05 | 3.78E+06 | 2.75E+04 | 1.01E+07 | N.D. | 1.77E+05 |
| 13 | Phenylalanine | 1.03E+05 | 8.78E+05 | 4.94E+04 | 1.28E+06 | 1.60E+04 | 4.54E+06 | 5.51E+03 | 1.76E+06 |
| 14 | Tryptophan | 7.04E+04 | 6.42E+05 | N.D. | 2.21E+05 | 1.41E+04 | 6.61E+06 | N.D. | 6.50E+05 |
| 15 | Tyrosine | 2.49E+04 | 6.00E+05 | Tr. | 1.01E+06 | 7.29E+03 | 5.24E+06 | Tr. | 1.60E+06 |
| 16 | Histidine | 3.14E+04 | 3.22E+05 | 6.63E+03 | 6.94E+05 | Tr. | 1.57E+06 | Tr. | 1.66E+06 |
| 17 | Lysine | 1.83E+05 | 1.96E+06 | 1.14E+05 | 8.38E+06 | 1.38E+05 | 5.22E+07 | 9.50E+04 | 4.22E+07 |
| 18 | Arginine | 5.05E+04 | 6.45E+05 | 6.43E+03 | 1.20E+05 | 2.87E+04 | 9.90E+06 | 2.01E+04 | 7.65E+06 |
| 19 | Cystine | N.D. | 1.11E+06 | N.D. | 3.79E+04 | N.D. | 1.44E+05 | N.D. | 8.54E+05 |

\* The authentic preparation does not include D-cystine, and includes only L-cystine.
\* Less than 5.00E+03 is indicated as Tr., and absence of a peak as N.D.

The aforementioned result demonstrates that according to the method of the present invention, a mixed sample of amino acids having various properties such as acidic, basic, hydrophobic, and hydrophilic can be concurrently analyzed in one measurement. It is also demonstrated that even a sample containing a contaminant component such as a biological sample and a food product can be analyzed. Furthermore, it is demonstrated that the amino acid content ratio in an amino acid mixed sample can be determined.

Example 4: Analysis Method of Chiral Thiol 4-1) Derivatization of Mixture of Chiral Thiol (D Form and L Form)

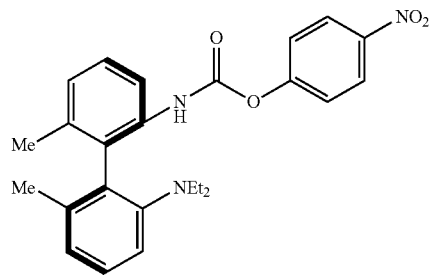

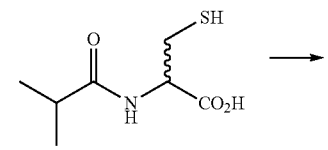

-continued

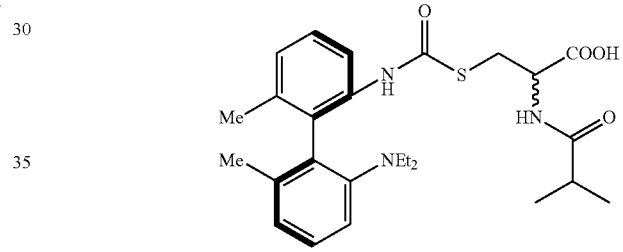

With a 0.01 mmol/L hydrochloric acid as a solvent, a chiral thiol mixed solution containing a chiral thiol (iBu-D-Cys-OH: N-isobutyryl-D-cysteine and iBu-L-Cys-OH: N-isobutyryl-L-cysteine) each in an amount of 1 mmol/L was prepared. Derivatization of the chiral thiols was performed in a similar manner to that in Example 1, except that (R)-PNP-PDEA was used as the axially chiral compound, and the chiral thiol mixed solution was used in place of the chiral amino acid mixed solution. Thus, a derivative mixture containing the first derivative of a chiral thiol (D form) and the second derivative of a chiral thiol (L form) was obtained.

4-2) Separation and Detection of First Derivative and Second Derivative

Separation and detection were performed by LC-MS/MS (SRM).

First, the first derivative and the second derivative contained in the sample solution were separated by reverse phase high performance liquid column chromatography. The condition is as follows.

Column: Two Inertsils (registered trademark) ODS-3 manufactured by GL Sciences, 2 μm (2.1×100 mm, 5020-), were connected in series to be used as a column. (This column is a hydrophobic column used for hydrophobic chromatography.)
Temperature: 40° C.
Mobile Phase A: 0.1% formic acid aqueous solution
Mobile Phase B: acetonitrile/water (95/5) solution
Analysis was performed under the isocratic condition of A/B=75/25.

Detection was performed using a mass spectrometer (Triple Quad 6500 manufactured by Sciex). The setting parameters of the mass spectrometer and the like are similar to those in Example 3. The measurement condition of mass spectrometry is shown in Table 20.

TABLE 20

| Measurement condition of (R)-PNP-PDEA derivative | | | | | | | | |
|---|---|---|---|---|---|---|---|---|
| Chiral thiol | Q1(Da) | Q3 (Da) | Time (ms) | DP (V) | EP (V) | CEP (V) | CE (V) | CXP (V) |
| iBu-Cys-OH | 486.17 | 295.3 | 150 | 46 | 10 | 16 | 27 | 4 |

According to the aforementioned condition, the separation of the derivative of iBu-D-Cys-OH and the derivative of iBu-L-Cys-OH was confirmed by LC-MS/MS (SRM). The separation result is shown in Table 21. R in the table indicates resolution. The definitions of R, $t_{RD}$, $t_{RL}$, $W_{RD}$, and $W_{RL}$ are the same as the definitions described in Example 1.

TABLE 21

| Separation with (R)-PNP-PDEA | | | | | |
|---|---|---|---|---|---|
| Mixture of enantiomers | $t_{RD}$ | $W_{RD}$ | $t_{RL}$ | $W_{RL}$ | R |
| iBu-Cys-OH | 80.2 | 1.14 | 77.6 | 1.17 | −1.32 |

The results demonstrated that a mixture of a chiral thiol can be reacted with the axially chiral compound of the present invention to obtain a derivative mixture, and the derivative of iBu-L-Cys-OH and the derivative of iBu-D-Cys-OH can be separated and detected.

Example 5: Analysis Method of Chiral Alcohol 5-1) Derivatization of Chiral Alcohol (D Form and L Form)

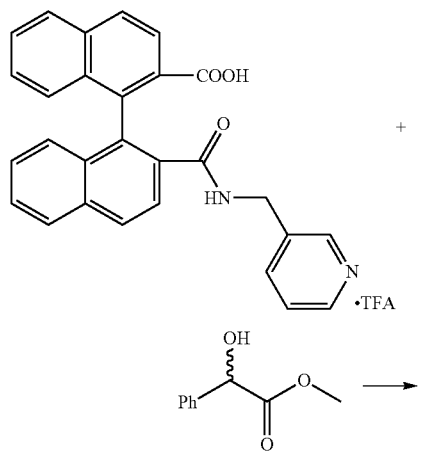

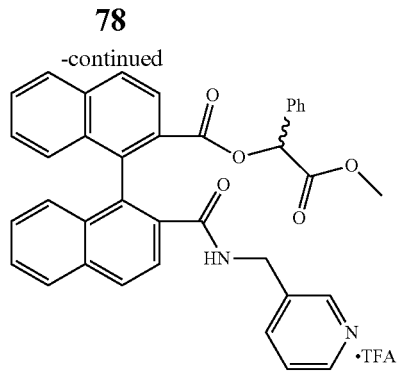

-continued (Although the absolute configuration of chiral PBNA-TFA is not illustrated in the aforementioned formula, the chiral PBNA-TFA is a stereoisomer having the absolute configuration of R or S obtained in Synthesis Example 7.)

To 1 mg of methyl D-mandelate, 1 mg of the chiral PBNA-TFA obtained in Synthesis Example 7 was added. Furthermore, 1 mL of dichloromethane and 10 μL of thionyl chloride were added as a solvent. The mixture was stirred at room temperature for 10 minutes. The solvent was distilled away, and 0.5 mL of water and 1 mL of acetonitrile were added. With a 0.1% formic acid, the solution was diluted by a factor of 1000. Accordingly, a solution (D-form solution) containing the first derivative of a chiral alcohol (D form) was obtained.

Also, a solution (L-form solution) containing the second derivative of a chiral alcohol (L form) was obtained in a similar manner to the aforementioned operation with methyl L-mandelate in place of methyl D-mandelate.

In this method, an acid chloride of chiral PBNA-TFA is generated in the system, and reacted with methyl mandelate that is an enantiomer.

For studying the separation condition, there was used a solution in which the D-form solution and the L-form solution were mixed at a ratio of 1:1.

5-2) Separation and Detection of First Derivative and Second Derivative

Separation and detection were performed by LC-MS/MS (SRM).

First, the first derivative and the second derivative contained in the sample solution were separated by reverse phase high performance liquid column chromatography. The condition is as follows.

Column: Two Inertsils (registered trademark) ODS-3 manufactured by GL Sciences, 2 μm (2.1×100 mm, 5020-), were connected in series to be used as a column. (This column is a hydrophobic column used for hydrophobic chromatography.)

Temperature: 40° C.

Mobile Phase A: 0.1% formic acid aqueous solution

Mobile Phase B: acetonitrile/water (95/5) solution

Analysis was performed under the isocratic condition of A/B=75/25.

Detection was performed using a mass spectrometer (Triple Quad 6500 manufactured by Sciex). The setting parameters of the mass spectrometer and the like are similar to those for (R)—PNP-PDEA of Example 3. The measurement condition of mass spectrometry is shown in Table 22.

TABLE 22

| | | | | | | | | |
|---|---|---|---|---|---|---|---|---|
| Amino acid | Q1(Da) | Q3 (Da) | Time (ms) | DP (V) | EP (V) | CEP (V) | CE (V) | CXP (V) |
| Methyl mandelate | 581.297 | 281.2 | 150 | 60 | 10.5 | 22 | 31 | 4 |

According to the aforementioned condition, the separation of the derivative of methyl D-mandelate and the derivative of methyl L-mandelate was confirmed by LC-MS/MS (SRM). The separation result is shown in Table 23.

TABLE 23

Separation with chiral PBNA-TFA

| Mixture of enantiomers | $t_1$ | $W_1$ | $t_2$ | $W_2$ | R |
|---|---|---|---|---|---|
| Methyl mandelate | 13.6 | 0.322 | 14.4 | 0.335 | 1.44 |

In the table, resolution R was calculated according to the following mathematical formula. In the following mathematical formula, the retention time of the first derivative (the derivative of methyl D-mandelate) obtained by a reaction between a D-form chiral alcohol (methyl D-mandelate) and chiral PBNA-TFA and the retention time of the second derivative (the derivative of methyl L-mandelate) obtained by a reaction between an L-form chiral alcohol (methyl L-mandelate) and chiral PBNA-TFA are $t_1$ and $t_2$ (min), respectively, and the peak widths at half-height of the first derivative and the second derivative are $W_1$ and $W_2$ (min), respectively.

$$R = \frac{1.18 \times |t_1 - t_2|}{W_1 + W_2}$$

The results demonstrated that methyl D-mandelate and methyl L-mandelate, which are chiral alcohols, can be reacted with the axially chiral compound of the present invention to obtain derivatives, and the derivative of methyl D-mandelate and the derivative of methyl L-mandelate can be separated and detected.

Therefore, it is understood that a mixture of methyl D-mandelate and methyl L-mandelate can be reacted with the axially chiral compound of the present invention, so that it can be separated and detected as a mixture of the derivative of methyl D-mandelate and the derivative of methyl L-mandelate.

As discussed above, it has been demonstrated that the method of the present invention is effective for the analysis of not only a chiral amino acid but also a chiral carboxylic acid, a chiral thiol, and a chiral alcohol. Therefore, it was demonstrated that the method of the present invention can be used as a general analysis method of any enantiomer independent of the kinds of enantiomers.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I') or a salt thereof, or a mixture thereof:

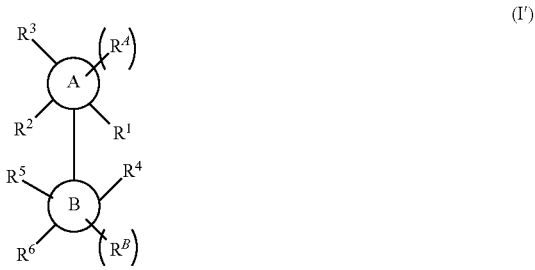

(I')

wherein
ring A and ring B each independently represent a benzene ring or a heteroaromatic ring,
a bond between the ring A and the ring B represents an axis of chirality,
$R^1$ represents a group bonded to one ring-constituting atom adjacent to a ring A-constituting atom bonded to the ring B,
$R^2$ represents a group bonded to the other ring-constituting atom adjacent to the ring A-constituting atom bonded to ring B,
$R^3$ represents a hydrogen atom or a group,
or $R^2$ and $R^3$ optionally form a ring together,
$R^4$ represents a group bonded to one ring-constituting atom adjacent to a ring B-constituting atom bonded to the ring A,
$R^5$ represents a group bonded to the other ring-constituting atom adjacent to the ring B-constituting atom bonded to the ring A,
$R^6$ represents a hydrogen atom or a group,
or $R^5$ and $R^6$ optionally form a ring together,
rings A and B optionally further have one or two $R^A$s and one or two $R^B$S that are bonded to an atom constituting each ring, wherein the one or two $R^A$s and the one or two $R^B$s each represent a group,
the groups of $R^1$, $R^2$, $R^3$, $R^4$, $R^5$, $R^6$, $R^A$, and $R^B$ are (a') a group represented by the general formula (i), or a group containing the group represented by the general formula (i), (b) a group having a charged atom or a chargeable atom, or (c) a substituent,
(a') the group represented by the general formula (i), or the group containing the group represented by general formula (i) exists only in any one of $R^1$ to $R^6$, $R^A$, and $R^B$,
at least one of $R^1$ to $R^6$, $R^A$, and $R^B$ is the group having a charged atom or a chargeable atom,
the group having a charged atom or a chargeable atom is a di($C_1$ to $C_6$ alkyl)amino group, a tri($C_1$ to $C_6$alkyl) ammonio group, a piperidino group, a morpholino group, or a group represented by the general formula (d1) or the general formula (d2), formula (i) is as below:

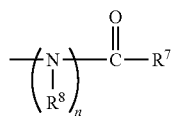
(i)

wherein
$R^7$ represents a hydroxy group or a leaving group, wherein the leaving group is selected from the group consisting of $C_1$ to $C_6$ alkylcarbonyloxy, a halogen atom, succinimidooxy, phenyloxy having an electron-withdrawing group, imidazolyl, and triazolyl,
n represents 0 or 1,
$R^8$ does not exist when n is 0, and
$R^8$ represents a hydrogen atom or a $C_1$ to $C_6$ alkyl group when n is 1,
formula (d1) is as below:

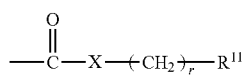
(d1)

wherein
X represents a nitrogen atom or an oxygen atom,
r represents an integer of 0 to 10,
$R^{11}$ represents a substituent having a positively charged nitrogen atom or a substituent having an uncharged nitrogen atom, and
formula (d2) is as below:

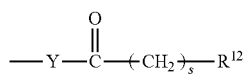
(d2)

wherein
Y represents a nitrogen atom or an oxygen atom,
s represents an integer of 0 to 10,
$R^{12}$ represents a substituent having a positively charged nitrogen atom or a substituent having an uncharged nitrogen atom,
wherein said (c) a substituent is not an amino group.

2. The compound, salt thereof, or mixture thereof according to claim 1, represented by formula (II'):

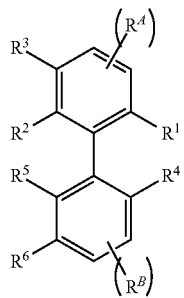
(II')

wherein
a bond between benzene rings represents an axis of chirality,
$R^1$ and $R^4$ each represent a group,
$R^2$ represents a group,
$R^3$ represents a hydrogen atom or a group, or $R^2$ and $R^3$ optionally form a ring together,
$R^5$ represents a group,
$R^6$ represents a hydrogen atom or a group, or $R^5$ and $R^6$ optionally form a ring together,
the two benzene rings optionally further have one or two $R^A$s and one or two $R^B$S that are bonded to an atom constituting each ring, wherein the one or two $R^A$s and the one or two $R^B$s each represent a group,
the groups of $R^1$, $R^2$, $R^3$, $R^4$, $R^5$, $R^6$, $R^A$, and $R^B$ are (a') a group represented by the general formula (i) as defined in claim 1, or a group containing the group represented by the general formula (i), (b) a group having a charged atom or a chargeable atom, or (c) a substituent,
(a') the group represented by the general formula (i), or the group containing the group represented by the general formula (i) exists only in any one of $R^1$ to $R^6$, $R^A$, and $R^B$, and
at least one of $R^1$ to $R^6$, $R^A$, and $R^B$ is the group having a charged atom or a chargeable atom,
wherein said (c) a substituent is not an amino group.

3. The compound, salt thereof, or mixture thereof according to claim 1, represented by formula (II-1):

(II-1)

wherein
a bond between two benzene rings represents an axis of chirality,
$R^1$ represents a group represented by the general formula (i) as defined in claim 1, or a group containing the group represented by the general formula (i),
$R^4$ represents a group having a charged atom or a chargeable atom,
$R^2$ and $R^5$ each represent (c) a substituent, and
the two benzene rings optionally further have one or two $R^A$s and one or two $R^B$S that are bonded to an atom constituting each ring, wherein the one or two $R^A$s and the one or two $R^B$s each represent (c) a substituent
wherein said (c) a substituent is not an amino group.

4. A method for analyzing an enantiomer, comprising (1) to (3) below:
(1) reacting a mixture of a first compound and a second compound that are a pair of enantiomers with an axially chiral compound that is one of a pair of axially chiral isomers, to generate a derivative mixture containing a first derivative obtained by a reaction of the first compound with the axially chiral compound and a second derivative obtained by a reaction of the second compound with the axially chiral compound;

(2) separating said first derivative and said second derivative in the derivative mixture; and (3) detecting the separated first derivative and second derivative by mass spectrometry, wherein said axially chiral isomer is a compound according to claim 1.

5. The method according to claim 4, wherein said axially chiral compound is an R form.

6. The method according to claim 4, wherein said separating is performed by chromatography, electrophoresis, or ion mobility spectrometry.

7. The method according to claim 4, wherein said separating is performed by liquid chromatography using a hydrophobic column.

8. The method according to claim 4, wherein in separation, retention times of the first derivative and the second derivative are within 120 minutes.

9. The method according to claim 4, wherein said first compound and said second compound are a pair of enantiomers of a chiral compound selected from the group consisting of a chiral amino acid, a chiral amine, a chiral alcohol, a chiral carboxylic acid, and a chiral thiol.

10. The method according to claim 9, wherein said chiral amino acid is one or more amino acids selected from the group consisting of alanine, valine, leucine, isoleucine, serine, threonine, cysteine, lysine, arginine, aspartic acid, glutamic acid, asparagine, glutamine, methionine, phenylalanine, tyrosine, tryptophan, histidine, and proline.

11. The method according to claim 10, wherein said separating is performed so that resolution R represented by the mathematical formula below indicates a value of 0.5 or more:

$$R = \frac{1.18 \times |t_1 - t_2|}{W_1 + W_2}$$

wherein $t_1$ represents a retention time (min) of the first derivative, $t_2$ represents a retention time (min) of the second derivative, $W_1$ represents a peak width at half-height (min) of the first derivative, $W_2$ represents a peak width at half-height (min) of the second derivative, the denominator represents an absolute value, and R has a positive value.

12. A compound, represented by formula (104), (105), (112), (113), or (114):

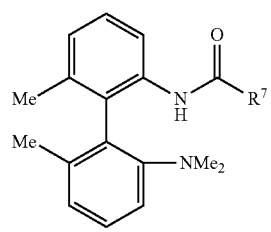

(104)

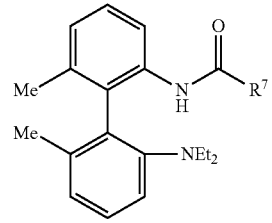

(105)

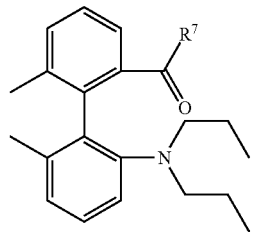

(112)

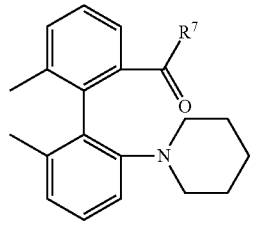

(113)

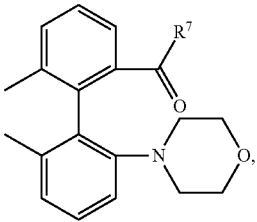

(114)

wherein $R^7$ represents a hydroxy group or a leaving group, wherein the leaving group is selected from the group consisting of $C_1$ to $C_6$ alkylcarbonyloxy, a halogen atom, succinimidooxy, phenyloxy having an electron-withdrawing group, imidazolyl, and triazolyl, or a salt thereof or mixture thereof.

13. A method for analyzing an enantiomer, comprising (1) to (3) below:

(1) reacting a mixture of a first compound and a second compound that are a pair of enantiomers with an axially chiral compound that is one of a pair of axially chiral isomers, to generate a derivative mixture containing a first derivative obtained by a reaction of the first compound with the axially chiral compound and a second derivative obtained by a reaction of the second compound with the axially chiral compound;

(2) separating said first derivative and said second derivative in the derivative mixture; and (3) detecting the separated first derivative and second derivative by mass spectrometry, wherein said axially chiral isomer is a compound according to claim 12.

14. A compound, represented by any one of the following formulae:

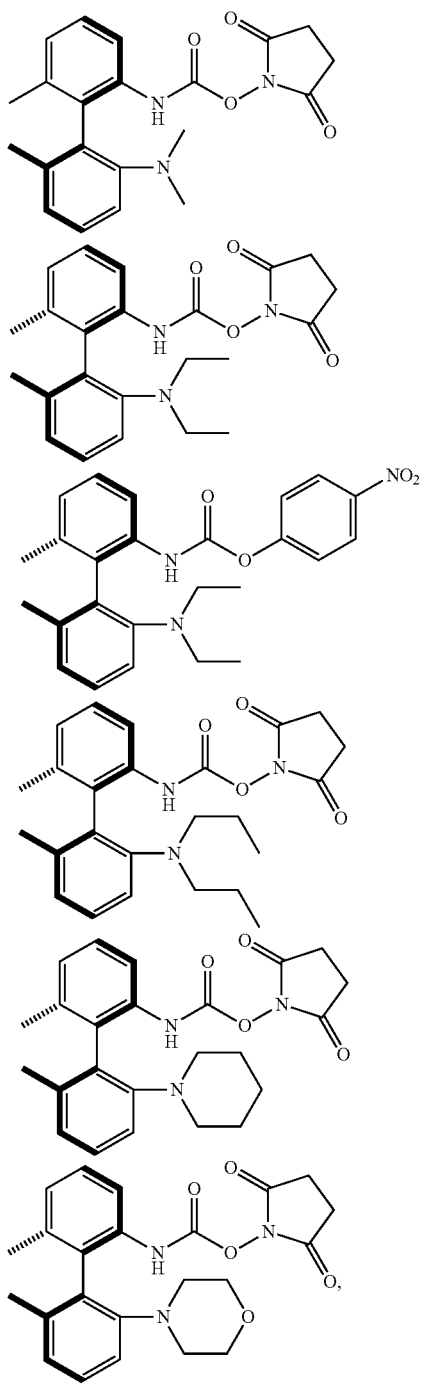

or a salt thereof or a mixture thereof.

15. A method for analyzing an enantiomer, comprising (1) to (3) below:
(1) reacting a mixture of a first compound and a second compound that are a pair of enantiomers with an axially chiral compound that is one of a pair of axially chiral isomers, to generate a derivative mixture containing a first derivative obtained by a reaction of the first compound with the axially chiral compound and a second derivative obtained by a reaction of the second compound with the axially chiral compound;
(2) separating said first derivative and said second derivative in the derivative mixture; and
(3) detecting the separated first derivative and second derivative by mass spectrometry,
wherein said axially chiral isomer is a compound according to claim 14.

16. A compound represented by formula (II-2):

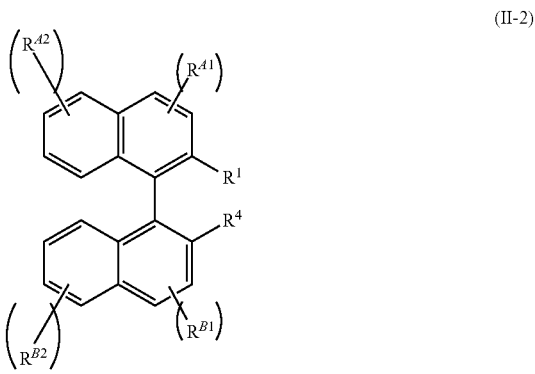

(II-2)

wherein
a bond between two naphthalene rings represents an axis of chirality,
$R^1$ represents a group represented by the general formula (i) or a group containing the group represented by the general formula (i),
$R^4$ represents a group having a charged atom or a chargeable atom, and
the two naphthalene rings optionally further have one or two $R^{A1}$s and one to four $R^{A2}$s and one or two $R^{B1}$s and one to four $R^{B2}$s that are bonded to an atom constituting each ring, wherein the one or two $R^{A1}$s and the one to four $R^{A2}$s and the one or two $R^{B1}$s and the one to four $R^{B}2$s each represent (c) a substituent,
wherein the group having a charged atom or a chargeable atom is a di($C_1$ to $C_6$ alkyl)amino group, a tri($C_1$ to $C_6$ alkyl)ammonio group, a piperidino group, a morpholino group, or a group represented by the general formula (d1) or the general formula (d2),
formula (i) is as below:

(i)

wherein
$R^7$ represents a hydroxy group or a leaving group, wherein the leaving group is selected from the group consisting of $C_1$ to $C_6$ alkylcarbonyloxy, a halogen atom, succinimidooxy, phenyloxy having an electron-withdrawing group, imidazolyl, and triazolyl,
n represents 0 or 1,
$R^8$ does not exist when n is 0, and
$R^8$ represents a hydrogen atom or a $C_1$ to $C_6$ alkyl group when n is 1, formula (d1) is as below:

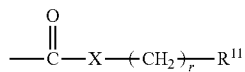
(d1)

wherein
X represents a nitrogen atom or an oxygen atom,
r represents an integer of 0 to 10,
$R^{11}$ represents a substituent having a positively charged nitrogen atom or a substituent having an uncharged nitrogen atom, and
formula (d2) is as below:

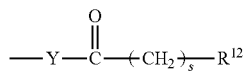
(d2)

wherein
Y represents a nitrogen atom or an oxygen atom,
s represents an integer of 0 to 10,
$R^{12}$ represents a substituent having a positively charged nitrogen atom or a substituent having an uncharged nitrogen atom,
wherein said (c) a substituent is not an amino group or a salt thereof or a mixture thereof.

17. A method for analyzing an enantiomer, comprising (1) to (3) below:
(1) reacting a mixture of a first compound and a second compound that are a pair of enantiomers with an axially chiral compound that is one of a pair of axially chiral isomers, to generate a derivative mixture containing a first derivative obtained by a reaction of the first compound with the axially chiral compound and a second derivative obtained by a reaction of the second compound with the axially chiral compound;
(2) separating said first derivative and said second derivative in the derivative mixture; and
(3) detecting the separated first derivative and second derivative by mass spectrometry,
wherein said axially chiral isomer is a compound according to claim 16.

* * * * *